United States Patent
Pho et al.

(10) Patent No.: US 12,268,530 B2
(45) Date of Patent: Apr. 8, 2025

(54) ILLNESS DETECTION BASED ON NERVOUS SYSTEM METRICS

(71) Applicant: Oura Health Oy, Oulu (FI)

(72) Inventors: Gerald Pho, Somerville, MA (US); Kirstin Aschbacher, San Francisco, CA (US); Marco Altini, Amsterdam (NL); Harpreet Rai, San Francisco, CA (US); Michael Chapp, Lafayete, CA (US)

(73) Assignee: Oura Health Oy, Oulu (FI)

( * ) Notice: Subject to any disclaimer, the term of this patent is extended or adjusted under 35 U.S.C. 154(b) by 360 days.

(21) Appl. No.: 17/357,562

(22) Filed: Jun. 24, 2021

(65) Prior Publication Data
US 2021/0401314 A1 Dec. 30, 2021

Related U.S. Application Data

(60) Provisional application No. 63/116,981, filed on Nov. 23, 2020, provisional application No. 63/049,405, (Continued)

(51) Int. Cl.
*A61B 5/00* (2006.01)
*A61B 5/01* (2006.01)
*A61B 5/024* (2006.01)
(Continued)

(52) U.S. Cl.
CPC .............. *A61B 5/7275* (2013.01); *A61B 5/01* (2013.01); *A61B 5/02405* (2013.01); (Continued)

(58) Field of Classification Search
None
See application file for complete search history.

(56) References Cited

U.S. PATENT DOCUMENTS 9,711,060 B1 * 7/2017 Lusted ............... A61B 5/02416
2001/0014776 A1 8/2001 Oriol et al.
(Continued)

FOREIGN PATENT DOCUMENTS

WO 2019217368 A1 11/2019

OTHER PUBLICATIONS

Training Peaks; How to Use HRV to Protect Illness; Simon Wegerif.
(Continued)

*Primary Examiner* — Sana Sahand
(74) *Attorney, Agent, or Firm* — Holland & Hart LLP

(57) ABSTRACT

Methods, systems, and devices for illness detection are described. A method may include receiving heart rate variability (HRV) data associated with a user from a wearable device, the HRV data collected via the wearable device throughout a first time interval and a second time interval subsequent to the first time interval. The method may include inputting the HRV data into a classifier, and identifying a satisfaction of deviation criteria between a first subset of the HRV data collected throughout the first time interval and a second subset of the HRV data collected throughout the second time interval. The method may include causing a graphical user interface (GUI) of a user device to display an illness risk metric for the user based on the satisfaction of the deviation criteria, the illness risk metric associated with a relative probability that the user will transition from a healthy state to an unhealthy state.

20 Claims, 18 Drawing Sheets

Related U.S. Application Data filed on Jul. 8, 2020, provisional application No. 63/043,892, filed on Jun. 25, 2020.

(51) Int. Cl.
*A61B 5/026* (2006.01)
*A61B 5/08* (2006.01)
*A61B 5/11* (2006.01)
*G16H 40/63* (2018.01)
*G16H 50/30* (2018.01)

(52) U.S. Cl.
CPC .............. *A61B 5/026* (2013.01); *A61B 5/08* (2013.01); *A61B 5/1118* (2013.01); *A61B 5/4806* (2013.01); *A61B 5/4812* (2013.01); *A61B 5/6826* (2013.01); *A61B 5/7264* (2013.01); *A61B 5/7267* (2013.01); *A61B 5/742* (2013.01); *A61B 5/7475* (2013.01); *G16H 40/63* (2018.01); *G16H 50/30* (2018.01); *A61B 2560/029* (2013.01)

(56) References Cited

U.S. PATENT DOCUMENTS

| | | | |
|---|---|---|---|
| 2007/0032733 A1* | 2/2007 | Burton | A61B 5/7264 600/509 |
| 2010/0174205 A1* | 7/2010 | Wegerif | A61B 5/02405 600/515 |
| 2019/0209022 A1* | 7/2019 | Sobol | A61B 5/681 |
| 2020/0311632 A1* | 10/2020 | Beck | G06Q 10/06311 |
| 2021/0298625 A1* | 9/2021 | Muthya | A61B 5/7275 |
| 2021/0345896 A1* | 11/2021 | Moore | A61B 5/6826 |
| 2022/0211285 A1* | 7/2022 | Mookerjee | A61B 5/0006 |

OTHER PUBLICATIONS

International Search Report and Written Opinion—PCT/US2021/039263—Jun. 25, 2021.

* cited by examiner

ILLNESS DETECTION BASED ON NERVOUS SYSTEM METRICS

FIELD OF TECHNOLOGY

The following relates to wearable devices and data processing, including illness detection based on nervous system metrics.

BACKGROUND

Some wearable devices may be configured to collect physiological data from users, including temperature data, heart rate data, and the like. Many users have a desire for more insight regarding their physical health.

DETAILED DESCRIPTION

Figure 1:
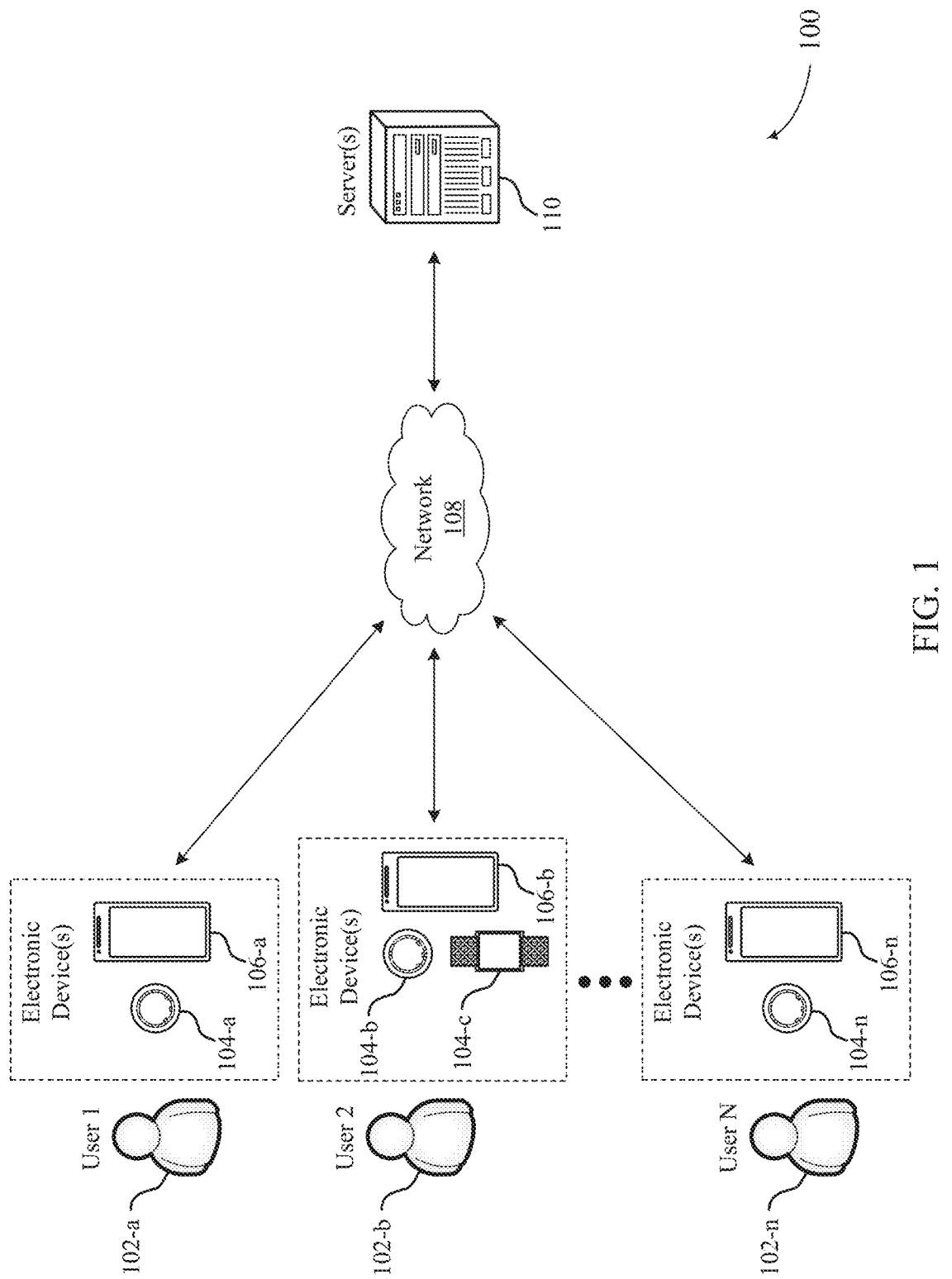
FIG. 1 illustrates an example of a system that supports illness detection techniques in accordance with aspects of the present disclosure.

Some wearable devices may be configured to collect physiological data from users, including temperature data, heart rate data, and the like. Acquired physiological data may be used to analyze the user's movement and other activities, such as sleeping patterns. Many users have a desire for more insight regarding their physical health, including their sleeping patterns, activity, and overall physical well-being.

Aspects of the present disclosure are directed to techniques for detecting and predicting illness. In particular, computing devices of the present disclosure may detect a user's transition from a healthy state to an unhealthy state. For example, aspects of the present disclosure may detect a transition from a healthy state to an unhealthy state at an early stage (e.g., before symptom onset), and notify the user of the potential transition prior to symptom onset and/or symptom aggravation associated with the upcoming unhealthy state. From the perspective of a user, the early detection (e.g., detection of illness before symptom onset) may appear as a prediction of the user's transition from a healthy state to an unhealthy state, or, in other words, may indicate that the user is experiencing an immunological response. As such, aspects of the present disclosure may detect and/or predict the onset of an unhealthy state in a user. In some implementations, the computing devices may also detect/predict the transition of a user from an unhealthy state to a healthy state.

For the purposes of the present disclosure, the term "healthy state," and like terms, may be used to refer to a user's physical state in which symptoms of illness and/or a particular diagnosis are absent (e.g., a normal state). Conversely, the term "unhealthy state," and like terms, may be used herein to refer to a user's physical state when the user is experiencing illness. For example, a user may be in an unhealthy state when experiencing disease symptoms, such as a fever, chills, a sore throat, headache, and other symptoms. Example illnesses that may cause an unhealthy state include, but are not limited to, bacterial or viral infections, such as influenza A/B and coronavirus disease 2019 (COVID-19).

A transition from a healthy state to an unhealthy state may refer to a transition from a state in which the user feels healthy to a state in which the user feels unhealthy, whereby those subjective symptoms may reflect the presence of an underlying illness, infection, condition, or diagnosis. For example, a transition from a healthy state to an unhealthy state may include the onset of symptoms, such as a fever and/or other conditions (e.g., decreased physical performance). Conversely, a transition from an unhealthy state to a healthy state may include a reduction, remission, or elimination of symptoms.

In some implementations, the healthy state and the unhealthy state may be referred to as a pre-symptomatic state and a symptomatic state, respectively. For example, in the healthy state, the user may not be experiencing symptoms (e.g., symptoms of an illness or infection). Although a user may not be experiencing symptoms (e.g., illness/infection symptoms), the user may be in a scenario in which they are transitioning to a state in which they may experience symptoms. For example, a user may be infected for a period of time while not experiencing symptoms. Put another way, a user may be experiencing an illness/infection, but may still be pre-symptomatic (e.g., feeling healthy). The pre-symptomatic period could also be when individuals are most likely to spread the illness. As such, there is a desire to detect illness during the pre-symptomatic state to enable interventions to stop the spread of illness.

After a period of time (e.g., an incubation period), the user may transition to a symptomatic state (e.g., an unhealthy state). Although a user may transition from a pre-symptomatic state to a symptomatic state, in some cases, users may not become symptomatic. Some aspects of the present disclosure are directed to the detection of illness during the pre-symptomatic stage (e.g., before the user experiences symptoms of the illness). However, techniques described herein may also be used to detect illness in cases where the user does not become symptomatic, or does not become aware of their symptoms.

Accordingly, some techniques of the present disclosure may be used to identify illness in the pre-symptomatic stage based on physiological data collected from a user via a wearable device (e.g., measured physiological data). Example physiological parameters may include, but are not limited to, nervous system information (e.g., heart rate data, heart rate variability (HRV) data), temperature data, respiration rate data, movement/activity data (e.g., actigraphy-based data associated with sleep and movement), and the like. For example, in some cases, techniques described herein may utilize changes in HRV data and other nervous system parameters to identify illness. In other cases, techniques described herein may utilize changes in temperature data for a user (e.g., changes in daytime high/low temperature readings) in conjunction with the user's location to identify illness. In additional or alternative implementations, techniques described herein may utilize data associated with modifiable behavioral predictors (e.g., physical activity, sleep) to identify illness. In some aspects, techniques described herein may utilize models (e.g., menstrual cycle models, weekly pattern adjustment models, annual pattern adjustment models, seasonal pattern adjustment models) to account for cyclical, predictable changes in the user's movement, activity, and physiological responses in order to improve prediction of illness onset.

In some aspects, techniques described herein may use physiological data collected over multiple different time intervals (e.g., reference window, prediction window) to detect illness. A comparison of physiological data collected over the respective time intervals may be used to identify satisfaction of deviation criteria, where the satisfaction of one or more deviation criteria may be used to identify a likelihood of illness. For example, techniques described herein may determine physiological parameter values for a user over a first time interval (e.g., reference window) while the user is in a healthy state to determine moving baseline parameters for the user (e.g., baseline temperature data, baseline HRV data). Techniques described herein may further compare physiological data collected over a second, subsequent time interval (e.g., prediction window) to the baseline parameters in order to determine deviations from the baseline parameters, where the deviations (e.g., satisfaction of deviation criteria) may be indicative of illness.

In additional or alternative implementations, a system described herein may determine personalized or group-derived "baseline" physiological parameter values (e.g., in a reference window) for the user in the healthy state. The system may then detect/predict the transition to an unhealthy state based on one or more deviations from these moving baseline physiological parameter values and/or the distribution of the baseline physiological parameter values (e.g., deviations included in one or more subsequent early detection/prediction windows).

In some implementations, to detect a transition from a healthy state to an unhealthy state, the systems and methods of the present disclosure may utilize one or more classifiers (e.g., machine learning classifiers, algorithms, etc.). For example, in some implementations, systems and methods of the present disclosure may employ change-point or anomaly detection strategies in a multivariate space utilizing Bayesian-influenced semi-supervised methodologies for performance evaluation. Hierarchical or mixed modeling approaches may be utilized to provide group-specific model parameters, thereby providing greater algorithmic precision to specific user segments. In other implementations, to detect a transition back to a healthy state (e.g., recovery from COVID-19 or other illness), the systems and methods of the present disclosure may detect a return from the deviated parameter values back to the earlier baseline parameter values/ranges.

Techniques described herein may notify a user of the detected/predicted transition from a healthy state to an unhealthy state in a variety of ways. For example, a system may cause a graphical user interface (GUI) of a user device to display a message or other notification to notify the user of the likelihood of a potential transition to an unhealthy state (e.g., illness risk metrics, illness prediction metrics), and make recommendations to the user. In one example, the GUI may display recommendations that the user prepare for a potential illness by resting, hydrating, and/or scheduling a doctor appointment. A GUI may also include graphics/text which indicate the data used to make the detection/prediction of an upcoming unhealthy state. For example, a GUI may indicate that an upcoming illness has been predicted based on temperature deviations from a normal baseline. Based on the early warnings (e.g., before noticeable symptoms), a user may take early steps that may help reduce the severity of an upcoming illness. Additionally, a user may modify/schedule their daily activities (e.g., work and leisure time) based on the early warnings.

In some implementations, the computing devices may notify an administrator (e.g., administrator of an organization, or medical professional overseeing a patient cohort) that is assigned to monitor a group of individuals in order to provide risk estimates or assist in the identification of individuals with the highest likelihood for requiring follow-up action for further testing or screening on the part of the organization. Such a device may present the model results as a tool for improving the selection of the subgroup of individuals to be offered additional care or for otherwise employing safety protocols. In such settings, the illness detection metrics and other illness scores may not be intended to be deterministic, absolute, or diagnostic, but rather to assist companies in preliminary assessment of risk, screening, or resource allocation, intended to be used in conjunction with additional tools for confirmatory diagnosis.

Aspects of the disclosure are initially described in the context of systems supporting physiological data collection from users via wearable devices. Additional aspects of the disclosure are described in the context of example nervous system diagrams, temperature data diagrams, modifiable behavioral predictor diagrams, an example menstrual cycle model, and an example health management platform. Aspects of the disclosure are further illustrated by and described with reference to apparatus diagrams, system diagrams, and flowcharts that relate to illness detection techniques.

FIG. 1 illustrates an example of a system 100 that supports illness detection techniques in accordance with aspects of the present disclosure. The system 100 includes a plurality of electronic devices (e.g., wearable devices 104, user devices 106) which may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, which may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may support techniques for automatic sleep stage classification based on data collected by a wearable device. In particular, the system 100 detect periods of time during which a user 102 is asleep, and classify periods of time during which the user 102 is asleep into one or more sleep stages. For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time during which the user 102-*a* is (or was) asleep. Moreover, the machine learning classifier may be configured to classify periods of time into different sleep stages, including an awake sleep stage, a REM sleep stage, a light sleep stage (non-REM (NREM)), and a deep sleep stage (NREM).

In some aspects, the classified sleep stages may be displayed to the user 102-*a* via a GUI of the user device 106-*a*. In particular, a GUI may display a time interval during which the user 102-*a* was asleep, where segments of the time interval are labeled or otherwise indicated with the corresponding sleep stages. In some implementations, sleep stage classification techniques described herein may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as sleep scores, readiness scores, and the like.

In some aspects, the system 100 may utilize circadian rhythm-derived features to further improve physiological data collection, illness detection, and other techniques described herein. The term circadian rhythm may refer to a natural, internal process that regulates an individual's sleep-wake cycle, which repeats approximately every 24 hours. In this regard, techniques described herein may utilize circadian rhythm adjustment models to improve sleep stage classification. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's sleep to provide more accurate sleep stage classification. In some implementations, the system may initially start with a "baseline" circadian rhythm adjustment model, and may modify the baseline model using physiological data collected from each user 102 to generate tailored, individualized circadian rhythm adjustment models which are specific to each respective user 102.

In some aspects, the system 100 may utilize other biological rhythms to further improve comparison of data by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within an individual. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals.

The biological rhythms described are not always identical across physiological modalities. For example, following travel across time zones, alignment of some rhythms to the new time zone may occur more quickly than for other rhythms or variables (e.g. ultradian rhythms may recover more quickly than circadian rhythms, or heart rate may recover its normal rhythmic characteristics more quickly than respiration rate). Similar loss of stable relationships is a common hallmark of illness. As such, classification of "healthy" and "unhealthy" time intervals can be further refined by the inclusion of rhythm parameters such as amplitude and instantaneous frequency per variable, and may be further refined by inclusion of parameters describing the relationships of rhythms across variables (as in, the alignment, co-information, coherence, etc., of ultradian rhythms in temperature to those in heart rate). The resultant relationship parameters must be generated in such a way as to preserve temporal resolution sufficient for the models being compared.

The biological rhythm-adjustment models and parameters can be added in linear or non-linear combinations as appropriate to more accurately capture the dynamic baseline of an individual or group of individuals. Weights and models can then be used as features to improve the accuracy of comparison between "healthy" time intervals and "unhealthy" time intervals. For example, a user's temperature data throughout their natural circadian rhythm (e.g., "temperature rhythm") may be compared to other physiological parameters evaluated with respect to the circadian rhythm (e.g., HRV rhythm, respiratory rate rhythm) to detect/predict illness.

In some aspects, the respective devices of the system 100 may support techniques for identifying illness onset. Aspects of the system 100 may support techniques for identifying illness during the pre-symptomatic stage (e.g., illness detection prior to symptom onset). In particular, the system 100 illustrated in FIG. 1 may support techniques for using classifiers (e.g., machine learning classifiers) to identify a likelihood that a user will transition from a healthy state to an unhealthy state based on physiological data collected from the user. In some implementations, techniques described herein may compare physiological data (and rhythm parameters thereof) collected over different time intervals (e.g., first/reference time interval, second/prediction time interval) to identify a satisfaction of deviation criteria, where the satisfaction of one or more deviation criteria may be used to predict illness risk metrics (e.g., "risk scores"), illness prediction metrics, illness severity metrics, illness recovery metrics, and the like.

For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a classifier, where the classifier is configured to determine illness risk metrics (or other metrics) associated with a likelihood or probability that the user will transition from a healthy state to an unhealthy state. In some aspects, the data input into the classifier may be processed to determine rhythm parameters across biological rhythms and physiological data types (e.g., ultradian rhythms and circadian rhythms in temperature, in heart rate, and in the relationships of those rhythms), with the resultant parameters also input into the classifier. In some aspects, the classifier may not be machine learning, but based on other artificial intelligence approaches, or empirically-derived linear discriminators not relying on artificial intelligence or machine learning.

The system 100 may be configured to cause the user device 106-a to display an indication of the illness risk metric, which may enable the user 102-a to take precautionary measures and/or adjust sleeping or activity routines in order to prevent the illness, reduce a severity of the illness, reduce a duration or the illness, prevent the spread of the illness, or any combination thereof.

In some cases, the system 100 may utilize nervous system metrics (e.g., metrics indicative of sympathetic/parasympathetic activity) to identify illness. For example, the system 100 may compare HRV data collected over different time intervals (e.g., reference window, prediction window) to identify satisfaction of deviation criteria, where the satisfaction of deviation criteria are indicative of illness onset. For instance, changes in high-frequency content of HRV data over time relative to changes in the low-frequency content of the HRV data over time may be used to identify illness onset.

In additional or alternative cases, the system 100 may utilize temperature data to identify illness onset. In particular, the system 100 may utilize temperature data in conjunction with a user's geographical position to determine illness onset. For example, changes in daytime high and/or low temperature readings for a first user 102 living in a colder climate (e.g., Finland) may be more indicative of illness as compared to changes in daytime high and/or low temperature readings for a second user 102 living in a warmer climate (e.g., Miami). Similarly, seasonal variation in biological rhythms will differ between northern (e.g. Finland) and southern (e.g. Miami) regions. As such, in some implementations, the system 100 may use location data (e.g., geographical position, latitude) to determine "predictive weights" for a user's temperature data, where the predictive weights are associated with a relative predictive accuracy of the temperature data for predicting illness. In such cases, the predictive weights may be used in conjunction with collected temperature data to determine how likely it is that a given user 102 will transition from a healthy state to an unhealthy state.

In additional or alternative cases, the system 100 may utilize physiological data associated with modifiable behavioral predictors (e.g., physical activity, sleep) to identify illness onset. For example, a machine learning classifier may be used to identify satisfaction of deviation criteria indicative of changes in a user's activity and/or sleep over time, where the changes in the user's activity and/or sleep over time may be used to identify illness. Moreover, in some implementations, the system 100 may utilize models (e.g., menstrual cycle models, weekly pattern adjustment models, yearly pattern adjustment models, seasonal pattern adjustment models) to account for cyclical, predictable changes in the user's movement, activity, and physiological responses in order to improve prediction of illness onset. For example, the system 100 may identify and/or generate a menstrual cycle model for the user 102-a, and may use the menstrual cycle model to improve illness detection for the user 102-a. In this example, the menstrual cycle model may be used to account for natural, cyclical changes in the user's physiological data based on the user's menstrual cycle (e.g., increased temperatures during a menstrual period), thereby reducing/eliminating false-positive illness predictions.

Techniques described herein may provide for improved illness detection using data collected by a wearable device. In particular, techniques described herein may be used to predict whether a user 102 will transition from a healthy state to an unhealthy state (or vice versa) based on physiological data collected from the user 102 via a wearable device. Physiological data used to perform illness detection may include nervous system information (e.g., heart rate data, HRV data), temperature data, respiration rate data, movement/activity data, sleep data, and the like. Moreover, the system 100 may utilize additional data, such as location data, to determine a predictive accuracy of various physiological parameters for identifying illness, which may improve an accuracy of illness detection techniques. Further, by accounting for cyclical, predictable changes in a user's activity, sleep, and/or physiological parameters (e.g., menstrual cycle models, weekly/seasonal/yearly pattern adjustment models), techniques described herein may further improve illness detection, thereby providing users 102 with more valuable insight regarding their overall physical health.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
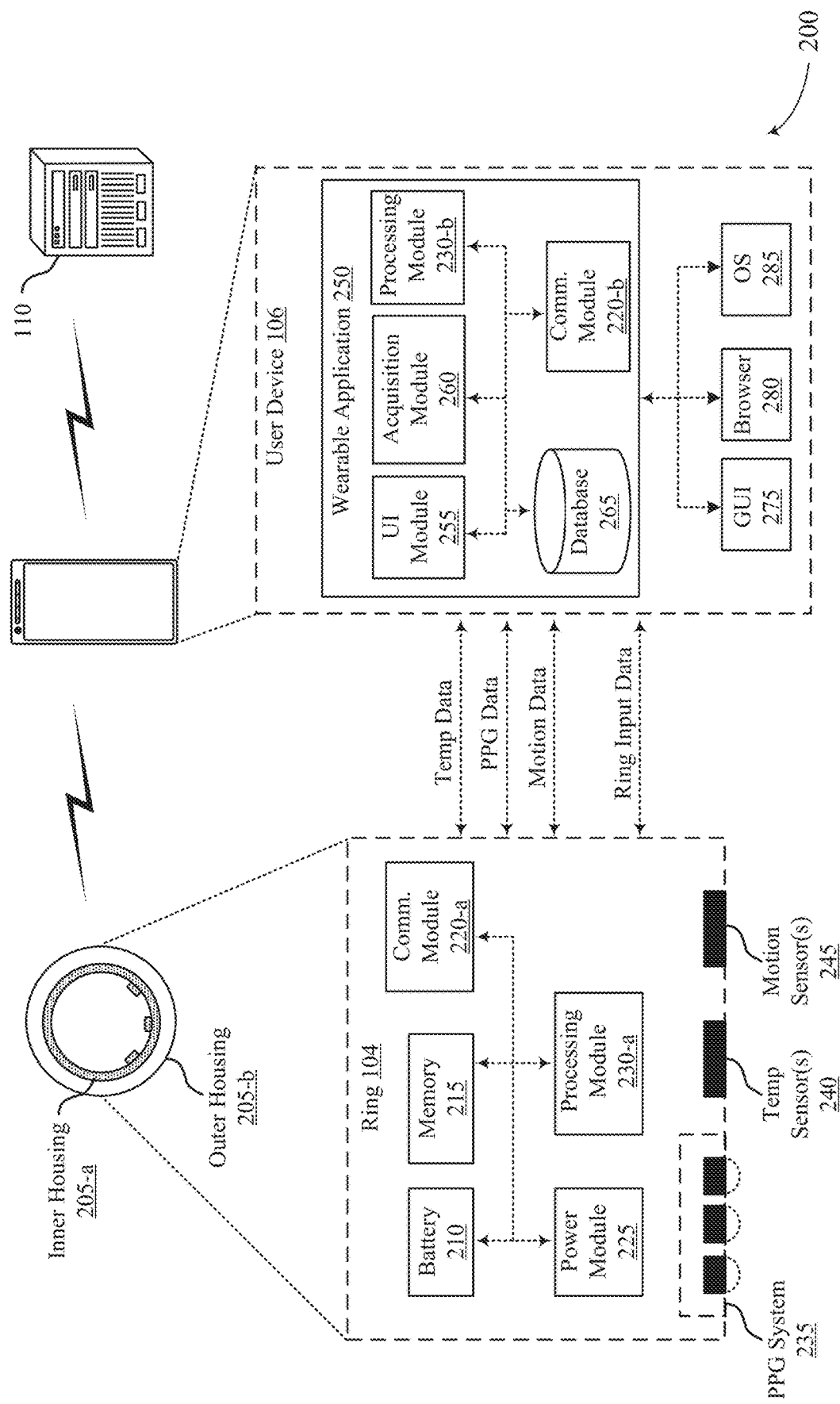
FIG. 2 illustrates an example of a system that supports illness detection techniques in accordance with aspects of the present disclosure.

FIG. 2 illustrates an example of a system 200 that supports illness detection techniques in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, which may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components which are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a plastic/rubber band and/or tape). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, which may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*a*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits).

The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-a, 220-b may include wireless communication circuits, such as Bluetooth circuits and/or Wi-Fi circuits. In some implementations, the communication modules 220-a, 220-b can include wired communication circuits, such as Universal Serial Bus (USB) communication circuits. Using the communication module 220-a, the ring 104 and the user device 106 may be configured to communicate with each other. The processing module 230-a of the ring may be configured transmit/receive data to/from the user device 106 via the communication module 220-a. Example data may include, but is not limited to, motion data, temperature data, pulse waveforms, heart rate data, HRV data, PPG data, and status updates (e.g., charging status, battery charge level, and/or ring 104 configuration settings). The processing module 230-a of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors which may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ than the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, which may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Additionally, or alternatively, respiratory rate may be determined based on HRV data. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a sleep score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during 104 a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. For example, in some implementations, the ring 104 may be configured to acquire physiological data (e.g., determine temperature readings, HRV readings, respiratory rate readings) continuously in accordance to one or more measurement periodicities throughout the entirety of each day/sleep day. In other words, the ring 104 may continuously acquire physiological data from the user without regard to "trigger conditions" for performing such measurements.

In additional or alternative implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") which may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations which require relatively low processing power and/or operations which require a relatively low latency, whereas the user device 106 may transmit the data to the servers 110 for processing operations which require relatively high processing power and/or operations which may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., sleep score, readiness score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, sleep scores, readiness scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner which is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., sleep score, readiness score) may be determined/calculated based on one or more "contributors," "factors," or "contributing factors." For example, a user's overall sleep score may be calculated on a set of contributors, including: total sleep, efficiency, restfulness, rapid eye movement (REM) sleep, deep sleep, latency, timing, or any combination thereof. The sleep score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall readiness score may be calculated based on a set of contributors, including: sleep, sleep balance, heart rate, HRV balance, recovery index, temperature, activity, activity balance, or any combination thereof. The readiness score may include any quantity of contributors. The "sleep" contributor may refer to the combined sleep score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the readiness score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some implementations, the various devices of the system 200 may support techniques for illness detection. In particular, the system 200 may support illness detection based on physiological data indicative of a user's neuro-immune and nervous system responses during the pre-symptomatic period of an infection or illness. The early incubation period of an infection, before people know they are symptomatic, is a key window of opportunity for early detection. Markers of nervous system balance derived from wearables may help us detect the onset of infection and the transition to symptomatic illness, in the "incubation period" before people know that they are sick. For example, in the context of COVID-19, people can be infected without experiencing any symptoms for up to 14 days before they actually develop a fever or feel sick. This 14-day period may be referred to as the "pre-symptomatic period" for COVID-19. Influenza can have a shorter incubation time or pre-symptomatic period, typically up to 4 days. The pre-symptomatic period is also when individuals are most likely to spread the virus. As such, there is a desire to detect illness during the pre-symptomatic state to enable interventions to stop the spread of illness.

For many kinds of influenza-like illness, including COVID-19, and other viral or bacterial infections, the body's immune response to the invading pathogen modulates the autonomic nervous system, thereby also transmitting signals to the brain (e.g., inflammatory cytokines) that can result in "sickness symptoms." Physiological data collected by a wearable device (e.g., ring 104) may detect these early nervous system alterations, by building markers or "features" fed to a classifier/algorithm (e.g., machine learning classifier). These markers can be derived from continuous heart rate monitoring, PPG data, the derived IBI series, or any combination thereof. Because PPG and other physiological data measured at the finger is based on arterial blood flow (as compared to capillary blood flow), physiological data collected from the finger via the ring 104 may be more sensitive and accurate as compared to physiological data collected from the wrist, thereby providing a uniquely sensitive signal for nervous system balance markers to detect illness during the incubation (or pre-symptomatic) period.

A user's nervous system balance may involve the relative antagonism (e.g., push-and-pull) of the user's sympathetic and parasympathetic nervous system responses. In particular, when exposed to stress (e.g., exposure to illness/infection, or attack from pathogens), the parasympathetic nervous system (e.g., portion of the nervous system associated with "resting and digesting" or restoration) may withdraw some of its tonic, inhibitory input to the heart, immune cells, and other bodily tissues. By essentially "taking the foot off the break," the nervous system can allow for greater sympathetic input, engaging the "fight or flight" system. This is advantageous to the immune system at the earliest stages of infection by mobilizing immune cells like monocyte/macrophages from the bone marrow into the blood stream and the tissues where they seek out virally infected cells. Hence, changes in the nervous system may occur close to the time of infection or before symptom onset (e.g., 2-14 days prior to symptom onset for COVID-19).

The antagonism between the sympathetic and parasympathetic responses results in a "nervous system balance," which may describe a combination of coordinated adrenergic and cholinergic inputs affecting the heart rate and vasculature, manifesting as changes in PPG-derived markers and affecting the user's immune response to infection/illness. Fundamentally, both counter-regulatory aspects of the nervous system (sympathetic/adrenergic and parasympathetic/cholinergic) are needed, and do not always move in counter-regulatory fashion as is traditionally presented in some textbooks and other literature.

In response to an infection/illness, the brain sends signals via the nervous system to peripheral immune organs such as the bone marrow and spleen. These signals release more immune cells such as monocyte/macrophages into the bloodstream, where the immune cells can help hunt down and fight infected cells. Nervous system balance is needed to control this immunologic response to infection and to guide recovery from illness. Nervous system balance is a function of both the parasympathetic and sympathetic nervous system inputs to the heart and to immune cells. Moreover, sleep is unique in the context of nervous system balance: the nervous system balance has different patterns of activation during the day versus night (or waking versus sleeping). Accordingly, it is contemplated herein that wearable devices 104 of the system 200 (e.g., ring 104) may be configured to capture physiological data indicative of sleep and other nervous system responses, which may provide a unique measurement of nocturnal nervous system balance prior to (and during) infection/illness.

A user's nervous system mediates connections between the immune system and the brain to fight illness/infection, which provides a critical signaling pathway by which the brain "learns" when the body has been infected with an illness (e.g., influenza-like respiratory virus), coordinates a whole-body response to infection, and manifests "sickness symptoms" like fatigue, pain, and the like, to aid the body in fighting the infection. For example, upon identifying an infection, the nervous system may convey inflammatory signals to the hypothalamic centers of the brain that regulate body temperature, thereby causing the body to mount a fever, which may enhance survival by inhibiting viral replication.

Nonetheless, because the nervous system also responds to many other stimuli other than illness/infection, the system 200 may be configured to combine subtle changes across many markers in order to detect a larger pattern indicative of response to illness. Indeed, individual features associated with collected physiological data, on their own, may not be highly indicative of illness. However, when multiple features are combined together and taken in combination with many features/markers, machine learning classifiers of the system 200 may be highly accurate in detecting illness. Thus, the system 200 may utilize multiple aspects of the nervous system's balance between the parasympathetic and sympathetic, and the behavioral consequences that infection drives (e.g., such as sleeping earlier or longer) in order to identify illness. In other words, techniques described herein may determine/predict illness based on learned patterns of deviations within a user's activity, sleep, and/or physiological data, rather than individual "anomalies" within a single parameter or feature.

Accordingly, the system 200 may support techniques for identifying illness onset using physiological data indicative of nervous system responses (e.g., HRV, respiratory rate). In particular, techniques described herein may compare HRV data collected from a user throughout a first time interval (reference window) and a second time interval (prediction window), and may determine a satisfaction of deviation criteria based on changes in HRV data from the first time interval to the second time interval. The satisfaction of the deviation criteria may then be used to determine an "illness risk score," "illness prediction metric," or some other metric indicative of illness for the user, and may report the determined metrics to the user via the GUI 275 of the user device 106. In other words, the system 200 may collect HRV data from a user, and compare the collected HRV data to that same user's baseline HRV data to determine deviations from the user's baseline HRV data, where the deviations may be indicative of illness. Additionally, or alternatively, the system 200 may determine a respiratory rate for the user (e.g., based on HRV data), and may determine deviations from a user's baseline respiratory rate in order to identify illness onset.

In some implementations, collected HRV data may be input into a classifier, where the classifier is configured to identify the satisfaction of one more deviation criteria across the respective time intervals (e.g., reference window, prediction window) in order to detect illness. In some implementations, frequency content of HRV data collected from a user may be used to identify illness onset. For example, the ring 104, the user device 106, and/or the servers 110 of the system 200 may determine HRV frequency bands and time domain metrics associated with HRV data collected from a user. Time domain content/metrics of HRV data may include root mean square of successive differences (RMSSD). Further, frequency domain content/metrics of HRV data may include a high frequency (HF: 0.15-0.40 Hz; min period=30 seconds; rolling window=1 min) and a low frequency (LF: 0.04-0.15 Hz; min period=90 seconds; rolling window=2-5 min) range, respiration rate, and a very low frequency (VLF: 0.015-0.04 Hz; min period 270 seconds). These frequency features may be computed on a rolling basis over windows of 1-10 minutes depending on the length of the frequency in question, after having removed motion and other artifacts and ectopic beats from the signal.

The various components of the system 200 may determine the raw spectral power in the respective frequency bands and/or the peak frequency for each respective frequency band. These frequency extractions at high resolution granularity may be fed into a feature engineering pipeline which is configured to extract various statistical parameters from various points during the sleep period. These may include, but are not limited to, quantiles of a distribution (e.g., 1%, 50%, 99%, etc.) or metrics that examine shifts in an entire distribution such as the Wasserstein metric. In other words, the feature engineering pipeline may be configured to compute features for certain time windows (e.g., rolling 1-10 minute time windows), as well as compute statistics over time windows (e.g., median values over the course of a night), where the computed features and statistics may be fed into classifiers (e.g., machine learning classifiers) to perform the various illness detection techniques described herein. In some implementations, changes in distributions may be framed using Bayesian statistics to reflect the influence of prior knowledge about a given user's range of values in a personalized manner over various "baseline periods."

In some implementations, features associated with physiological data associated with nervous system responses (e.g., HRV data) may be extracted in "sleep intelligent" ways, such as isolating the respiration rate during REM versus non-REM sleep. Features may be extracted from the early, middle, or late portions of the evening, where different physiologic influences may predominate. For example, the immune system's circadian rhythm suggests that between approximately 9:00 pm and 2:00 am, the immune system may be poised to mount a strong attack and secrete more cytokines, whereas in the later portion of the evening, the sympathetically mediated splanchnic nervous signals may initiate signals that entrain the circadian rhythms for the next day and thereby impact the signals in critical ways. Hence, the system 200 may be configured to perform illness detection based on physiological data collected across the entire night's sleep, based on physiological data collected across multiple sleep periods, and/or "sleep stage intelligent" or chronologically-informed features based on physiological data collected within time intervals determined according to known circadian rhythms and physiology.

In some aspects, the system 200 may determine frequency content of the HRV data throughout respective time intervals (e.g., first/reference time interval, second/prediction time interval). For example, a feature engineering pipeline of the system 200 (and/or machine learning classifier) may determine frequency and amplitude (e.g., raw spectral power) of high-frequency signals and low-frequency signals in rolling time windows (e.g., rolling two-minute time intervals) across a night of collected physiological data. The system 200 may then compute statistics on determined features (e.g., 50% quantile of high-frequency amplitude across the whole night of rolling two-minute intervals) to determine a single set of parameters/values for the respective night of physiological data.

Frequency content associated with acquired HRV data may be further shown and described with reference to FIG. 3.

Figure 3:
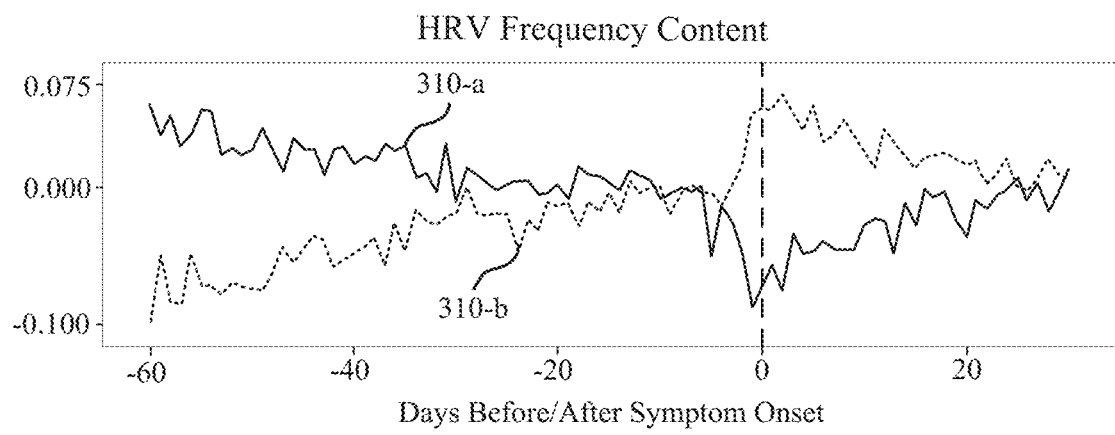
FIG. 3 illustrates an example of a nervous system diagram that supports illness detection techniques in accordance with aspects of the present disclosure.
Figure 3:
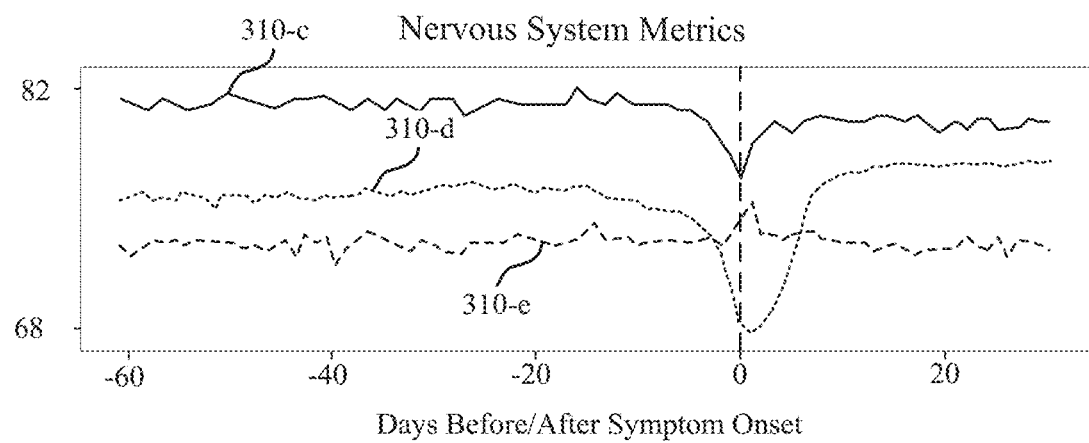

FIG. 3 illustrates an example of a nervous system diagram 300 that supports illness detection techniques in accordance with aspects of the present disclosure. In particular, the nervous system diagram 300 includes an HRV frequency content diagram 305-a and a nervous system metric diagram 305-b.

The HRV frequency content diagram 305-a illustrates how analyzing HRV frequency bands may be used to capture a divergence of sympathetic and parasympathetic indicators prior to illness to detect illness in the pre-symptomatic stage. In particular, the HRV frequency content diagram 305-a illustrates low-frequency content (low-frequency curve 310-a) and high-frequency content (high-frequency curve 310-b) for more than 10,000 individuals who experienced influenza-like symptoms, including symptoms associated with COVID-19. The x-axis of the HRV frequency content diagram 305-a illustrates time (e.g., days) before and after symptom onset, with time=0 indicating symptom onset (e.g., first development of symptoms) for the respective users. The y-axis of the HRV frequency content diagram 305-a is normalized to graph two different metrics (e.g., low-frequency curve 310-a and high-frequency curve 310-b) together.

The low-frequency curve 310-a represents the ninety-nine percentile (99% ile) of the peak frequency in the low-frequency band, an HRV metric, derived from the IBI series during the nocturnal sleeping period. The high-frequency curve 310-b represents the one percentile (1% ile) of the peak frequency in the high-frequency band, another HRV metric derived from the IBI series during the nocturnal sleeping period. In some aspects, the low-frequency curve 310-a may be representative of the sympathetic nervous system response, whereas the high-frequency curve 310-b may be representative of the parasympathetic nervous system response.

As shown in the HRV frequency content diagram 305-a, there may be a coordinated shift in the range of the two frequencies prior to symptom onset. That is, there is a divergence between the low-frequency curve 310-a and the high-frequency curve 310-b prior to symptom onset. Because the low-frequency curve 310-a and the high-frequency curve 310-b are associated with sympathetic and parasympathetic activity, respectively, the divergence of the respective curves 310 prior to symptom onset may make the respective responses (e.g., sympathetic response, parasympathetic response) more distinct. This divergence between the low-frequency curve 310-a and the high-frequency curve 310-b may reflect changes in the inputs to immune organs such as the bone marrow, to stimulate the release of immune cells into the bloodstream to fight infection.

In some aspects, the system 200 may identify illness in the pre-symptomatic stage (e.g., prior to illness onset at time=0) based on the low-frequency content of a user's HRV data (e.g., low-frequency curve 310-a) and/or the high-frequency content of the user's HRV data (e.g., high-frequency curve 310-b). In some cases, the system 200 (e.g., ring 104, user device 106, servers 110, machine learning classifier) may identify the divergence of the low-frequency curve 310-a and the high-frequency curve 310-b to identify illness. For example, during a first interval (e.g., reference window), the normalized low-frequency curve 310-a may be greater than the normalized high-frequency curve 310-b. Comparatively, during a second time interval (e.g., prediction window), the normalized high-frequency curve 310-b may be greater than the normalized low-frequency curve 310-a. As such, the system 200 may detect illness onset based on a divergence between the respective curves 310 between the first time interval and the second time interval.

The system 200 may utilize additional physiological parameters associated with nervous system response to determine illness onset. For example, the nervous system metric diagram 305-b illustrates three different metrics derived from a user's IBI series which may be used for illness detection: resting heart rate (curve 310-c), HRV averaging score (curve 310-d), and recovery metric (curve 310-e). In some implementations, as described previously herein, resting heart rate, HRV averaging score (e.g., "HRV balance"), and recovery metric (e.g., "recovery index") may include "contributors" or "contributing factors" which are used to determine a user's readiness score.

The x-axis of the nervous system metric diagram 305-b illustrates time (e.g., days) before and after symptom onset, with time=0 indicating symptom onset (e.g., first development of symptoms) for the respective users. The data for the respective curves 310-c, 310-d, and 310-e of the nervous system metric diagram 305-b may be computed by comparing recent data against a user's long-term average, normalized from 0 to 100 (y-axis). As shown in FIG. 3, the respective nervous system metrics indicated in the nervous system metric diagram 305-b may provide valuable insight for illness detection in the pre-symptomatic period.

In particular, curve 310-d associated with a user's HRV averaging score, or "HRV balance," declines substantially prior to symptom onset. The curve 310-d reflecting a user's HRV averaging score (e.g., HRV balance) compares recent nighttime HRV (e.g., fourteen-day weighted mean of log-transformed RMSSD, with more weight given to more recent data) with a user's long-term HRV over the past several months. Additionally, it may also be seen that curve 310-c reflecting resting heart rate (which compares the previous night's lowest ten-minute heart rate to the long-term mean of the user's heart rate) also declines prior to symptom onset. Lastly, curve 310-e reflecting recovery index (e.g., recovery metric data) for readiness scores also exhibits an increase in the days leading up to symptom onset. Recovery metric data, or recovery index, may refer to how long it takes for a user's resting heart rate to stabilize overnight. The increase in curve 310-e may reflect an increase in the proportion of the night dedicated to recovery once the heart rate has reached its lowest point. Longer than usual recovery times may be mildly predictive of illness. Taken together, decreases in curve 310-c (e.g., decrease in resting heart rate), decreases in curve 310-d (e.g., decrease in HRV averaging score), increases in curve 310-e (e.g., increase in recovery metric data), or any combination thereof, may be used for illness prediction.

Figure 4:
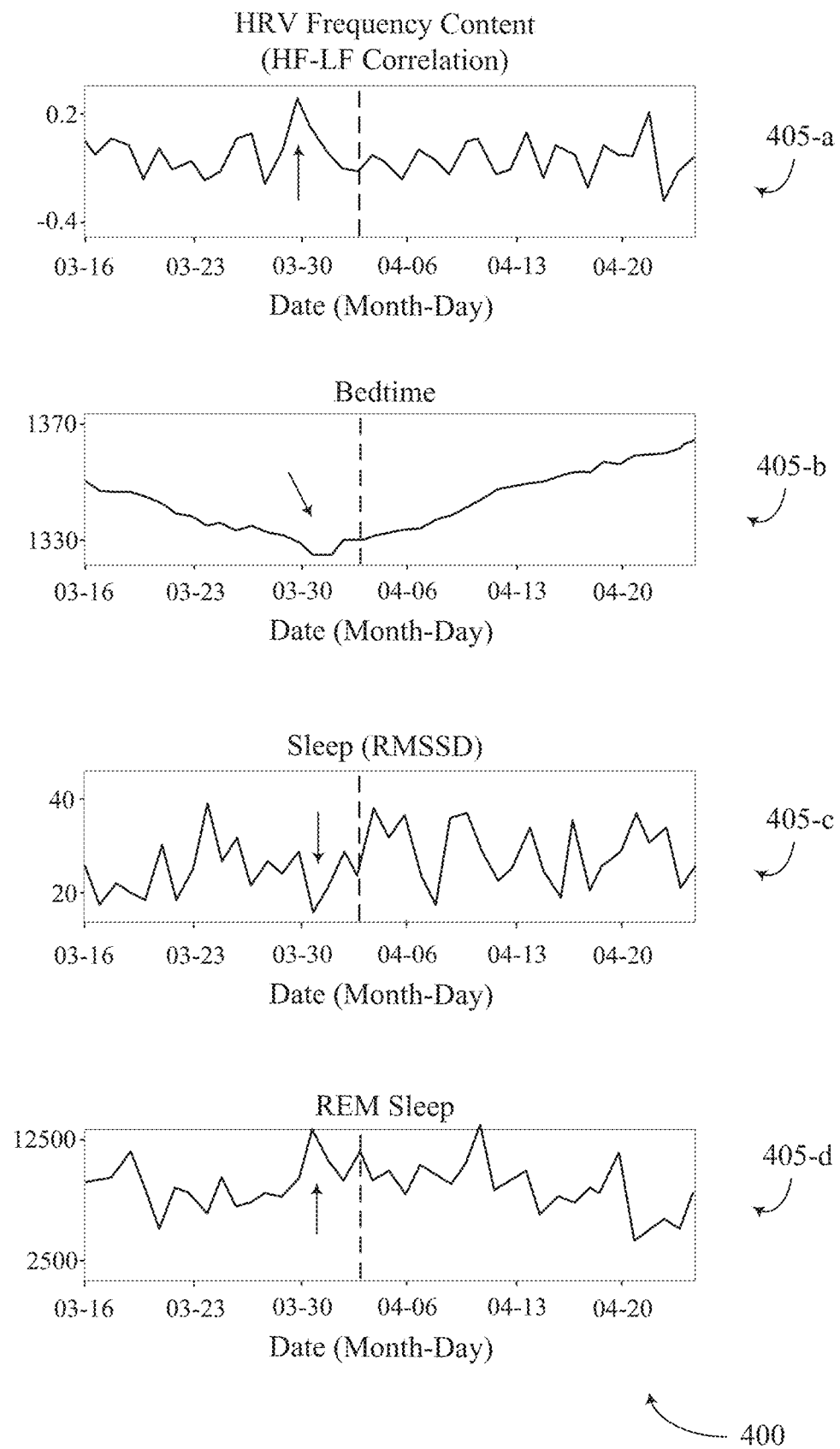
FIG. 4 illustrates an example of a nervous system diagram that supports illness detection techniques in accordance with aspects of the present disclosure.

FIG. 4 illustrates an example of a nervous system diagram 400 that supports illness detection techniques in accordance with aspects of the present disclosure. In particular, the nervous system diagram 400 includes an HRV frequency content diagram 405-a, a bedtime diagram 405-b, an RMSSD diagram 405-c, and a REM sleep diagram 405-d.

The x-axis of the respective diagrams 405-a through 405-d illustrates a date (e.g., month-day) before and after symptom onset, where the vertical reference line in each of the diagrams 405 illustrate the onset of illness symptoms for the user. The y-axis of the HRV frequency content diagram 405-a illustrates a correlation between high and low frequency content of HRV data from the user. The y-axis of the bedtime diagram 405-b illustrates a bedtime for the user, measured as a time duration (in minutes) following midnight for the respective date. The y-axis of the RMSSD diagram 405-c illustrates an RMSSD measure in milliseconds of a longest sleep duration for the user, and the y-axis of the REM sleep diagram 405-d illustrates the total REM sleep duration in seconds for the user.

As seen in the HRV frequency content diagram 405-a, there is a marked increase in the correlation of high-frequency HRV peak frequencies and low-frequency HRV peak frequencies roughly 5-7 days before symptom onset. Additionally, the bedtime diagram 405-b illustrates that users may go to bed earlier in the days leading up to symptom onset (e.g., decrease in the curve of bedtime diagram 405-b), and the RMSSD diagram 405-c illustrates lower RMSSD of HRV data in the days leading up to symptom onset. The decrease in RMSSD (and/or other HRV metrics) may indicate a withdrawal of the parasympathetic nervous symptom, which may be indicative of oncoming illness. Lastly, the REM sleep diagram 405-d illustrates an increase in REM sleep leading up to symptom onset.

While the individual nervous system characteristics/parameters illustrated in FIG. 4 may be somewhat noisy individually, these respective parameters may be used to effectively predict illness when taken together or as a combination. For example, an increase in the correlation between high-frequency and low-frequency HRV content along with earlier bedtimes and increased REM sleep may be used to identify that a user may transition from a healthy state to an unhealthy state.

Figure 5:
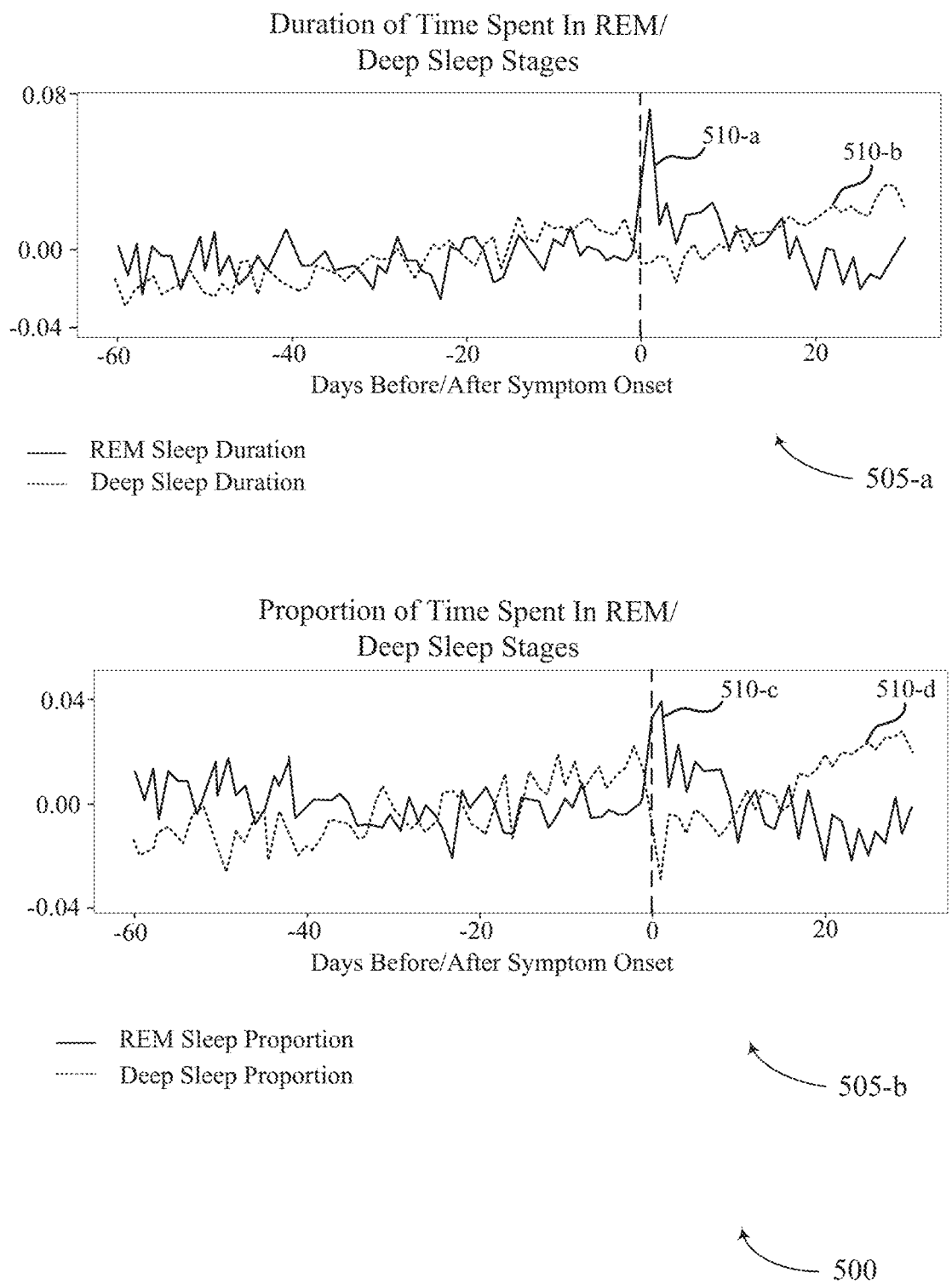
FIG. 5 illustrates an example of a nervous system diagram that supports illness detection techniques in accordance with aspects of the present disclosure.

FIG. 5 illustrates an example of a nervous system diagram 500 that supports illness detection techniques in accordance with aspects of the present disclosure. In particular, the nervous system diagram 500 includes a first diagram 505-a which illustrates a longest sleep duration for deep and REM sleep stages, and a second diagram 505-b which illustrates a relative proportion of total sleep which is classified as deep and REM sleep.

The x-axis of the respective diagrams 505-a and 505-b illustrates time (e.g., days) before and after symptom onset, with time=0 indicating a symptom onset date for respective users. The y-axes of the respective diagrams 505-a and 505-b are z-normalized to illustrate the respective curves on the same graph, where the first diagram 505-a illustrates a length of time a respective user spent in a REM sleep stage (curve 510-a) and a deep sleep stage (curve 510-b), and the second diagram 505-b illustrates a relative proportion of a user's total sleep that is classified as REM sleep (curve 510-c) or deep sleep (curve 510-d).

During sleep, users exhibit different sleep stages/phases (e.g., deep sleep stage, light sleep stage, REM sleep stage, awake sleep stage). REM and non-REM sleep stages have characteristically different patterns of nervous system balance, and changes in the respective sleep stages may be used to predict illness onset. In particular, the system 200 may be configured to input physiological data collected from the ring 104 (e.g., HRV data, respiratory rate data, temperature data, etc.) into a classifier (e.g., machine learning classifier), where the classifier classifies the physiological data into respective sleep stages. Subsequently, sleep stage data (e.g., data indicating durations which the user spent in the respective sleep stages) may be used to predict illness. In this regard, the classifier/algorithm may create or "learn" the complex interactions that occur between these sleep stages and the metrics of nervous system balance or HRV. By looking at these features together, a machine learning classifier may develop a more accurate understanding of the complexity of how the nervous system responds to illness during sleep.

For example, as shown in the first diagram 505-a, an increase in a length of time that a user spends in REM sleep (e.g., increase in curve 510-a), as well as a decrease in a length of time the user spends in deep sleep (e.g., decrease in curve 510-b), may be used to predict that a user will transition from a healthy state to an unhealthy state. Moreover, as shown in the second diagram 505-b, an increase in the relative proportion of a user's sleep spent in REM sleep (e.g., increase in curve 510-c) and a decrease in the relative proportion of the user's sleep spent in deep sleep (e.g., decrease in curve 510-d)) may additionally or alternatively be used to predict symptom onset.

In some cases, physiological data acquired from the user may be used in "sleep intelligent" manners in order to predict illness. That is, the system 200 may utilize only physiological data collected during specific periods of the night and/or specific sleep stages when predicting illness. For example, chronologically informed features may be determined based on known circadian rhythms and physiology for a user, where features may be extracted from the early, middle, or late portions of the evening, where different physiologic influences may predominate.

For example, it may be the case that HRV data collected during periods of REM sleep are more useful for detecting illness as compared to HRV data collected during other sleep stages (e.g., deep sleep stage, light sleep stage). As such, in some implementations, the system 200 may utilize physiological data collected during defined sleep stages, time durations during a night, and/or type of sleep stage when predicting illness. For instance, the system 200 may utilize HRV data collected during REM sleep stages within a first time interval (e.g., reference window) and HRV data collected during REM sleep stages within a second time interval (e.g., prediction window) in order to identify satisfaction of deviation criteria and predict illness onset.

Similarly, the system 200 may utilize physiological data collected at defined time intervals throughout a user's natural circadian rhythm cycle to determine illness. For example, according to a user's natural circadian rhythm, physiological changes between approximately 2:00 am and 4:00 am may be more indicative of illness, as this time interval may correspond to a time during which the body is naturally prone to increase biological responses to fight illness. By way of another example, according to a user's natural circadian rhythm, physiological changes within the first 180 minutes after a user's normal bedtime (e.g., first 180 minutes of expected sleep), and the last 180 minutes before the user's normal wake time (e.g., last 180 minutes of expected sleep) may be more indicative of illness. In other words, a user's natural circadian rhythm may be used to identify absolute and relative time windows which may be of particular interest when determining/predicting illness. As such, the system 200 may identify the circadian rhythm for the user, and may compare physiological data collected within specific time intervals of the circadian rhythm to physiological data collected within the same time intervals of the circadian rhythm in order to detect illness. For instance, the system 200 may compare HRV data collected between 2:00 am and 4:00 am to a user's baseline HRV data collected between 2:00 am and 4:00 am on previous days in order to determine deviations from the baseline HRV data, and to detect illness.

An example for determining/predicting a user's transition from a healthy state to an unhealthy state may be illustrative. In this example, the ring 104 may acquire physiological data from a user over time. For example, the ring 104 may acquire/determine at least one of the user's HRV data, temperature data, pulse waveform data, respiratory rate, heart rate, blood oxygen level, or any combination thereof. The respective data streams (e.g., temperature data, heart rate data, HRV data, etc.) may be referred to as "parameters" of the physiological data. The ring 104 may transmit the acquired/determined physiological data to the user device 106. Moreover, in some aspects, the user device 106 may transmit the acquired physiological data to the server 110.

The user device 106 and/or server 110 may determine healthy baseline values/ranges based on data acquired during a first time interval, which may be referred to herein as a "baseline determination window" or "reference window." The user device 106 may determine values used for deviation determinations during a second time interval, which may be referred to herein as an "early detection window" or "prediction window." The prediction window may be a window of time that occurs after the reference window. In some implementations, the reference window may abut the early detection window, such that the two time windows form a continuous time window. In some implementations, the two time windows may be separated from one another by a period of time. In some implementations, the same time windows may be used for calculating different baselines/deviations. In some implementations, different time windows may be used for calculating different baselines/deviations. The time windows for the reference window, prediction window, unhealthy time window, and recovery time window may be of any duration. For example, the time windows may be on the order of minutes, hours, days, or weeks.

The user device 106 and/or the server 110 may determine healthy baseline values/ranges for the respective parameters of the physiological data. The healthy baseline values/ranges may indicate values and/or ranges of values for the user's physiological parameters when the user is in the healthy state. For example, the healthy baseline values/ranges may indicate healthy temperature characteristics, respiratory rate characteristics, HR characteristics, and/or HRV characteristics. The user device 106 may determine one or more healthy baseline values/ranges for each of the measured physiological parameters. For example, the user device 106 and/or server 110 may determine healthy baseline HRV ranges, healthy baseline respiratory rate ranges, healthy baseline temperature ranges, and the like. The user device 106 and/or server 110 may determine healthy baseline values/ranges for the respective parameters based on acquired physiological data in a baseline reference window (e.g., first time interval). In some implementations, the baseline values/ranges may be values/ranges in the time domain, frequency domain, or both.

For the purposes of the present disclosure, the terms "physiological data," "baseline physiological data," and like terms, may be used to refer not only to collected physiological readings (e.g., temperature readings, heart rate readings, etc.), but also to other parameters/characteristics associated with the collected physiological readings, such as frequency, amplitude, phase, etc. For example, the term "baseline temperature data" may refer to raw/processed temperature readings collected from a user, as well as frequency content of the temperature data. In this regard, the term "physiological data," and like terms, may be used interchangeably with "physiological parameters," "dynamic physiological parameters," "physiological characteristics," and the like. For example, the term "temperature data" may be used interchangeably with the term "dynamic temperature parameters" or "temperature characteristics" to refer to raw/processed temperature readings, as well as other rhythmic temperature parameters, such as frequency, amplitude, phase, stability, and the like.

In some cases, the user device 106 and/or servers 110 may select the first time interval (e.g., reference window) and the second time interval (e.g., prediction window) used for illness detection. In some implementations, Bayesian statistical methods may be utilized whereby the reference window constitutes the prior distribution and the prediction window constitutes the posterior distribution. In other implementations, Bayesian methods may be used to select an appropriate discrimination threshold at which a model-outputted probability of illness may be classified as actionable or unactionable from the perspective of a user or employer-based product. For example, the prevalence of COVID-19 in a local region or employment center or similar demographic may provide a prior distribution against which to assess the statistical likelihood of a posterior data-driven distribution.

Continuing with the same example, the user device 106 and/or server 110 may determine whether one or more parameters of the user's recent (e.g., current) physiological data deviates from one or more of the corresponding healthy baseline values/ranges (e.g., identify a satisfaction of one or more deviation criteria). In some cases, identification of the satisfaction of deviation criteria may be performed by a machine learning classifier. A deviation from one or more of the healthy baseline values/ranges may indicate that a user may transition from the healthy state to an unhealthy state. For example, the user device 106 may determine that the user's temperature readings deviate from the determined healthy baseline temperature range, and that the user's HRV readings deviate from the determined healthy baseline HRV range. By way of another example, the user device 106 may determine whether temperature data in the early detection window deviates from one or more of the healthy temperature baseline values/ranges.

Subsequently, the user device 106 and/or server 110 may determine whether there may be a transition from the healthy state to the unhealthy state based on healthy to unhealthy transition criteria (e.g., deviation criteria). The deviation criteria may indicate one or more deviations (e.g., temperature deviation criteria, HRV deviation criteria, respiratory rate deviation criteria) that, if satisfied, indicate that the user may be transitioning from the healthy state to the unhealthy state. Each healthy baseline value/range may be associated with one or more deviation criteria. In some implementations, a single deviation from a healthy baseline range/value may satisfy the deviation criteria. In some implementations, deviation criteria may require that multiple deviations occur within a given time interval for one or more physiological parameters, such as one or more HRV deviations, temperature deviations, one or more respiratory rate deviations, etc.

In cases where one or more deviation criteria are satisfied, the user device 106 may notify the user that a transition from a healthy to unhealthy state has been detected/predicted. For example, the wearable application 250 may notify the user in the application GUI 275 or on the user device 106 in another manner (e.g., a push notification). As another example, if the server 110 makes the determination, the server 110 may notify the user via the web-based GUI 275 or another manner (e.g., a push notification). In some implementations, the GUI 275 may present physiological data associated with the baseline data and/or deviation (e.g., in a dashboard). In some implementations, the GUI 275 may provide summary values that summarize the deviations and/or determinations (e.g., summary prediction values). In some implementations, the GUI 275 may provide textual notifications to the user that indicate why there is a prediction that the user may transition to an unhealthy state in the near future.

In some implementations, the user device 106 and/or server 110 may report one or more risk and/or prediction values to the user (e.g., illness risk value, illness prediction value). The risk/prediction values, other physiological data/values, and techniques described herein may be used for a variety of purposes in addition to illness detection/prediction. For example, the data/values may be used for diagnosis, prognostic prediction (e.g., who is likely to require hospitalization or respiratory assistance), risk stratification (e.g., who is most at risk), resource allocation decision making (e.g., who should be tested for COVID-19 and how often individuals should be tested), precision medicine (e.g., what treatment works best for whom), monitoring of therapeutic efficacy (e.g., is a given treatment resulting in day-to-day improvement), urgent care triaging, pharmacodynamics/response purposes, and other purposes. Such digital biomarkers may be highly impactful for patients with suspected COVID-19 or influenza-like illnesses in order to prevent the spread of illness, facilitate return-to-work, conduct early identification in pre-symptomatic or asymptomatic individuals, and potentially identify early prognostic biomarkers of subsequent exacerbation likelihood.

In some implementations, the system 200 may be configured to provide some information or other insights regarding determined illness assessment metrics (e.g., illness risk metrics, illness prediction metrics). Personalized insights may indicate aspects of collected physiological data which were used to generate the illness assessment scores. For example, in cases where a user does not experience high temperatures (e.g., no fever), but still exhibits a relatively high illness assessment score (e.g., high probability of illness), providing personalized insights may provide additional information which is driving the high illness assessment score. Moreover, providing personalized insights may drive greater user engagement. Further, personalized insights may provide answers to questions such as "what is driving my high illness assessment score?," "why do I have a high illness assessment score if my temperature is normal?," "why do I sometimes see big changes in my illness risk metric (e.g., health risk management (HRM) score) from one day to the next?," "why is my readiness score saying one thing, but my HRM score is saying something else?," and "I have asthma; is my score high because of my reparation rate, or is it picking up on something more?" In this regard, insights may explain contributing factors to the illness assessment scores without exposing raw physiological data, user privacy, or details of the algorithms/models used to generate the illness assessment score.

For example, the user device 106 may display, via the GUI 275, one or more parameters of collected physiological data which are key contributors to the generated illness assessment score. For instance, if a high illness assessment score was determined primarily due to high temperature readings, the GUI 275 may indicate that a change in temperature is the primary reason for the high illness assessment score. By way of another example, if a user exhibits an increased respiratory rate and an elevated resting heart rate, but no increase in temperature, the GUI 275 may indicate that respiratory rate and resting heart rate are the primary reasons for the high illness assessment score. In other cases, insights may show trends of all or top contributors over time for a given user.

In some implementations, the system 200 may be configured to receive user inputs regarding detected/predicted illness in order to train classifiers (e.g., supervised learning for a machine learning classifier) and improve illness detection techniques. For example, the user device 106 may display an illness risk metric indicating a relative likelihood that the user will become ill. Subsequently, the user may input one or more user inputs, such as an onset of symptoms, a positive illness test, and the like. These user inputs may then be input into the classifier to train the classifier. In other words, the user inputs may be used to validate, or confirm, the determined illness risk metrics.

Although much of the present disclosure is described in the context of determining/predicting transitions from healthy to unhealthy states based on acquired physiological data (e.g., HRV data, temperature data), aspects of the present disclosure may also be used to determine/predict transitions from unhealthy to healthy states based on acquired physiological data. For example, the user device 106 and/or server 110 may detect transitions based on temperature biomarkers along with other physiological parameters (e.g., pulse waveform data, respiratory rate data, heart rate data, HRV data, actigraphy data, galvanic skin response data, oxygen saturation data) in order to determine/predict when a user will (or currently is) transitioning from an unhealthy state to a healthy state. Similar notifications and alerts may be provided to the user (e.g., via the GUI 275) indicating detected transitions.

Similar techniques using baseline temperature ranges for respective users may be used to determine/predict illness for the user in the pre-symptomatic stage. For example, the ring 104 may acquire physiological data (e.g., temperature data) from a user over a first time interval (e.g., reference window). The temperature data may include a skin temperature that is measured on the user's finger. The temperature data may be sampled at a sampling rate (e.g., one sample/minute, etc.), or temperature collection periodicity. In some implementations, the temperature data may be sampled continuously throughout the day and night. Although a skin temperature measured at the finger may be used, other temperature measurements (e.g., skin and/or core temperature) may be acquired from different user locations. The ring 104 may transmit the acquired/determined data to the user device 106 or other computing device (e.g., server 110). Similarly, the user device 106 may transmit the acquired physiological data to the server 110. The user device 106 and/or server 110 may acquire one or more days of temperature data for the user. Additionally, the user device 106 and/or server 110 may continue to acquire user temperature data over time from the ring 104 (e.g., via the user device 106).

In some implementations, the user device 106 and/or server 110 may filter the received temperature data. For example, the server 110 may apply a low pass filter to the temperature data. In some implementations, the user device 106 and/or server 110 may implement one or more transforms when processing the temperature data. For example, the server 110 may implement a discrete wavelet transform (DWT) in combination with a low pass filter. Filtering the temperature data may reduce the amount of noise and some extreme fluctuations in the temperature data. For example, the initial filtering/processing of the temperature data may remove spurious anomalies, which may enable the respective devices of the system 200 to more clearly identify bona fide anomalies/patterns that may be more indicative of early illness onset. Moreover, the ring 104, user device 106, server 110, or other computing device, may implement processing that removes false data readings. For example, temperature or other physiological readings associated with a large amount of activity (e.g., as indicated by a motion sensor) may be removed from the data, or otherwise mathematically adjusted for by the algorithm. Additionally, temperatures that are not indicative of user temperature, such as a hot shower, may be removed or mathematically adjusted. Removal of false or unreliable data may help ensure more reliable predictions.

Subsequently, the user device 106 and/or the servers 110 may determine baseline temperature data associated with the user based on the temperature data collected throughout the first time interval (e.g., reference window). Baseline temperature data may include linear statistical metrics of temperature data (e.g., minimum/maximum/mean/median temperature readings), as well as dynamic descriptions of temperature readings, such as temperature periodicities, frequency content (e.g., frequency composition, baseline frequency content), stability of frequencies over time (e.g., stability of temperature readings with respect to menstrual periods, ultradian rhythms, circadian rhythms), or any combination thereof, and relation of these dynamics to those of other physiological variables.

In some aspects, the user device 106 and/or server 110 may receive additional temperature data collected by the ring 104 throughout a second time interval (e.g., prediction window). In this example, the user device 106 and/or servers 110 may compare the additional temperature data to the baseline temperature data to identify whether one or more deviation criteria are satisfied. For instance, the server 110 may input the baseline temperature data and the additional temperature data into a classifier, where the classifier is configured to identify the satisfaction (or lack thereof) of one or more deviation criteria. In some cases, the classifier may compare temperature data to baseline temperature data to determine whether a deviation or change between the temperature data and the baseline temperature data satisfies (e.g., is greater than or equal to) some temperature change threshold. In other words, the classifier may identify a satisfaction of a deviation criteria if a change between a temperature reading/range relative to the user's baseline temperature readings/ranges exceeds a temperature change threshold.

The system 200 may then inform the user of detected/predicted illness based on the satisfaction of the deviation criteria. For example, the user device 106 may display, via the GUI 275, an indication of an illness risk metric, where the illness risk metric is associated with a relative probability that the user will transition from a healthy state to an unhealthy state.

In some cases, the user device 106 and/or server 110 may identify the satisfaction of deviation criteria (e.g., predict illness) based on deviations between high and/or low daytime temperature readings (e.g., maximum and/or minimum daytime temperature readings) between the baseline temperature data and the additional temperature data. For example, a change between a user's typical high daytime temperature readings between the baseline temperature data and the additional temperature data which satisfies a temperature change threshold (e.g., change greater than or equal to some threshold) may be indicative of illness. By way of another example, a change between a user's typical low daytime temperature readings between the baseline temperature data and the additional temperature data which satisfies a temperature change threshold (e.g., change greater than or equal to some threshold) may be indicative of illness. In some cases, a user may deviate in both high and low temperatures prior to onset of symptoms. Furthermore, although large deviations in temperature may be indicative of the onset of illness, in some implementations, smaller deviations may also be indicative of the onset of illness. Moreover, determining/predicting illness based on a user's own reference temperature data may provide a level of personalized detection that may not be afforded by other illness detection techniques, such as techniques that rely on absolute temperature value increases over a typical generic temperature threshold (e.g., 37° C.).

In some implementations, frequency content of temperature data may also be used to predict illness. For example, the user device 106 and/or server 110 may receive temperature data from the ring 104, and may determine frequency domain physiological data (e.g., frequency domain temperature data). For example, the user device 106 may determine one or more ranges of frequency content over one or more time periods (e.g., night/day). The user device 106 and/or server 110 may input the calculated frequency domain physiological data values into one or more models/classifiers. The one or more models/classifiers may include any machine learning model, machine learning classifier, or other algorithm known in the art (e.g., Random Forest classifier, gradient boosted classification tree, neural network algorithm).

In some implementations, frequency domain features may be approximated by peak-finding algorithms tuned to similar frequency ranges. These peak (or trough)-finding features may quantify the prominence of the peaks, the number of peaks, the distance between neighboring peaks, and the width of the peaks. Such approximations of frequency domain features may allow algorithms to function in real-time production environments, while capturing the rhythmic patterns of normal circadian and ultradian rhythms, and the disruption in these rhythms that illness may cause. One example of this approximation may be to approximate the circadian 22-26 hour rhythm in temperature by including daily features quantifying daytime minimum temperature values and nighttime maximum temperature values. In combination, such features may effectively capture illness-induced changes in the prominence or amplitude of the 22-26 hour circadian rhythm.

Continuing with the same example, the user device 106 and/or server may determine healthy temperature baseline values/ranges based on the frequency domain temperature data. For example, the user device 106 may determine healthy temperature baseline values/ranges based on temperature data in the temperature baseline determination window. By way of another example, the user device 106 may determine healthy temperature baseline values/ranges based on the frequency domain temperature data in the 22-26 hour range corresponding to the user's circadian rhythm.

The user device 106 and/or server 110 may determine whether a user's recent (e.g., current) temperature data deviates from one or more of the healthy temperature baseline values/ranges. For example, the user device 106 may determine whether the low frequency signal strength deviates from the healthy range during the second time interval (e.g., prediction window). By way of another example, the user device 106 may determine whether the low frequency signal strength for specific time durations within the user's natural circadian rhythm deviates from a healthy baseline relative to corresponding time durations of the circadian rhythm during the first time interval (e.g., reference window).

The user device 106 and/or server 110 may then determine whether there may be a transition from the healthy state to the unhealthy state based on the deviation criteria (e.g., healthy/unhealthy transition criteria). The deviation criteria may include one or more temperature deviation criteria, such as deviations in the frequency domain and/or time domain temperature signals. In other words, the user device 106 and/or server may then determine whether the output from one or more models (e.g., machine learning classifiers) indicates that the user is transitioning from a healthy state to an unhealthy state based on the frequency domain features of the temperature data.

It is noted herein that the frequency domain temperature data may yield insight into a user's health state that may not be visually apparent in the time domain data. For example, the time domain temperature data may not necessarily show a fever or other temperature change while the frequency domain may provide relevant information as to the user's health state and possible transition using the techniques described herein. Moreover, while techniques described herein may analyze data in accordance with a 22-26 hour range which approximately corresponds to a circadian rhythm. Further, ranges other than time ranges which correspond to the circadian rhythm may be used. For example, frequency domain content associated with the 8-12 hour range (e.g., ultradian rhythms), 2-5 hour range (e.g., ultradian rhythms), and/or the 1-2 hour range (e.g., sleep-related rhythms) may be used. Other ranges than those described herein may also be used in analyzing temperature deviations and detecting/predicting a user's transition between healthy/unhealthy states.

In some implementations, frequency analysis of temperature data may be illustrated as a heat map or spectrogram. For example, a spectrogram may graphically illustrate the frequency content of the temperature vs. time signal (e.g., illustrate low frequency content to high frequency content of acquired temperature data over time). A spectrogram of frequency domain temperature data may illustrate deviations in low frequency signal strength (e.g., a deviation in a range of low frequency signal power), and may be generated/calculated using a variety of techniques. For example, a spectrogram data may be calculated using continuous wavelet transform (CWT) techniques, Fourier transform techniques (e.g., fast Fourier transform), or other techniques.

The y-axis of a spectrogram of frequency domain temperature data may indicate units of period length in hours (e.g., where period=1/frequency). Stated another way, the y-axis may represent the frequency content of the signal in terms of period length (e.g., in hours). In some cases, a spectrogram of frequency domain temperature data may illustrate a high signal strength corresponding to an approximate circadian rhythm (e.g., in the 22-26 hour period range, centered around 24 hours), which may indicate that the user is transitioning from a healthy state to an unhealthy state, as described above. In some implementations, the user device 106 and/or server 110 may detect/predict a transition to the unhealthy state according to one or more deviation criteria with respect to the low frequency signal strength corresponding to the user's approximate circadian rhythm (e.g., patterns in low frequency signal strength in the 22-26 hour range).

In some aspects, other "rhythm parameters" of acquired temperature data (in addition to frequency content of temperature data) may be used to identify/predict illness. In general, frequency content is only one component of a user's natural physiological/biological rhythms (e.g., circadian rhythm, ultradian rhythm, etc.). Other rhythm-derived parameters (or rhythm-evaluated parameters) associated with physiological rhythms may include amplitude, stability, phase, and the like.

Deviation criteria (e.g., healthy/unhealthy transition criteria) may include one or more of the deviations and transition criteria described herein, including deviations in low frequency signal strength (e.g., a deviation in a range of low frequency power/signal strength). The deviation criteria may be satisfied when a user's frequency domain temperature data deviates outside of a healthy range of low frequency signal strength (e.g., based on baseline temperature data). In some implementations, healthy ranges of frequency domain temperature data may be defined for each respective user in terms of a range of values above and below a central healthy low frequency signal strength. For example, a healthy range may be defined as approximately one standard deviation about the center of the range, as determined based on the baseline temperature data. As another example, the healthy range may be defined as approximately two standard deviations about the center of the range.

In additional or alternative implementations, deviation criteria may be satisfied when a user's low frequency signal strength within a second time interval is outside the healthy range (determined based on the baseline temperature data) for some threshold period of time. For example, a transition from a healthy state to an unhealthy state may be detected/predicted in response to a deviation above or below the healthy range that lasts for greater than a threshold period of time. In some implementations, deviation/transition criteria may include a magnitude condition. For example, a transition from a healthy to an unhealthy state may be detected/predicted in response to a deviation above or below the healthy range by a threshold magnitude.

In some implementations, deviation criteria (e.g., transition criteria) may include a number of required deviations from the healthy range. For example, a transition from a healthy state to an unhealthy state may be detected/predicted in response to a threshold number of satisfied deviation criteria (e.g., two or more). In some implementations, a deviation may be required to last a threshold period of time and/or have a threshold magnitude in order to satisfy a deviation criteria. In some implementations, deviation criteria may include a number of deviation polarities. For example, a transition from a healthy state to an unhealthy state may be detected/predicted in response to a detection of a low deviation followed by a high deviation. Deviation criteria may include one or more deviations for any of the physiological parameters, such as temperature, respiratory rate, heart rate, and HRV. In some implementations, the deviation criteria may be based on deviations in the time domain, the frequency domain, or both.

In some implementations, a transition from a healthy state to an unhealthy state may be detected/predicted in response to the presence of a threshold number of deviation criteria being satisfied, such as satisfaction of a temperature deviation criterion and one or more other deviation criteria. In some implementations, deviation criteria may include a composite determination in which multiple different deviation criteria are taken into account. For example, different weights may be assigned to different deviations (e.g., heavier weighting to stronger deviation criteria), and a transition from a healthy state to an unhealthy state may be detected/predicted if the sum of the different weighted criteria is greater than a threshold value. In some implementations, deviation criteria may require satisfaction of a defined sequence of indicators, such as satisfaction of a temperature criterion followed by another transition criterion.

It has been found that low frequency signal strength of temperature data may deviate from a healthy baseline range prior to onset of the flu and fever. The deviation of the low frequency signal strength outside of the healthy baseline range may indicate that the user may enter the unhealthy state. Additionally, the low frequency signal strength may return to a healthy, baseline range prior to recovery. The re-entry of the low frequency signal strength to the healthy range may indicate that the user may re-enter a healthy state.

As described herein, the ring 104 (or other device) may acquire user temperature data (e.g., skin temperature data) throughout the day and night. The frequency domain analysis techniques described herein may use any combination of day and/or night data for detection/prediction of a user's transition between healthy/unhealthy states. For example, in some implementations, the computing devices (e.g., ring 104, user device 106, server 110) may perform frequency domain analysis on nighttime data, such as successive nights of nighttime data (e.g., while a user is sleeping). As another example, in some implementations, the computing devices may perform frequency domain analysis on data throughout the day and night, such that the data includes successive days of data while the user alternates between waking hours and sleeping hours. In still other examples, the computing devices may perform frequency domain analysis on daytime data, such that the data includes successive days of data acquired while the user is awake/active.

The frequency domain analysis techniques described herein may monitor deviations in one or more frequency ranges for one or more different sets of data, such as one or more signal deviations in frequency ranges associated with nighttime data, daytime data, and/or complete day data (e.g., continuous 24 hour data). For example, a computing device may detect/predict a user's transition based on deviations within a single frequency range associated with nighttime data (e.g., successive nights of data). As another example, a computing device may detect/predict a user's transition based on deviations within multiple frequency ranges associated with nighttime data. As another example, a computing device may detect/predict a user's transition based on deviations within one or more nighttime frequency ranges and within one or more daytime frequency ranges. In some implementations, a computing device (e.g., user device 106, server 110) may use rules to detect/predict when a user is transitioning between healthy/unhealthy states. For example, the rule(s) may indicate that a transition may occur based on specified deviations in one or more frequency bands for one or more sets of data.

In some implementations, a computing device (e.g., user device 106, server 110) may use one or more models to detect/predict when a user is transitioning between healthy/unhealthy states. A model may use any of the spectrogram data described herein as input. For example, a model may use any of the baseline values and deviation values as input. In a specific example, a model may use baseline and deviation values associated with one or more frequency bands in one or more different data sets (e.g., nighttime, daytime, all day). A model may also receive inputs associated with other user physiological parameters (e.g., heart rate, HRV, respiration rate, etc.). The inputs may be formatted in a variety of ways, depending on the model. For example, the inputs may include decimal values and/or binary values (e.g., deviation yes/no) that are based on frequency spectrogram data.

In some implementations, a model may output a value (e.g., a decimal value from 0-1) indicating a likelihood that a user is transitioning between states. The user device 106 and/or server 110 may compare the model output value to a threshold value to determine whether a transition to an unhealthy state is likely. In some implementations, the various components of the system 200 (e.g., ring 104, user device 106, server 110) may implement one or more machine learned models (e.g., a supervised learning model) configured to receive inputs and generate the output values.

In some implementations, the components of the system 200 (e.g., user device 106, server 110) may select time intervals (e.g., first time interval/reference window, second time interval/prediction window) which will be used for illness detection. In particular, the system 200 may select/identify different time intervals (e.g., different windows) such that physiological data acquired during each of the respective time intervals may be compared to each other. By comparing physiological data acquired during the different time intervals, the system 200 may determine whether deviation criteria are satisfied between the physiological data acquired during the respective time intervals (e.g., deviations which satisfy some threshold), where satisfaction of the deviation criteria may be indicative of illness.

For example, the user device 106 and/or server 110 may select a reference window and a prediction window for acquired physiological data (e.g., temperature data, HRV data, etc.). In some aspects, the user device 106 and/or server 110 may define a reference window and a subsequent prediction window for the acquired physiological data. Physiological data acquired during the reference window (e.g., first time interval) may be used to determine baseline physiological data (e.g., baseline temperature data, baseline HRV data, etc.). Comparatively, physiological data acquired during the prediction window (e.g., second time interval) may be compared against the baseline physiological data to determine whether deviation criteria between the respective time intervals are satisfied. In some cases, the prediction window may include the most recently acquired temperature data (e.g., the latest 1-5 days of temperature data).

In some implementations, the reference window and the prediction window may be defined in increments of a day. For example, the reference window may include one or more days of physiological data (e.g., a week of temperature data). Similarly, a prediction window may include one or more days of temperature data (e.g., employing an auto-regressive strategy for feature specification within that prediction window). The size of the reference window and the prediction window may vary, depending on the amount of available physiological data. For example, when a minimum amount of physiological data is available, the reference window and the prediction window may have a minimum size, or may draw from prior knowledge of demographically/medically similar users. In a specific example, if the server 110 operates on a minimum of two days of physiological data and currently has two days of user physiological data, the server 110 may select the reference window as a single day of data, and then select the prediction window as the subsequent day of data. Using a minimum amount of available data may allow the server 110 to detect transitions between healthy and unhealthy states earlier than in a case where the server 110 waits to acquire a larger data set for calculations.

As the user device 106 and/or server 110 acquires more physiological data from the ring 104, the user device 106 and/or server 110 may lengthen the reference window and/or the prediction window. For example, the server 110 may lengthen the reference window in order to establish a more robust set of physiological data for analysis. In a specific example, acquiring a third day of data may cause the reference window to expand to the first two days of data. In this specific example, the prediction window may occupy the most current day of data (e.g., the third day of data). The server 110 may lengthen the reference window and the prediction window to any length. In some implementations, the server 110 may require that physiological data for a day includes a minimum portion of valid data (e.g., within meaningful temperature thresholds) throughout the day (e.g., for 90% or more of the day). Although each of the windows may include one or more days of data, reference windows and prediction windows may be implemented that include other durations of physiological data.

The reference window and the prediction window used for illness detection may exhibit any length (e.g., quantity of hours, days, etc.). In some cases, the reference window may include seven days of data, whereas the prediction window may include two days of data (e.g., two most recent days of data). The reference window and the prediction window may be rolling windows that move over time. For example, the windows may move in one day increments, or other increments. In some implementations, the windows may be moved in one day increments, such that the prediction calculations are performed by the morning (e.g., a user's waking time) so that the user can be provided with a prediction before the day begins (e.g., before work).

Although a single prediction window may be defined, in some implementations, the user device 106 and/or server 110 may define multiple prediction windows. For example, the multiple prediction windows may occur sequentially after the reference window. Each of the multiple prediction windows may include one or more days of data. In some implementations, the server 110 may initially extend the reference window as new data is received. After extension of the reference window to a desired length (e.g., seven days), the server may add one or more additional prediction windows for each day of additional physiological data.

Although the user device 106 and/or server 110 may use a reference window and a prediction window, in some implementations, aspects of the present disclosure may detect a user's transition between healthy and unhealthy states based on a prediction window without using a reference window. For example, the server 110 may use data from one or more other users (e.g., users with similar demographics, similar physiological data, etc.) to determine whether the user is transitioning between healthy and unhealthy states. The server 110 may use only a prediction window in cases where there is not enough available data to form a reference window. For example, if only a single current day of physiological data is available, the server 110 may use the first day as a prediction window. Subsequently, the server 110 may acquire additional data (e.g., an additional day) and define both a reference window and a prediction window. If a reference window is unavailable, the server 110 may select detection/prediction parameters (e.g., scoring features) based on other users that are similar (e.g., similar age, sex, underlying conditions, etc.).

In some aspects, the user device 106 and/or server 110 may generate a physiological parameter distribution or histogram (e.g., temperature distribution, HRV distribution, etc.) for each window (e.g., reference window, prediction window). For example, in the context of temperature data, the distributions may indicate the number of temperature values that fall within specified probabilistic ranges. For instance, for a seven-day reference window, the distribution may indicate the number of temperature values during the seven-day window that fall within specified ranges. As another example, for a multi-day prediction window, the distribution may indicate the number of temperature values during the multi-day window that fall within the specified ranges. In implementations where multiple windows are used, a distribution may be made for each of the reference and/or prediction windows. For example, first and second windows may have corresponding first and second reference/prediction window distributions.

The user device 106 and/or server 110 may determine one or more physiological parameter distribution values (e.g., temperature distribution values, HRV distribution values) for each of the distributions. The distribution values may be values that indicate how temperature and other signal values are distributed within the windows. For example, the distribution values for a window may indicate the central tendency, dispersion, kurtosis, and skew of the values within that window.

The user device 106 and/or server 110 may determine one or more distributions for each window. In some implementations, each distribution may be associated with a threshold value that defines the minimum or maximum value associated with the distribution value, and/or non-parametric quantiles of a distribution on the low (e.g., 0.001, 0.01) and high (e.g., 0.95, 0.975, 0.99) ends of the spectrum. For example, with respect to a high temperature deviation, the distribution value may be determined using a high percentile temperature value. In this example, temperature values above this high percentile temperature value may be defined as high temperature deviations. Put another way, any temperature above this high-threshold temperature value may be considered as a high temperature deviation or anomaly. With respect to a low temperature deviation, the distribution value may be determined using a low percentile temperature value. In this example, temperature values below the minimum temperature value may be defined as low temperature deviations. Put another way, any temperature below the minimum temperature threshold value may be defined as a low temperature deviation or potentially an anomaly.

The threshold values may be defined in a variety of ways. In some implementations, the threshold values may be defined based on the values included in the distributions for the windows. For example, the threshold values may be defined as upper/lower quantiles of the distribution. In a specific example, a threshold value for a high temperature deviation may be defined as a temperature that is greater than 95% of the temperatures in the distribution. In another specific example, a threshold value for a low temperature deviation may be defined as a temperature that is less than the smallest 5% of temperatures in the distribution. In some implementations, the distribution and/or threshold values may be determined in other manners. For example, the distribution values and/or threshold values may be determined based on the maximum/minimum temperatures in the distribution, range of temperatures in the distribution, mean/median temperatures in the distribution, and/or based on other factors associated with the distribution. The distribution values may also be determined using other processing techniques.

In some instances, the distributions in question may be multivariate. For example, given the inherent physiological relationship between activity (or MET units) and temperature, the server may assess anomalies or change relative to a multivariate distribution. Similarly, the distributions of heart rate, HRV, respiration rate and temperature may be understood within a multivariate context. The coherence, or lack thereof, across some signals and their multivariate time series at some times of day (e.g., at sleep onset) may provide useful features for prediction, detection, or prognostic algorithms.

The user device 106 and/or server 110 may calculate one or more distribution values for each window. In some implementations, the user device 106 and/or server 110 may calculate a single distribution value for both windows. For example, the server 110 may determine a high temperature distribution value for both windows. The high temperature distribution value may indicate a percentage of temperature values that are greater than a threshold value. With respect to the reference window, the server 110 may calculate a high temperature distribution value by first determining a number of temperature values that are greater than a threshold value. The server 110 may then divide the number of temperature values that are greater than the threshold value by the number of temperature values in the reference window.

The server 110 may determine the high temperature distribution value in the prediction window in a similar manner as in the reference window. In some implementations, the server 110 may use values from the reference window to define the threshold used in the prediction window. For example, the server 110 may use the threshold value (e.g., temperature threshold value) from the reference window as the threshold value in calculations for the prediction window.

In some implementations the comparison across reference and prediction windows may incorporate a reference window that is derived from multiple timescales. For example, human behavior may change markedly on a seven-day cycle due to weekday-weekend changes, resulting in marked physiological changes, whereas human hormone cycles change on an approximately monthly basis (particularly among women), also resulting in changes in physiology and skin temperature specifically. External temperatures may change over a yearly cycle, and thereby may influence observed skin temperature anomalies in daily life. Hence, an appropriate reference window may incorporate a set of weighted inputs from different informational scales, or weigh a given current distribution against multiple prior reference distributions, measured across various behaviorally and biologically relevant timescales.

In some implementations, the user device 106 and/or server 110 may determine multiple distribution values in each window. For example, the server 110 may determine multiple high temperature (or multivariate temperature/activity) distribution values in each window. As another example, the server 110 may determine multiple low temperature distribution values in each window. As another example, the server 110 may determine one or more distribution values for high and low temperatures in the windows. In a specific example, the server 110 may determine high temperature distribution values for threshold quantiles of 0.999, 0.995, and 0.975. The server 110 may also determine low temperature distribution values for threshold quantiles of 0.025, 0.01, and 0.001. In implementations where multiple high/low temperature distribution values are determined, some temperature values above multiple thresholds may be counted twice (e.g., once for each distribution value calculation). Alternatively, the distribution values may be calculated based on a number of temperature values between the thresholds. In some iterations, this comparison of a reference and early detection/prediction window may be computed using the Kullback-Leibler (KL) divergence method, or direct density ratio estimation.

In some aspects, the user device 106 and/or server 110 may analyze the distribution of physiological data (e.g., temperature values, HRV values) in the prediction window compared to the reference window, in order to determine whether the physiological data (e.g., univariate or multivariate distribution values) deviate in the prediction window relative to the reference window. In other words, the user device 106 and/or server 110 may compare physiological data collected within the respective windows to identify a satisfaction (or lack thereof) of deviation criteria, which may be used to identify illness.

For example, the server 110 may determine relative distribution values (e.g., relative distribution ratios) that indicate an amount of deviation between temperature values in the prediction window and the reference window. In one example, the server 110 may determine a relative distribution value by dividing a distribution value in the prediction window by the corresponding distribution value in the reference window. In examples where each window has multiple distribution values, the server 110 may determine a relative distribution value for each of the pairs of multiple distribution values.

The magnitude of a relative distribution value (e.g., a relative risk ratio) may indicate an amount of deviation from the reference window to the prediction window. With respect to high temperature deviations, a greater percentage of high temperature values in the prediction window relative to the reference window may yield a larger relative distribution value for high temperatures. With respect to low temperature deviations, a greater percentage of low temperature values in the prediction window relative to the reference window may yield a larger relative distribution value for low temperatures. As such, larger relative distribution values may indicate greater deviations in high/low temperatures between the windows. In some implementations, the server 110 may determine whether a user is transitioning from the healthy state to the unhealthy state based on the relative distribution values. For example, the server 110 may include one or more thresholds/models that use the relative distribution values to determine whether a user is transitioning.

Peaks in relative distributions values within the respective windows may be used to identify illness. The occurrence of peaks (e.g., 0.999 threshold, 0.975 threshold, 0.005 threshold, 0.001 threshold) in the relative distribution values may indicate the onset of illness. For example, the number of peaks and/or the values of the peaks over time may be indicative of the onset of illness. The server 110 may determine whether the user is transitioning from the healthy state to the unhealthy state based on the number of peaks, value of the peaks, arrangement of the peaks, and additional data described herein.

Subsequently, the user device 106 and/or server 110 may determine whether a user is transitioning from a healthy state to an unhealthy state based on analysis of the physiological data distributions (e.g., temperature distributions) in the prediction window and the reference window. For example, the user device 106 and/or server 110 may determine whether a user is transitioning from a healthy state to an unhealthy state based on one or more deviations in temperature values, as represented by the determined relative distribution values. In some aspects, user device 106 and/or server 110 may determine deviations in distributions (e.g., temperature distributions) between the early prediction window and the reference window, and may determine whether the user is transitioning to an unhealthy state based on the determined deviations (e.g., satisfaction of deviation criteria). In some implementations, the user device 106 and/or server 110 may implement a classifier or other machine learned model to make the state transition determinations.

In some implementations, the server 110 may output an illness risk metric or illness prediction metric that indicates a relative probability that the user will transition from a healthy state to an unhealthy state. For example, the server 110 may determine the illness prediction metric based on one or more of the calculated relative distribution values. In some implementations, the server 110 may generate a single prediction value, or multiple prediction values associated with one or more meanings described herein. In some implementations, the prediction value may be a decimal value, which may have a variety of meanings, depending on how the server 110 is configured. In other implementations, the prediction value may be a binary value, such as a 0 or 1 value, which may have a variety of meanings. In some implementations, an illness prediction metric may indicate a likelihood of illness. For example, a decimal value may indicate a probability that the user is transitioning to an unhealthy state. As another example, a binary value of 1 may indicate that a user is transitioning to an unhealthy state. In this example, a binary value of 0 may indicate that a user is in the healthy state and is not likely transitioning.

The user device 106 and/or server 110 may determine the illness risk metric (e.g., illness prediction metric) in a variety of different ways. The meaning of the prediction value may depend on how the prediction value is calculated. In some implementations, the server 110 may use a function (e.g., an equation) that receives the relative distribution values and calculates the prediction value based on the relative distribution values. In some implementations, the function may include weightings that are applied to the different relative distribution values. In some implementations, the server 110 may use rule-based calculations to calculate the prediction value. Example rules may define the prediction value based on a number of relative distribution values above/below a threshold, the magnitude of the relative distribution values, the timing of the spikes in relative distribution values, or any other data related to magnitude/timing/arrangement of the relative distribution values and/or other distribution parameters.

In some implementations, the user device 106 and/or server 110 may use a machine learned model (e.g., a supervised learning model) to determine the illness risk metrics (e.g., illness prediction metrics). A model used to determine the prediction value may be referred to herein as an "early detection/prediction model" or a "prediction model." The prediction model may be trained on training data. The training data may include data from a set of users that is labeled according to when the users developed symptoms of an illness. In some implementations, the prediction model may receive the relative distribution values as input. The prediction model may generate one or more illness prediction values based on the received input. The interpretation of the prediction value(s) may depend on how the model is generated. In some implementations, as described herein, the illness risk metric output by the model may indicate a likelihood of illness if the model is trained using data labeled according to symptom onset.

In some implementations, the user device 106 and/or server 110 may implement autoregressive features (e.g., in modeling). For example, the server 110 may define multiple prediction windows. In implementations where the server 110 defines multiple prediction windows, the server 110 may calculate relative distribution values for each prediction window. In these implementations, the server 110 may generate one or more prediction values based on the relative distribution values for each prediction window. For example, if a prediction model takes relative distribution values as input, the model may receive twice as many inputs in the case that two prediction windows are used instead of a single prediction window. Using multiple prediction windows may more closely model illnesses that behave differently in terms of the incubation period, period of viral replication, or expected number of days until symptom onset. For example, the use of multiple separate days of prediction windows may capture the incubation of an illness better than a single larger prediction window. In some implementations, autoregressive components may detect phasic transitions, defined by multiple overshoots at the daily or circadian rhythm frequency, which are overlaid on top of a multi-day baseline increasing slope, approaching the day of symptom onset, and reflecting a set-point change in thermoregulation associated with febrile states and/or pyrogenic mediator and/or other sterile or pathogen-associated immune stimuli (DAMPs and PAMPs), with the theoretical potential to impact thermoregulation.

In some implementations, the system 200 may leverage location information associated with a respective user (e.g., a geographical position of the user) to further improve illness detection techniques for the user. The body's ability to maintain internal temperatures within a comfortable range (e.g., not too hot, not too cold) is critical for healthy functioning. Changes in environmental temperatures (e.g., ambient temperatures) are one of the major factors that our bodies must continually adjust to, therefore requiring tuning of our body's "thermostat" settings, or how the body dynamically increases and decreases body temperature throughout the day in response to various perturbations (e.g., infection, exercise-induced heating, going outside and experiencing acute changes in temperature, etc.).

Users who live at more extreme latitudes (e.g., closer to the poles) experience colder climates with greater seasonal variation in light. Hence, users in higher latitudes must adjust to greater extremes of cold and light. For example, in Helsinki, Finland (latitude~60° N), the average monthly temperature may range from approximately −7° C. to 21° C., and average hours of daylight may range from approximately 6 to 19 hours. Comparatively, in Crete, Greece, (latitude~35° N), the average monthly temperature may range from approximately 12° C. to 30° C., and the average hours of daylight may range from approximately 10 to 14.5 hours. Light exposure is an important regulator for the daily circadian rhythms of temperature.

Exposure to hot or cold climates affect distal skin temperature, particularly during the day, which may result in "ceiling" and "floor" effects that affect illness detection. For example, on average, a ninety-nine percentile (99% ile) of skin temperature readings for a first user living in a colder climate may be slightly cooler as compared to a ninety-nine percentile of skin temperature readings for a second user living in a warmer climate. This difference may make illness-induced increases in ninety-nine percentile of skin temperature readings more evident for users living in colder climates. In contrast, in warmer climates, the effect of the external environment on transient elevations in ninety-nine percentile skin temperature readings may add more "noise" or partially mask the effects of illness. As such, when a bigger temperature gradient exists between internal body temperature and ambient temperature (such as in colder climates), wearable devices (e.g., ring 104) may have an advantage in detecting subtle increases in temperature and heart rate, or decreases in HRV, due to the vasoconstriction response used to prevent excess heat loss and facilitate a core temperature increase.

Stated differently, deviations in temperature may be more evident for users living in colder climates as compared to users living in warmer climates. As such, deviations in skin temperature may be more indicative of illness (e.g., have higher predictive value) for users in colder climates as compared to deviations in skin temperature for users in warmer climates. This concept will be further shown and described with reference to FIGS. 6 and 7.

Figure 6:
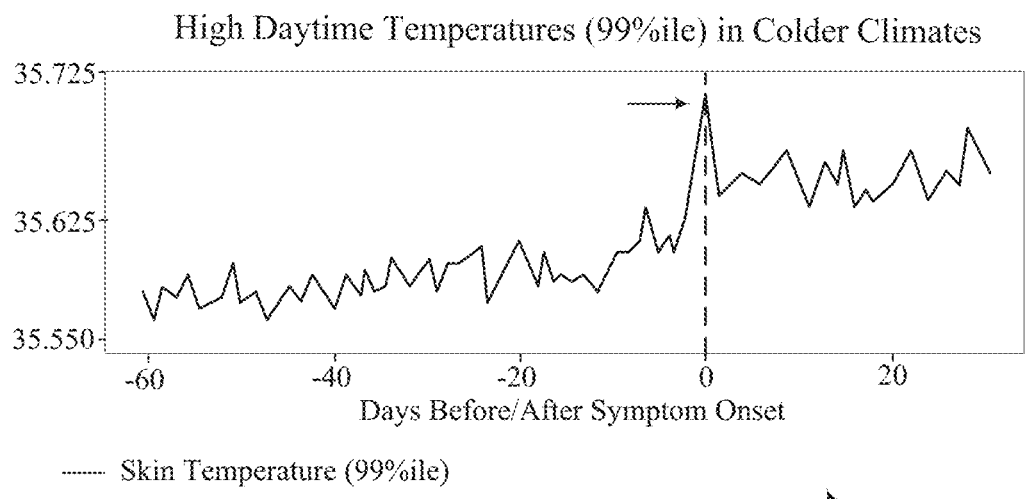
FIG. 6 illustrates an example of a temperature data diagram that supports illness detection techniques in accordance with aspects of the present disclosure.
Figure 6:
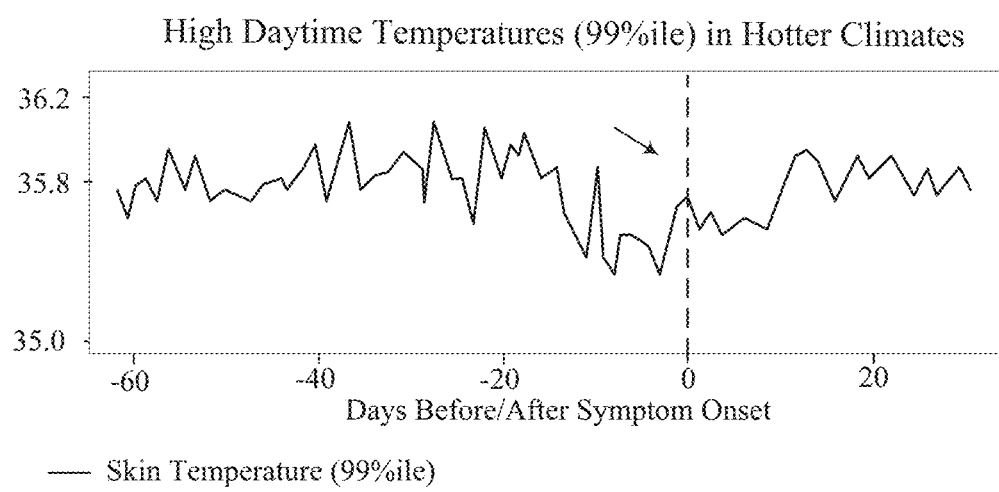

FIG. 6 illustrates an example of a temperature data diagram 600 that supports illness detection techniques in accordance with aspects of the present disclosure. In particular, the temperature data diagram 600 includes a first diagram 605-a which illustrates high daytime temperature readings/ranges for users in colder climates, and a second diagram 605-b which illustrates high daytime temperature readings/ranges for users in warmer climates.

The x-axis of the diagrams 605-a and 605-b illustrates time (e.g., days) before and after symptom onset, with time=0 indicating symptom onset (e.g., first development of symptoms) for users in colder climates (e.g., higher latitude; 55° N) and warmer climates (e.g., lower latitude; 35° N), respectively. Illness onset at time=0 in the diagrams 605-a and 605-b may encompass a variety of respiratory or influenza-like illnesses, including COVID-19, flu, and other illnesses with similar symptoms. The y-axis of the diagrams 605-a and 605-b illustrates high daytime temperatures (in degrees Celsius) for users in colder climates and warmer climates, respectively. Specifically, the y-axis of the diagrams 605-a and 605-b illustrate a ninety-nine percentile (99% ile) of temperature readings for users during the daytime, which may be considered to be a maximum daytime temperature for the respective users, after filtering for outliers.

As shown in diagram 605-a illustrating high daytime temperatures readings/ranges for users in high latitudes (e.g., near Finland) and/or colder climates, the maximum daytime temperature measured via a wearable device may increase in the days and weeks leading up to symptom onset. Due to the fact that skin temperature at the peripheral (e.g., hands, fingers) during the daytime tends to be lower in colder climates, it may be easier to detect the body's attempt to increase core temperature by vasoconstricting at the periphery. This may also be particularly apparent during the daytime, as opposed to during sleep, because skin temperature and core temperature are less correlated and more counter-regulatory during the daytime.

Comparatively, referring to diagram 605-b illustrating high daytime temperature readings/ranges for users in lower latitudes (e.g., southern portion of the United States) and/or warmer climates, users may exhibit a less pronounced increase in high daytime temperatures leading up to illness onset as compared to users in colder climates. In other words, for users in warmer climates, illness may not definitively manifest as an increase in daytime maximum temperatures. Taken together, it has been found that users in colder climates may experience more pronounced increases in high daytime temperatures as compared to users in warmer climates.

Figure 7:
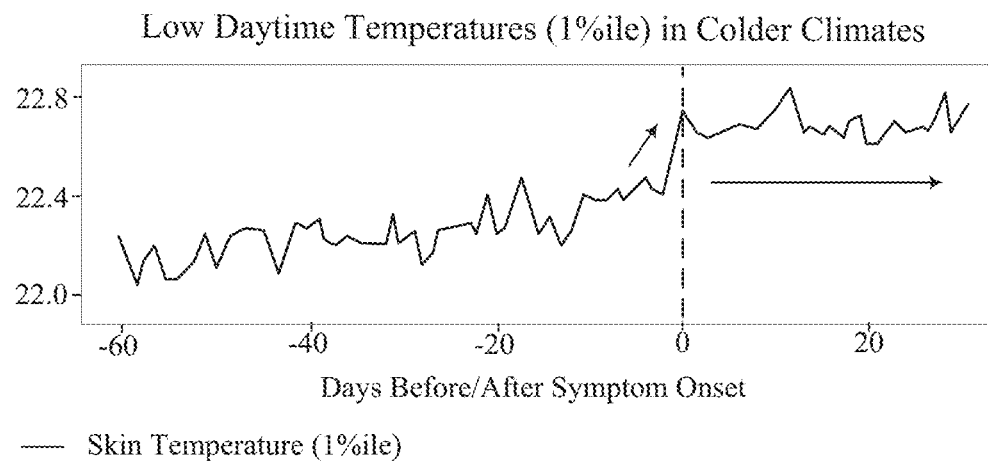
FIG. 7 illustrates an example of a temperature data diagram that supports illness detection techniques in accordance with aspects of the present disclosure.
Figure 7:
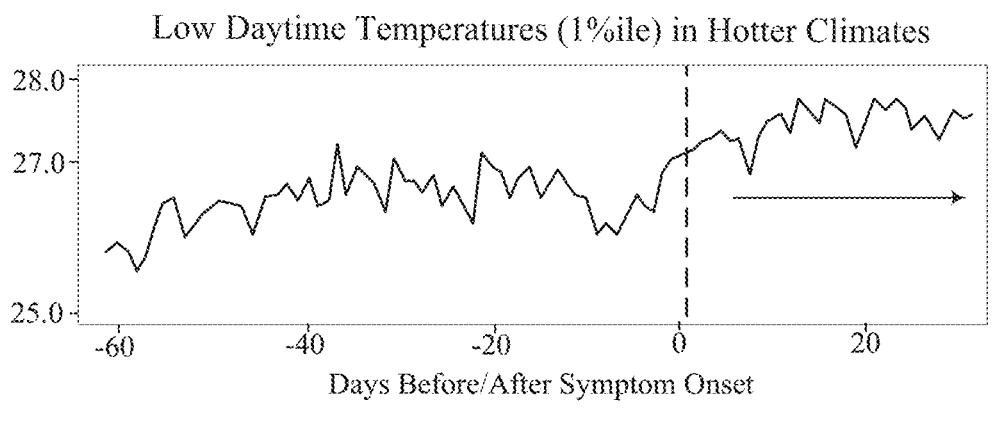

FIG. 7 illustrates an example of a temperature data diagram 700 that supports illness detection techniques in accordance with aspects of the present disclosure. In particular, the temperature data diagram 700 includes a first diagram 705-a which illustrates low daytime temperature readings for users in colder climates, and a second diagram 705-b which illustrates low daytime temperature readings for users in warmer climates.

The x-axis of the diagrams 705-a and 705-b illustrates time (e.g., days) before and after symptom onset, with time=0 indicating symptom onset (e.g., first development of symptoms) for users in colder climates (e.g., higher latitude; 55° N) and warmer climates (e.g., lower latitude; 35° N), respectively. Illness onset at time=0 in the diagrams 705-a and 705-b may encompasses a variety of respiratory or influenza-like illnesses, including COVID-19, flu, and other illnesses with similar symptoms. The y-axis of the diagrams 705-a and 705-b illustrates low daytime temperatures (in degrees Celsius) for users in colder climates and warmer climates, respectively. Specifically, the y-axis of the diagrams 705-a and 705-b illustrate a one percentile (1% ile) of temperature readings for users during the daytime, which may be considered to be a minimum daytime temperature for the respective users, after filtering for outliers. It is noted herein that the absolute values of the y-axes differ substantially across the first diagram 705-a (22-23° C.) as compared to the second diagram 705-b (25-28° C.).

Infection/illness may drive an increase in core body temperatures. One way for the body to accomplish this increase may be to conserve heat by preventing heat loss through the shell of the body. The skin accomplishes this in part by vasoconstricting (narrowing the small blood vessels at the surface of the skin). This vasoconstriction may be most evident as an increase in the lowest daytime temperature values, as shown in FIG. 7. This phenomenon may be identified and/or featurized for various machine learning algorithms as the 1% ile of a distribution of daytime temperatures taken from one day for a user compared to a prior day or baseline period for that same user.

For example, as shown in diagrams 705-a and 705-b, 1% ile daytime temperature readings/ranges may be elevated for users during periods of sickness regardless of latitude or climate. Further, a comparison of diagram 705-a and diagram 705-b illustrates that users living in colder climates may experience larger increases in daytime low temperature readings/ranges in the days and weeks leading up to illness onset (e.g., larger pre-symptomatic increases in low daytime temperatures for users in colder climates).

Accordingly, in some implementations, the system 200 may utilize location information and other factors (e.g., latitude, season, environmental exposures) to improve illness prediction techniques described herein. For example, an algorithm or machine learning classifier may include a user's latitude or longitude, the month of the year, or utilize a seasonally-corrected time series to render the resultant temperature signal "stationary" with respect to climate-related changes. An algorithm/classifier, such as a tree-based algorithm or other machine learning model, may learn to model the interactions between exposure and environmental factors and an individual user's unique physiologic time series. In some cases, a classifier may combine multiple signals sensitive to environment, climate, and seasonality effects in order to improve the signal-to-noise ratio, in order to better detect illness. Moreover, a classifier may be configured to predict illness differently for pools of users grouped based on certain similar characteristics, which could include location, climate, and environmental exposure factors.

Stated differently, latitude and/or other location information may serve as a crude proxy for the general range of local temperatures, especially when taken together with time-based features like the season or month of year. These features may act as "moderators," or factors, that influence a relative predictive value of statistical daytime temperature readings for predicting illness. These moderators may determine the conditions under which a given daytime temperature feature is particularly useful as a predictor of illness or not. In some implementations, the system 200 may use more complicated weather and regional information, combined with a user's geolocation from their user device 106, to derive more precise estimates of environmental exposures, and identify when individuals are inside or outside. Such location information may be used to determine a relative predictive accuracy of temperature data for identifying illness.

For example, the user device 106 and/or server 110 of the system 100 may receive temperature data associated with a user which was acquired by the ring 104. The user device 106 and/or server 110 may additionally receive/identify location information associated with the user. The location information may include a geographical position of the user, a latitude of the user, or both. In some cases, the user device 106 and/or server 110 may receive the location information for the user based on a user input received via the GUI 275. For instance, the user may input their home address or approximate home location within the wearable application 250. Additionally, or alternatively, the user device 106 and/or server 110 may determine the location information based on global positioning modules of the user device 106 (e.g., Global Positioning Satellite (GPS) module, Global Navigation Satellite System (GNSS) module), or any combination thereof.

In this example, the user device 106 and/or server 110 may input the temperature data and the location data into a machine learning classifier, where the machine learning classifier is configured to identify a satisfaction of one or more deviation criteria of the temperature data (e.g., deviations in temperature readings from baseline temperature data for the user) based on the location information.

In particular, the location information may be used by the machine learning classifier to identify/generate one or more "predictive weights" associated with acquired temperature data. The predictive weights may be associated with a relative predictive accuracy for detecting illness. For instance, as shown and described in FIGS. 6 and 7, users in colder climates may experience more significant temperature changes leading up to illness onset as compared to users in warmer climates. As such, temperature changes (and temperature readings) for users in colder climates may have a higher relative "predictive weight" as compared to temperature changes/temperature readings for users in warmer climates. In some cases, the location data may be used to determine a geographical position and/or climate data for the user (e.g., ambient temperature data), which may be used to generate the predictive weights. Ambient temperature data may be based on data acquired from the user device 106, the time of year, climate data for the determined geographical position, or any combination thereof.

As such, in some cases, the machine learning classifier may allocate relatively higher predictive weights for temperature data collected from users in colder climates, and relatively lower predictive weights for temperature data collected from users in warmer climates. Subsequently, upon identifying predictive weights for temperature data collected from a user, a machine learning classifier may "weight" collected temperature data based on (e.g., using) the predictive weights to generate weighted temperature data. The weighted temperature data may then be used by the machine learning classifier to identify a satisfaction of deviation criteria and predict illness.

By determining location information for users and determining predictive weights for temperature data based on the location information (and/or ambient temperature data), techniques described herein may be configured to compensate for skin temperature responses between users in varying climates. In other words, location information (e.g., latitude) may be used as a rough proxy for external climate/ambient temperature, which may be used to determine a relative predictive accuracy of temperature data for identifying illness. As such, techniques described herein may support more accurate and efficient illness detection techniques on an international scale.

Location may also affect seasonal changes, which manifest in the biological rhythm parameters (e.g., day length, which may be impacted by latitude throughout a calendar year, may impact circadian rhythm parameters of temperature). In this way, location information may be used in some aspects to weight or modify classifications of "healthy" and "unhealthy" time intervals where seasonality or seasonal phase is a factor.

Further, in some aspects, individual or group illness detection thresholds or classifiers may be modified if information about illness rates are available in the location of a user. For example, if flu case rates are substantially elevated in Miami, and location information for the user indicates that the user is located in Miami, then the detection thresholds might be lowered to reflect the increased local risk.

In additional or alternative implementations, in lieu of generating predictive weights for temperature data, the system 200 may simply input both temperature data and location information into a classifier, and may allow the classifier to learn which combinations of temperature data and location information are predictive of illness. In other words, the system 200 may input temperature data and the location information into a classifier (e.g., machine learning classifier), and may train the classifier to determine/predict illness based on received temperature data and location information. In such cases, the classifier may be trained to recognize that temperature changes across users may exhibit varying predictive accuracy when predicting illness depending on the relative location (and/or climate/ambient temperature) of each respective user.

In some implementations, the system 200 may additionally or alternatively use data associated with modifiable behavioral predictors, such as sleep and activity, to perform illness detection. Scientific evidence has shown that healthy behaviors, such as being more active or getting better sleep, can minimize the risk of becoming ill with an influenza-like illness (including COVID-19) and can even modify the strength of the antibody response. However, conventional wearable devices have not effectively identified metrics associated with sleep and activity which may be collected via the wearable device to detect illness in the pre-symptomatic stage.

Some aspects of a predictive algorithm/classifier used to identify illness, such as a user's age, gender, physiology, or pre-existing medical conditions, are generally not under the user's control to change. Comparatively, activity and sleep are both health behaviors that users can modify ("modifiable behavioral predictors"). Moreover, these modifiable behavioral predictors may exhibit changes as a user becomes ill. As such, techniques described herein may utilize data collected via the ring 104 related to modifiable behavioral predictors in order to further refine illness detection techniques during the pre-symptomatic state. Modifiable behavioral predictors which may be used to perform illness detection may include, but are not limited to, daytime activity, sleep duration, and timing of sleep (e.g., bedtime, wake time), adherence associated with wearing the ring 104 (e.g., frequency/consistency with which a user wears the ring 104), and the like.

An important behavioral sign of sickness is the feeling of getting tired more easily and not having the energy to exercise as much. This feeling of fatigue is caused by inflammatory proteins (e.g., cytokines), which are secreted by the immune system upon recognition of virally infected cells. These inflammatory cytokines signal the brain to conserve energy, which the brain accomplishes by modifying our behavior to reduce our energy expenditure.

In some aspects, the ring 104 may be configured to measure activity (e.g., movement) using actigraphy sensors and/or accelerometers. The ring 104, user device 106, and/or server 110 may be configured to convert actigraphy data and/or other data associated with activity (e.g., accelerometer data) and convert these data streams into an estimation of METs, a measure of the energy expended during an activity. This may be further shown and described with reference to FIG. 8.

Figure 8:
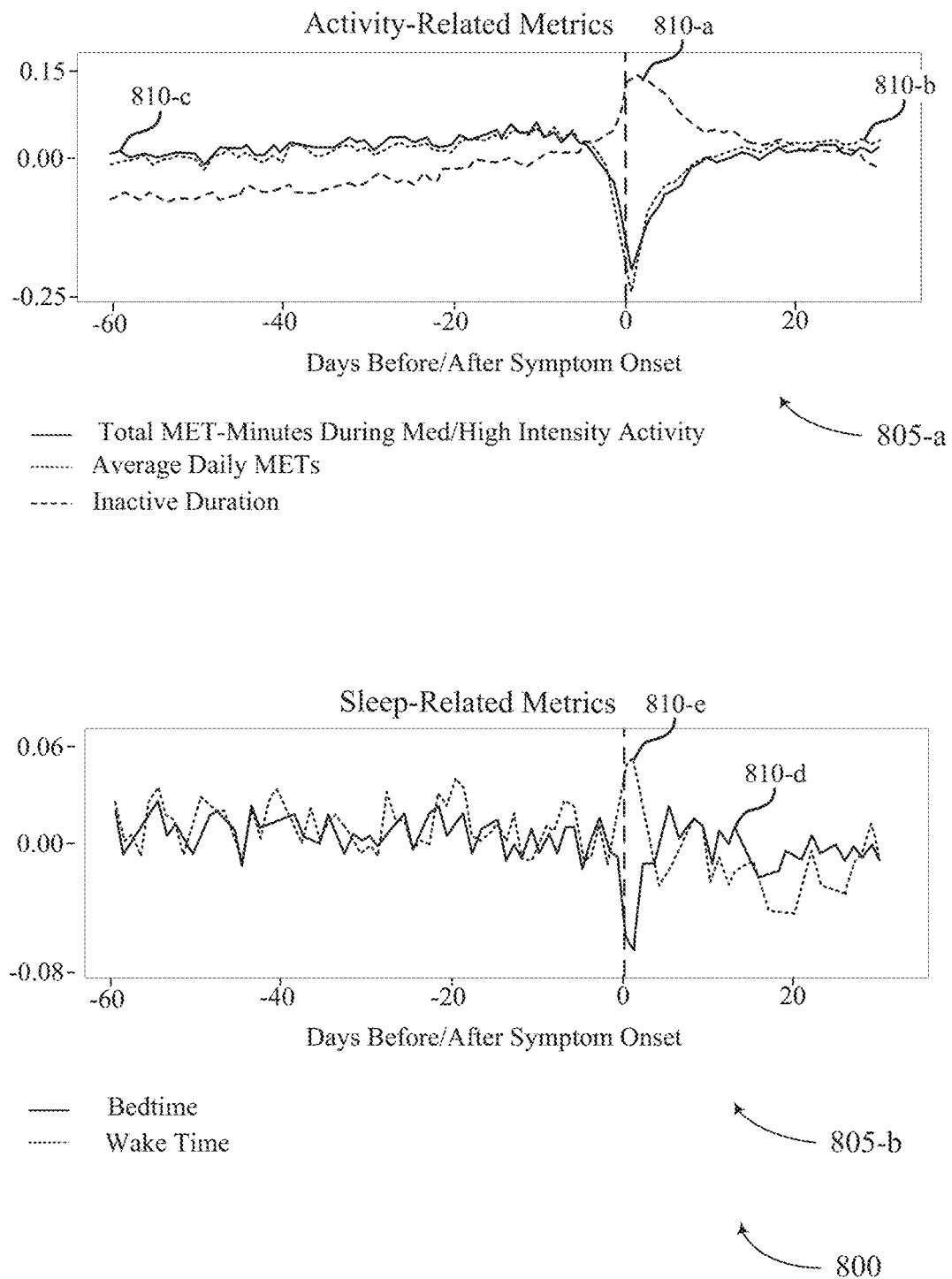
FIG. 8 illustrates an example of a modifiable behavioral predictor diagram that supports illness detection techniques in accordance with aspects of the present disclosure.

FIG. 8 illustrates an example of a modifiable behavioral predictor diagram 800 that supports illness detection techniques in accordance with aspects of the present disclosure. In particular, the modifiable behavioral predictor diagram 800 includes a first diagram 805-a which illustrates three activity-related metrics (normalized for comparison) in the days before and after symptom onset, and a second diagram 805-b which illustrates sleep-timing related metrics (e.g., bedtime, wake time) in the days before and after symptom onset.

The x-axis of the diagrams 805-a and 805-b illustrates time (e.g., days) before and after symptom onset, with time=0 indicating symptom onset (e.g., first development of symptoms) for users. The y-axis of the diagram 805-a is z-normalized to illustrate relative increases and decreases in activity-related metrics over time within the same graph. The y-axis of the diagram 805-b illustrates changes in bedtimes and wake times in normalized units.

Referring to diagram 805-a illustrated in FIG. 8, curve 810-a illustrates daily inactivity durations of users over time, curve 810-b illustrates average daily METs (e.g., energy expenditure) for users over time, and curve 810-c illustrates total MET minutes accumulated during medium or high intensity activity over time. As may be seen in diagram 805-a, users tend to become more inactive in the days prior to symptom onset (e.g., increase in curve 810-a prior to illness onset). Moreover, average daily METs (energy expenditure) decreases (e.g., decrease in curve 810-b), and the total-MET minutes accumulated during medium or high intensity activity drops (e.g., decrease in curve 810-c) in the days prior to symptom onset. While all three curves 810-a, 810-b, and 810-c may exhibit the most significant changes following symptom onset, there are accelerating predictive changes in the direction of reduced activity just before symptom onset. As such, in some implementations, the system 200 may utilize these characteristics/parameters (e.g., inactivity, average daily METs, total METs accumulated during activity) in order to predict illness.

While reduced activity (decrease in curve 810-a) or reduced daily average METs (decrease in curve 810-b) may be helpful metrics for illness detection, these changes can be subtle, and activity can change for many reasons other than illness. Moreover, metrics based on activity or METs may be less meaningful than raw or absolute numbers, and more meaningful when built to detect a decline relative to a person's usual activity level. Hence, in some implementations, the respective components of the system 200 (e.g., ring 104, user device 106, server 110) may be configured to determine a user's average daily METs as a change relative to the same user's prior median daily METs across a representative prior baseline (e.g., fourteen days). In other words, the system 200 may compare activity and/or daily METs from a second time interval (e.g., prediction window prior to symptom onset) to activity and/or daily METs determined from a prior first time interval (e.g., reference window) in order to determine changes in the user's expected activity and/or daily METs. In this regard, changes in activity and daily METs between different time intervals (e.g., change in daily METs relative to a user's baseline daily METs) may be used to identify a satisfaction of deviation criteria and predict illness onset.

In some implementations, the system 200 may utilize a given user's raw absolute average daily METs score as a feature for illness detection, while also including a rolling mean of the daily METs average score over the prior thirty days (which may be equally weighted or given decreasing weights progressively backwards in time). The inclusion of both these features as an input to a machine learning classifier/algorithm for illness detection may enable the machine learning classifier to learn a within-user normalization strategy. In other words, by providing historical activity and daily MET value for a user into a machine learning classifier, the machine learning classifier may be able to determine recent changes in activity/daily METs relative to that user's typical level of activity/daily METs over some reference time interval (e.g., over the past month).

Furthermore, exercise strengthens the immune system, making users who are highly active less vulnerable to infection/illness. As such, using rolling mean features for activity and daily METs over some reference window (e.g., past month) may enable a machine learning classifier to identify individuals with "stronger" immune systems who are less likely to become sick.

In some implementations, the system 200 may additionally or alternatively include a standard deviation of average daily METs over some reference window (e.g., past month) as a feature input within the machine learning classifier to improve illness detection. Standard deviation of average daily METs may capture how consistently a user engaged in high levels of activity. Comparatively, a mean (e.g., average) can be large if an individual engages in a lot of exercise one day a week. However, optimal immune system effects may be associated with a more consistent regimen of exercise. Accordingly, including both the mean and the standard deviation of activity over a representative window of time (e.g., past month) may allow the machine learning classifier to learn whether highly active users and those who are consistently active are less likely to become sick.

Further, a "decline" in average METs due to illness may not be detectable for users who are not active to begin with. In other words, for a user who is very inactive, it may be difficult to detect decreases in activity relative to the user's normal, low activity baseline. Hence, inclusion of features that capture a user's longer term "trait" or "reference" activity levels, the consistency of those levels, and also acute or "state" changes may be most useful when combined together in one model that can learn the interactions (e.g., a tree or neural network type of algorithm).

Figure 9:
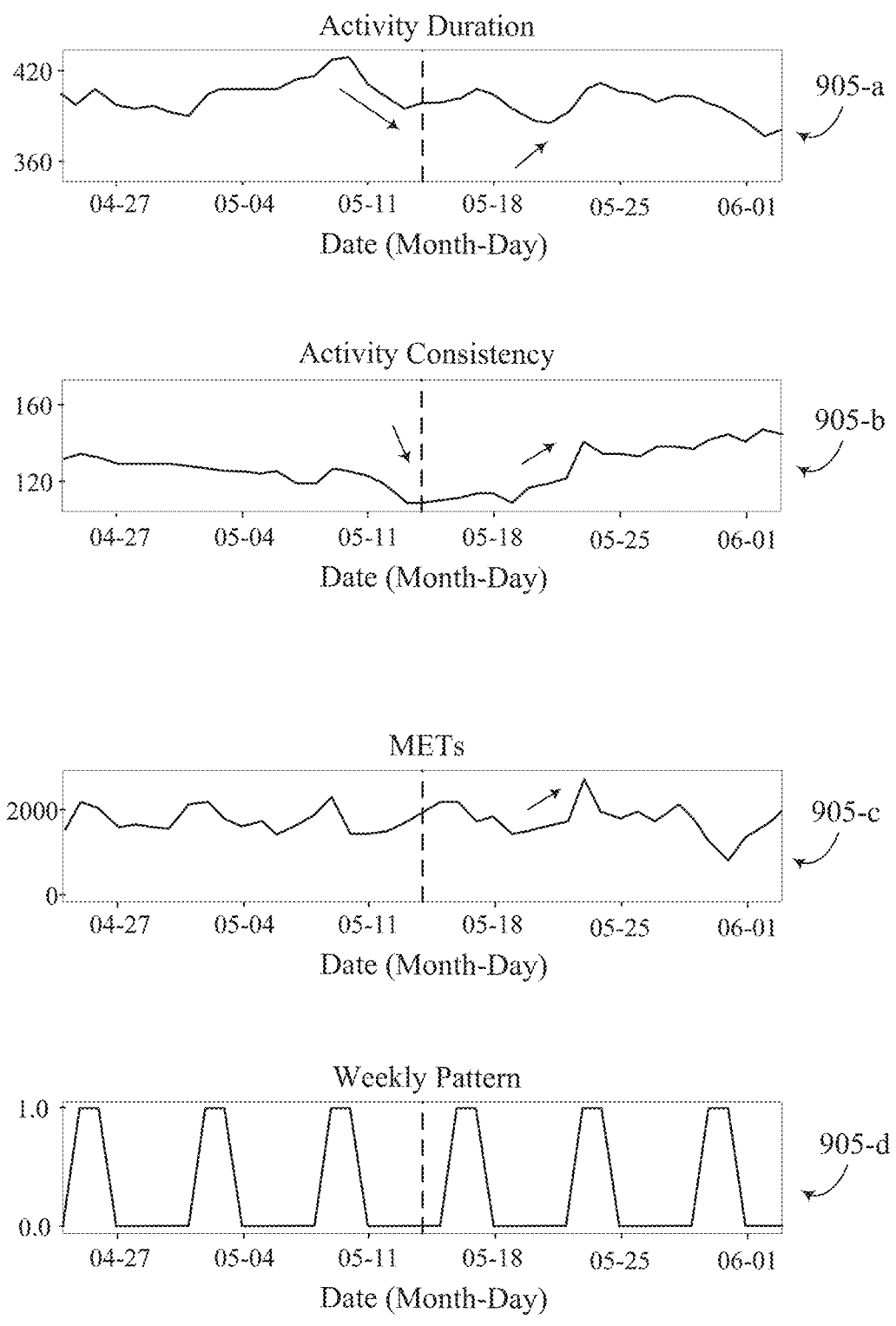
FIG. 9 illustrates an example of a modifiable behavioral predictor diagram that supports illness detection techniques in accordance with aspects of the present disclosure.

FIG. 9 illustrates an example of a modifiable behavioral predictor diagram 900 that supports illness detection techniques in accordance with aspects of the present disclosure. In particular, the modifiable behavioral predictor diagram 900 includes an activity duration diagram 905-*a*, an activity consistency diagram 905-*b*, a METs diagram 905-*c*, and a weekly pattern diagram 905-*d*.

The x-axis of the respective diagrams 905-*a* through 905-*d* illustrates a date (e.g., month-day) before and after symptom onset, where the reference line between May 11 (05-11) and May 18 (05-18) within each of the diagrams 905 illustrates the onset of respective illness symptoms (e.g., onset of dry/wet respiration, allergic reactions, gastrointestinal symptoms, fever symptoms, etc.) for the user. The y-axis of the activity duration diagram 905-*a* illustrates a rolling average of active durations (in minutes) over a thirty-day window. The y-axis of the activity consistency diagram 905-*b* illustrates a standard deviation of active durations (in minutes) over a thirty-day window (e.g., more or less activity consistency). The y-axis of the METs diagram 905-*c* exhibits METs expenditure (e.g., total performance in terms of effort) per day. Lastly, the y-axis of the weekly pattern diagram 905-*d* depicts a true/false indication as to whether a given day on the x-axis includes a weekend day (e.g., 0=weekday, 1=weekend). Generally, the weekly pattern diagram 905-*d* (e.g., weekly pattern adjustment model) may be used to adjust activity expectations for a user based on a cyclical weekly pattern, as a user's activity may generally be higher on weekends.

As may be seen in FIG. 9, a user may exhibit a decline in active durations (e.g., decline in activity duration diagram 905-*a*) as well as a decline in activity consistency (e.g., decline in activity consistency diagram 905-*b*) prior to symptom onset. These patterns in activity duration and activity consistency may generally take place at roughly the same time, and may therefore be used as features for identifying/predicting illness. Further, comparing the diagram 905 to the weekly pattern diagram 905-*d*, it may be seen that users generally exhibit higher activity on weekends as compared to weekdays. Lastly, increases in activity duration (e.g., increase in activity duration diagram 905-*a*), activity consistency (e.g., increase in activity consistency diagram 905-*b*), and METs expenditure (e.g., increase in METs diagram 905-*c*) several days after symptom onset may be indicative of the user returning from the unhealthy state to a healthy state (e.g., illness recovery).

Generally, the system 200 may input physiological data associated with the activity features illustrated in FIG. 9 (e.g., activity duration, activity consistency, METs) into a machine learning classifier such that the machine learning classifier may learn how to combine the multiple activity features and determine patterns that best describe each respective user in the pre-symptomatic period. Training a machine learning algorithm using data from each respective user may enable the machine learning classifier to identify each respective user's individualized response to illness, as each user may respond to illness differently. As such, the activity features illustrated in FIG. 9 may be used to identify/predict that a user will transition from an unhealthy state to a healthy state, or vice versa.

In general, activity metrics show "seasonality" or predictable patterns aligned with weekdays and weekends or certain days of the week. For example, as shown in FIG. 9, users may generally be more active on the weekends as compared to the weekdays. Similar cyclical patterns may be identified on a monthly basis, yearly basis, and the like. For example, users may generally be more active in warmer months as compared to colder months. This could be either an effect of warmer weather and less rain/snow or an effect of the pandemic lockdowns changing activity lifestyles.

Accordingly, in some implementations, the system 200 may utilize one or more models (e.g., pattern adjustment models) which describe the relatively cyclical activity, behavior, or other physiological parameters with respect to some time interval. Models may include weekly activity models, yearly activity models, menstrual cycle models, and the like. By accounting for cyclical, predictable changes in activity or other physiological parameters, techniques described herein may be able to more effectively identify which changes in activity/physiological data are attributable to illness, and which changes are based on predictable cyclical user behavior (e.g., more active on weekends) and/or predictable physiological responses (e.g., monthly menstrual periods).

For example, in some cases, the components of the system 200 (e.g., user device, server 110) may generate a feature or model (e.g., weekly pattern adjustment model) which represents weekdays as "0" and weekends as "1" (e.g., weekly model: M—0, T—0, W—0, Th—0, F—0, S—1, Su—1) In this example, the weekly pattern adjustment model representing weekdays/weekends may be included with the activity features in a machine learning classifier or algorithm (e.g., tree algorithm, gradient boosting classification tree) to improve illness detection. In such cases, the machine learning classifier may construct or "learn" feature interactions to account for differences in user activity between weekends and weekdays to improve illness detection. For instance, by inputting a weekly pattern adjustment model into a machine learning classifier, the machine learning classifier may be configured to determine that a user is less active on weekdays, and may therefore be less likely to identify low activity metrics (e.g., low METs) on weekdays as being indicative of illness. In some cases, the features may be each day of the week, dummy coded as six different days of the week and one reference day.

In some implementations, the system 200 may apply a Seasonal Autoregressive Integrated Moving Average (SARIMA) model may be applied to a past time series of thirty days or more during which the user was known to be healthy.

The seasonal order parameter may be fixed to seven to capture the weekly seasonality. Such a model may be trained for each respective user, and output parameters reflecting the degree to which a given user exhibits a weekly pattern in activity. These personalized SARIMA coefficients, based on a rolling window over the past N days, may then be inputted as features for a larger machine learning classifier. Additionally, or alternatively, time series classification models may be used (e.g., Random Convolutional Kernel Transform (ROCKET) model or MiniROCKET model), which may inherently model the autoregressive or other time-dependent patterns.

In some cases, a user's adherence with wearing a wearable device may include an additional modifiable behavioral predictor when performing illness detection/analysis. Borrowing the term from the field of behavioral medicine, "adherence" may refer to whether or not users wear the ring 104, or how often they wear the ring (e.g., frequency/consistency with which a user wears the ring 104). It has been found that, in general, users wear the ring 104 more frequently when they become sick (e.g., increased adherence with illness). Moreover, increased adherence has been found to be indicative of recovery from illness for some users. Indeed, users generally exhibit increased adherence (e.g., more consistent wear time, decreased non-wear time) shortly after symptom onset and during recovery from illness. This could be due to increased interest in watching physiological data when users are sick, or due to the fact that users may be less likely to remove their ring 104 due to the illness or various activities.

In this regard, the term "adherence data" may refer to data associated with a frequency or consistency with which a user wears the ring 104. In some aspects, the ring 104 may determine whether the user is wearing the ring based on time durations during which the ring 104 is charging, via a presence (or absence) of detected user temperature readings, respiratory rate, heart rate data, and the like. In this regard, the ring 104 may determine and transmit "adherence data" to the user device 106 and/or server 110, which may be used to determine an adherence with which the user wears the ring 104. Moreover, adherence data (e.g., changes in adherence data) may be used by the system 200 to identify illness onset, recovery from illness, or both. For example, the user device 106 may identify a change in adherence data for a user (e.g., more frequent/consistent wearing of the ring 104, less frequent/consistent wearing of the ring 104). In this example, the user device 106 may determine illness risk metrics, predict illness onset/illness recovery, or any combination thereof, based on the changes in the adherence data.

Symptoms of fatigue may include another important behavioral sign of sickness. When the body senses an infection, the immune system signals the brain to direct energy toward fighting infection. Sleep-timing features for a machine learning algorithm could include falling asleep earlier than normal ("earlier bedtime"), falling asleep faster (lower "latency"), sleeping for a longer duration than one's usual sleep time, waking up later than normal, and the like. In some implementations, the illness detection classifiers/algorithms described herein may include absolute values in conjunction with features representing prior typical average or median values over a representative period of time, such as fourteen days. In other implementations, illness detection algorithms may represent the current day's metric as the difference between today's measurement and the median of the prior fourteen days (or a representative baseline of reasonable length). Such features may be inputted into a tree algorithm or neural network algorithm, with or without day of week or weekend/weekday binary features.

For example, reference will again be made to diagram 805-b illustrated in FIG. 8. The x-axis of the diagram 805-b illustrates time (e.g., days) before and after symptom onset, with time=0 indicating symptom onset (e.g., first development of symptoms) for users, whereas the y-axis of the diagram 805-b illustrates changes in bedtimes and wake times in normalized units. Curve 810-d illustrates a user's bedtime, quantified as the minutes since the prior midnight, and computed as the delta versus the user's median bedtime over a previous representative baseline period (e.g., prior 7-14 days). Similarly, curve 810-e illustrates a user's wake time, quantified as the minutes since the prior midnight, and computed as the delta versus the user's median wake time over a previous representative baseline period (e.g., prior 7-14 days).

As may be seen in diagram 805-b, users generally go to bed earlier (e.g., decrease in curve 810-d) and wake up later (e.g., increase in curve 810-e) prior to illness symptom onset. As such, in some implementations, the system 200 may determine sleep data for a user (e.g., bedtimes, wake times) to determine illness onset. In particular, changes in sleep data (e.g., changes in bedtimes and/or wake times) may be used to identify satisfaction (or lack thereof) of deviation criteria, which are subsequently used to identify/predict illness.

Not all users respond the same to illness. Moreover, viruses and infections may affect users in different ways. Hence, different users may exhibit different sleep patterns across a collection of sleep-timing variables in response to illness. Classifiers (e.g., machine learning classifiers, machine learning algorithms, tree-based algorithms), may be configured to auto-detect different sleep data patterns and thresholds across a panel of features, which may improve illness prediction techniques described herein. Moreover, by utilizing each user's own sleep data as reference data, classifiers may be trained on an individualized basis for each user, which may enable the classifiers to more accurately detect changes in sleep data for each respective user, and thereby predict illness based on sleep data for each respective user.

Figure 10:
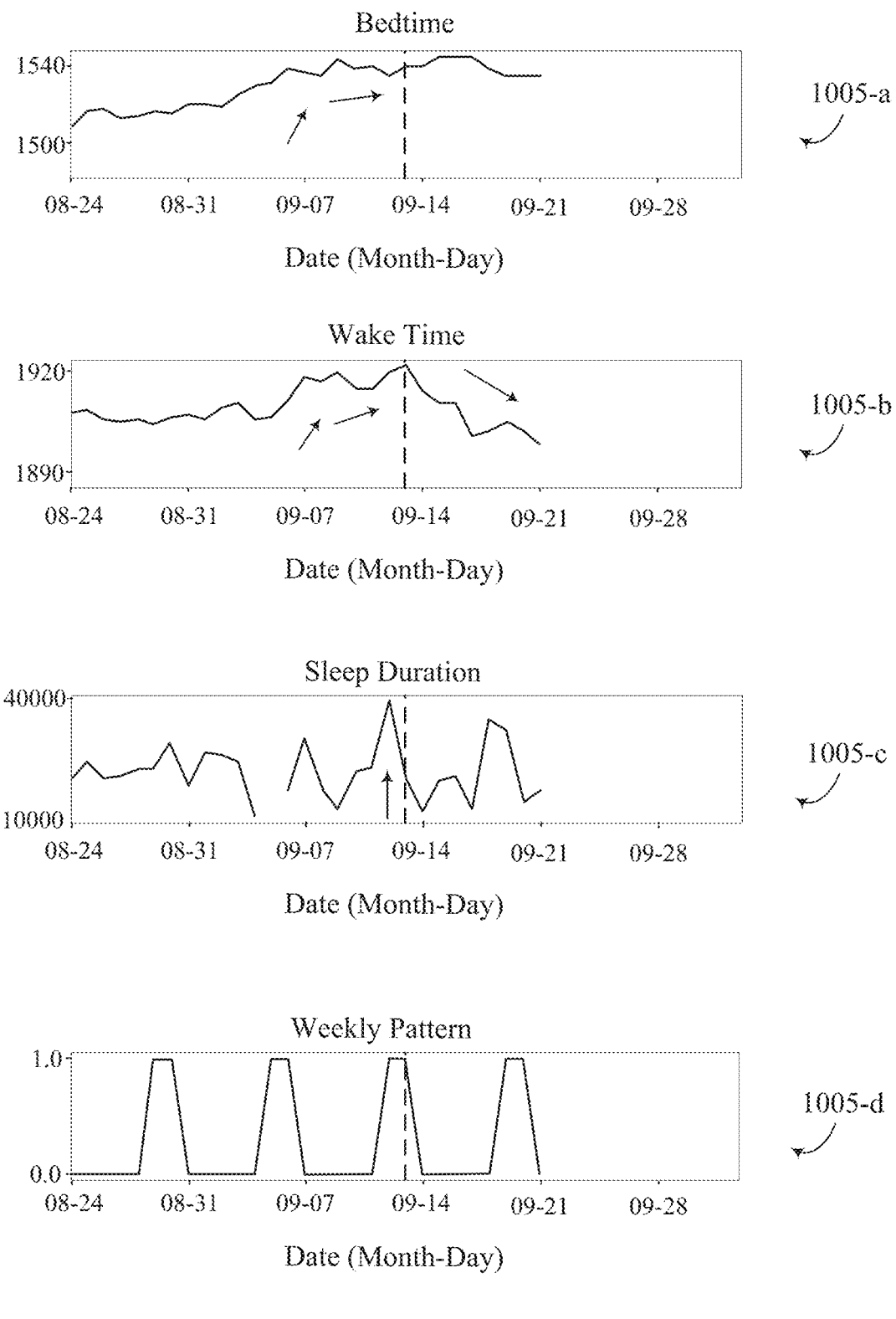
FIG. 10 illustrates an example of a modifiable behavioral predictor diagram that supports illness detection techniques in accordance with aspects of the present disclosure.

FIG. 10 illustrates an example of a modifiable behavioral predictor diagram 1000 that supports illness detection techniques in accordance with aspects of the present disclosure. In particular, the modifiable behavioral predictor diagram 1000 includes a bedtime diagram 1005-a, a wake time diagram 1005-b, a sleep duration diagram 1005-c, and a weekly pattern diagram 1005-d.

The x-axis of the respective diagrams 1005-a through 1005-d illustrates a date (e.g., month-day) before and after symptom onset, where a reference line between May 11 (05-11) and May 18 (05-18) within each of the diagrams 1005 illustrates the onset of respective illness symptoms (e.g., onset of dry/wet respiration, allergic reactions, gastrointestinal symptoms, fever symptoms, etc.) for the user. The y-axis of the bedtime diagram 1005-a illustrates a user's bedtime, quantified as the minutes since the prior midnight, and computed as a rolling average over a 30-day window. The y-axis of the wake time diagram 1005-b illustrates a user's wake time, quantified as the minutes since the prior midnight, and computed as a rolling average over a 30-day window. The y-axis of the sleep duration diagram 1005-c illustrates a duration of the user's sleep in seconds per night. Lastly, the y-axis of the weekly pattern diagram 1005-d depicts a true/false indication as to whether a given day on the x-axis includes a weekend day (e.g., 0=weekday, 1=weekend). Generally, the weekly pattern diagram 1005-*d* may be used to adjust sleep expectations for a user based on a cyclical weekly pattern. For example, users may generally be able to sleep more on weekends when they do not have to get up for work.

As may be seen in FIG. 9, it has been found that users may begin to go to bed earlier (e.g., increase in bedtime diagram 1005-*a*) and wake up later (e.g., increase in wake up diagram 1005-*b*) in the days leading up to symptom onset. Moreover, users may sleep longer (e.g., increase in sleep duration diagram 1005-*c*) in the days leading up to symptom onset. In this regard, these features of a user's sleep data (e.g., bedtimes, wake times, sleeping durations) may be input into a classifier (e.g., machine learning classifier) to identify deviation criteria which are used to predict illness onset.

A relative consistency of various parameters (e.g., consistency of bedtimes, consistency in wake times) may also be used to perform illness detection techniques described herein. In general, humans have consistent sleeping habits (e.g., users usually go to bed and wake up around a similar time from day to day). Consistent sleeping habits allows cells within the human body to be aligned with the environment and optimize energy efficiency by knowing the best times to mobilize energy into the bloodstream or fight infection. As such, consistent sleeping habits may help prevent illness.

Accordingly, sleep-timing parameters/features related to the "consistency" of a user's sleeping habits (e.g., bedtime and waketime) may be used to predict illness onset. Bedtime consistency and wake time consistency may be measured as a standard deviation over some reference time interval (e.g., previous thirty days) of the minutes since the prior midnight at which the individual went to sleep or woke up, respectively. In particular, it has been found that both bedtime and wake time become more inconsistent (or variable) in the days before symptom onset. This may be due to changes in behavior during an incubation period of the illness. As such, in some implementations, features/parameters associated with a consistency of sleep data (e.g., bedtime consistency, wake time consistency, sleep duration consistency) may be used for predicting or identifying illness, as described herein.

In some implementations, the system 200 may utilize one or more "pattern adjustment models" to improve illness detection techniques described herein. Pattern adjustment models may be used to account for predictable changes in a user's behavior, activity, sleeping patterns, and/or physiological data. In some implementations, pattern adjustment models may be used to account for repetitive, cyclical patterns. Pattern adjustment models may include weekly pattern adjustment models, seasonal pattern adjustment models, yearly pattern adjustment models, or any combination thereof.

For example, as described previously herein with respect to diagram 905-*d* in FIG. 9 and diagram 1005-*d* in FIG. 10, a weekly pattern adjustment model may include a series of "0s" and "1s" representing weekdays and weekends, respectively. In this example, the weekly pattern adjustment model may be used (e.g., input into a classifier) in order to account for changes in a user's sleeping patterns and/or activity patterns between weekdays and weekends. As such, by inputting the weekly pattern adjustment model into a classifier, the system 200 may be able to more effectively differentiate between changes in sleeping patterns/activity patterns which are indicative of oncoming illness, and changes which are attributable to normal, cyclical changes in behavior throughout the week.

Similarly, yearly pattern adjustment models and/or seasonal pattern adjustment models may help the system 200 differentiate between changes in sleeping patterns/activity patterns which are indicative of oncoming illness, and changes which are attributable to normal, cyclical changes in behavior throughout the year (e.g., users are typically less active during the winter months as compared to the summer months). In some implementations, the system 200 may generate pattern adjustment models for each respective user on a user-by-user basis. In particular, the system 200 may acquire physiological data for a user, and may generate pattern adjustment models for the user based on the acquired physiological data.

For instance, by collecting physiological data for a user throughout several weeks, the system 200 may determine that the user goes to bed later, gets up later, and is generally more active on weekends as compared to weekdays (which may be represented as a "user activeness metric"). In this regard, the system 200 may generate a weekly pattern adjustment model which captures this information. As such, by generating the weekly pattern adjustment model for the user, the system 200 may be able to more effectively differentiate between changes in the user's behavior (e.g., sleeping patterns, activity patterns) and/or physiological data which are attributable to illness, and which are simply attributable to the user's normal weekly routine. For instance, inputting the weekly pattern adjustment model into a classifier may reduce a likelihood that the classifier will interpret later bedtimes and later wake up times on weekends as being attributable to illness.

In some aspects, the pattern adjustment models may be used to generate "predictive weights" which may improve illness detection techniques described herein. As noted previously herein, predictive weights may refer to some weighting metric or other metric which are associated with a relative predictive accuracy for detecting illness. For instance, a higher predictive weight may be associated with higher relative accuracy for predicting illness (e.g., more accurate at identifying illness), whereas a lower predictive weight may be associated with a lower relative accuracy for predicting illness (e.g., less accurate at identifying illness).

For example, a user may generally go to bed later, get up later, and may be more active on weekends as compared to weekdays. In this example, sleep data which indicates later bedtimes and later wake up times on the weekends may be associated with lower "predictive weights," in that these parameters may be more likely to be attributable to the user's normal weekly sleeping habits rather than being indicative of illness. In this regard, the system 200 may utilize determined pattern adjustment models (e.g., weekly pattern adjustment models, seasonal pattern adjustment models, yearly pattern adjustment models) to generate one or more "predictive weights" for physiological data, sleep data, activity data, and the like, where the predictive weights are used to improve illness detection techniques described herein. In particular, the predictive weights and/or the pattern adjustment models may be input into the classifier to determine satisfaction (or lack thereof) of deviation criteria which are used to identify illness. In particular, higher user activeness metrics on the weekends, and lower user activeness metrics on the weekdays, may be used to determine different "predictive weights" on weekends and weekdays, respectively, where changes in sleep data, activity data, or both, are evaluated relative to the respective predictive weights.

In some implementations, the system 200 may utilize pattern adjustment models configured to account for predictable, cyclical changes in physiological data attributed to normal menstrual cycles (e.g., menstrual cycle model). For example, it has been found that naturally-cycling users exhibit changes in physiological data based on where the respective user is within their own menstrual cycles. Such temperature deviations may be attributable to progesterone, a hormone which regulates menstrual cycles. For instance, a user's temperature may fluctuate throughout the user's menstrual cycle, where the user may generally exhibit maximum temperature readings during the luteal phase of the menstrual cycle. In this regard, utilizing menstrual cycle models may enable the system 200 to more efficiently determine changes in physiological data and other parameters (e.g., sleep data, activity data) which are attributable to illness, and which changes are simply due to the user's natural menstrual cycle. In particular, the use of menstrual cycle models may reduce or eliminate a frequency with which the system 200 incorrectly interprets natural temperature increases throughout a menstrual cycle as being indicative of illness.

In some implementations, the system 200 may generate a menstrual cycle model for each respective user. In other words, the system 200 may utilize physiological data for each respective user to generate a menstrual cycle model which is tailored to the respective user. This may be further shown and described with reference to FIG. 11.

Figure 11:
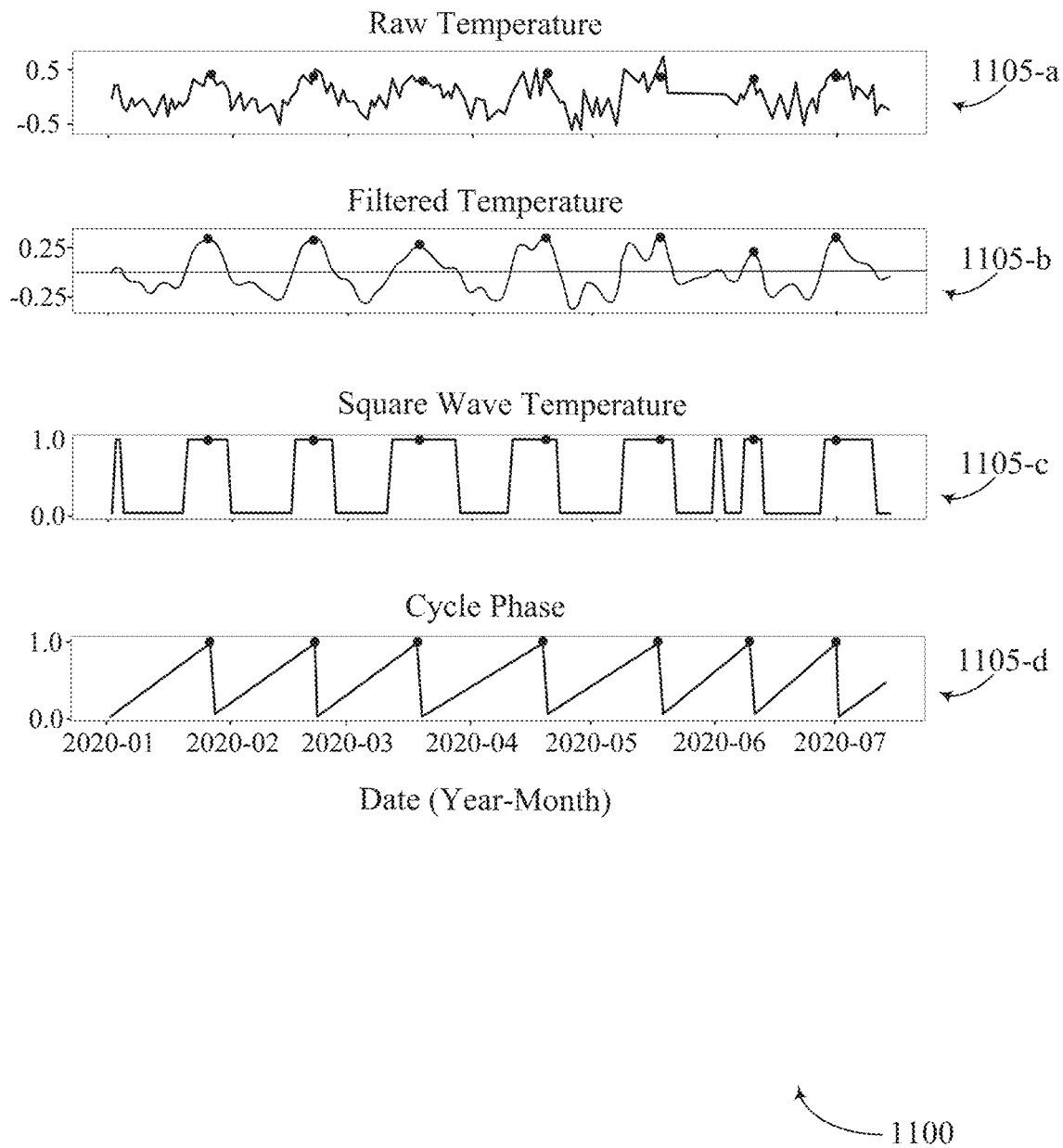
FIG. 11 illustrates an example of a menstrual cycle model that supports illness detection techniques in accordance with aspects of the present disclosure.

FIG. 11 illustrates an example of a menstrual cycle model 1100 that supports illness detection techniques in accordance with aspects of the present disclosure. In particular, the menstrual cycle model 1100 illustrates a raw temperature data diagram 1105-a, a filtered temperature data diagram 1105-b, a square wave temperature data diagram 1105-c, and a cycle phase diagram 1105-d.

The x-axis of each of the respective diagrams illustrates time (e.g., date) over which a menstrual cycle for a user is evaluated. The y-axis of the raw temperature data diagram 1105-a and the filtered temperature data diagram 1105-b illustrates deviations in a user's high daily temperature readings (in degrees Celsius), measured relative to the user's average high daily temperature readings over some reference period (e.g., previous sixty days). In other words, the y-axis of the diagrams 1105-a and 1105-b illustrate within-user temperature deviations. The y-axis of the square wave temperature data diagram 1105-c illustrates the predicted phase of the cycle, where 1 indicates luteal phase and 0 indicates follicular phase. The y-axis of the cycle phase diagram 1105-d illustrates a phase of the user's menstrual cycle from 0 to 1, where 0 indicates a beginning of a new menstrual period and 1 indicates an end of the menstrual period.

In some aspects, the system 200 may acquire physiological data (e.g., temperature data) from a user over time. In some cases, the user device 106 and/or server 110 may determine a single daily temperature for each respective day, which typically represents a high nighttime temperature reading for the respective day. The single high temperature readings are shown in the raw temperature data diagram 1105-a. Subsequently, the user device 106 and/or server 110 may filter the raw temperature data (e.g., apply a band pass filter) to generate the filtered temperature data diagram 1105-b. Filtering the temperature data may remove any abnormally high or low temperature readings from the raw temperature data diagram 1105-a, which may be attributable to hot showers, being in the sun, etc.

A peak-finding algorithm may be used on the respective diagrams 1105 to identify peaks in temperature readings (e.g., temperature readings which are greater than or equal to some temperature threshold), which as illustrated within the respective diagrams 1105. Generally, the peak-finding algorithm may find peaks in temperature readings, which may generally correspond to a specific phase (e.g., luteal phase) within the menstrual cycle. In other words, in some implementations, peak-finding algorithms may be used to identify temperature spikes which may correspond to an end of a menstrual period, when users generally exhibit naturally heightened temperatures.

In some cases, the system 200 may implement the peak-finding algorithm in accordance with generally-understood knowledge regarding menstrual periods. For example, menstrual cycles for most naturally-cycling women typically last between 20 and 40 days. As such, in some cases, the peak-finding algorithm may be configured to identify peaks which are at least 15 days apart from one another, such that the peak-finding algorithm does not identify temperature peaks (and therefore menstrual periods) which are less than 15 days apart from one another. In this regard, the system 200 may implement a menstrual cycle duration threshold in order to generate the menstrual cycle model. The term "menstrual cycle duration threshold" may refer to an estimated timing of a menstrual period relative to a preceding menstrual period (e.g., duration between menstrual periods), an estimated duration timing between a luteal phase relative to a previous luteal phase, an estimated timing for a follicular phase relative to a preceding follicular phase, or any combination thereof. The use of a menstrual cycle duration threshold may also enable the system to more efficiently identify specific phases within a menstrual cycle in the presence of noisy temperature readings which may be attributable to birth control and/or menopause. Moreover, in some implementations, the peak-finding algorithm may be configured to identify temperature peaks only if the user's temperature readings are elevated (e.g., satisfy some temperature threshold) for a certain quantity of days.

Subsequently, the user device 106 and/or server 110 may identify characteristics (e.g., menstrual periods) of the user's menstrual cycle. In some cases, the system 200 may identify menstrual periods based on the peaks identified via the peak-finding algorithm (e.g., based on the menstrual cycle duration threshold). In additional or alternative cases, the system 200 may identify menstrual periods of the menstrual cycle for a respective user based on user inputs received via the user device 106. For example, a user may input one or more user inputs via the GUI 275 of the user device 106, where the user inputs are associated with a menstrual cycle for the user. The user inputs may indicate a start/end of a menstrual period of the menstrual cycle, an ovulation period of the menstrual cycle, and the like. In some cases, the system 200 may cause the user device 106 (e.g., GUI 275) to display a prompt for user inputs related to the user's menstrual cycle, where user inputs are received in response to the prompt.

In this regard, the system 200 may be configured to utilize acquired physiological data, user inputs, or both, to determine characteristics of the user's menstrual cycle (e.g., start/end of menstrual periods, start/end of ovulation periods, start/end of follicular phases, start/end of luteal phases, temperature readings throughout the menstrual cycle, etc.). In some cases, the system 200 may cause the user device 106 to display one or more characteristics of the menstrual cycle to the user (e.g., via the GUI 275).

The system 200 may then generate a menstrual cycle model for the user based on the identified characteristics of the menstrual cycle for the respective user (e.g., based on identified start/end of menstrual periods, identified start/end of follicular/luteal phases, etc.). For example, as shown in the cycle phase diagram 1105-d, a menstrual cycle model may indicate a cycle phase for the user. The cycle phase may be measured from 0 to 1 to indicate how far through a menstrual period (e.g., percentage of the way through) the user is over time. For example, if a menstrual period for the user generally lasts 25 days, each day would account for $\frac{1}{25}$=0.04 of the menstrual cycle. For instance, a first day of a new menstrual period may be represented by 0.04 in the cycle phase diagram 1105-d ($\frac{1}{25}$=0.04), and a second day of the menstrual period may be represented by 0.08 in the cycle phase diagram 1105-d ($\frac{2}{25}$=0.08). Similarly, the twenty-fifth day (e.g., probable last day) of the menstrual period may be represented by 1 in the cycle phase diagram 1105-d (25/25=1), indicating that the menstrual period is at the end, or likely to be close to the end.

Upon generating the menstrual cycle model for the user, the system 200 may utilize the menstrual cycle model to more efficiently determine scores (e.g., sleep scores, readiness scores) for the user. For example, based on the menstrual cycle model, a classifier may be configured to identify that the user generally exhibits heightened temperatures toward the end of each menstrual period. In this regard, the classifier may be configured to take into account expected high temperatures during the latter portions of a menstrual period when determining sleep and readiness scores.

Moreover, the system 200 may be configured to utilize menstrual cycle models for each respective user in order to improve illness detection/prediction techniques described herein. By inputting a menstrual cycle model for a user into the classifier along with physiological data for the user, the classifier may be configured to more efficiently identify whether changes in physiological data (e.g., increases in temperature readings) are attributable to oncoming illness, or simply attributable to the user's natural menstrual cycle.

For example, in some implementations, the system 200 may determine one or more predictive weights for temperature data acquired from the user based on the determined menstrual cycle model. As noted previously herein, the predictive weights may be associated with a relative predictive accuracy of the temperature data for predicting illness. In particular, temperature data with a higher predictive weight may be more indicative of illness (e.g., higher predictive accuracy), whereas temperature data with a lower predictive weight may be less indicative of illness (e.g., lower predictive accuracy). For instance, referring to the cycle phase diagram 1105-d, the system 200 may determine that high temperature readings acquired during the earlier portions of a menstrual period (e.g., days closer to 0 on the scale of 0-1) are associated with higher predictive weights, whereas high temperature readings acquired during the later portions of the menstrual period (e.g., days closer to 1 on the scale of 0-1) are associated with lower predictive weights. These predictive weights may take into account the fact that the user naturally exhibits heightened temperature readings near the end of each menstrual period, such that heightened temperature readings toward the end of each menstrual period are natural and expected, and therefore less likely to be indicative of illness.

By way of another example, a user's temperature readings which are acquired during a menstrual period, luteal phase, and/or follicular phase may be associated with relatively lower predictive weights (e.g., lower relative predictive accuracy for detecting illness), whereas a user's temperature readings which are acquired outside of a menstrual period, luteal phase, and/or follicular phase may be associated with relatively higher predictive weights (e.g., higher relative predictive accuracy for detecting illness).

The user device 106 and/or server 110 may be configured to weight temperature data acquired from the user over time using the one or more predictive weights to generate weighted temperature data. By weighting acquired temperature data, the system 200 (e.g., classifier implemented by the system 200) may be configured to account for the fact that heightened temperature readings throughout a natural menstrual cycle may be more or less indicative of illness, depending on when throughout the menstrual cycle the respective temperature readings were collected. The weighted temperature readings may then be used to identify a satisfaction of deviation criteria which are used to determine/predict illness.

In some implementations, the system 200 may be configured to test and validate classifiers, algorithms, or models used to determine/predict illness based on data collected from multiple users. For example, the server 110 of the system 200 may receive training data from a set of user devices 106. Each of the user devices 106 may be associated with (e.g., communicatively coupled to) a ring 104 or other wearable device 104 which is configured to collect physiological data from a respective user. The training data may include collected physiological data (e.g., temperature data, HRV data, etc.) and/or user status data collected from a set of users. Moreover, the server 110 may be configured to generate and transmit illness assessment metrics (e.g., illness risk metrics, illness prediction metrics) to the user devices 106.

Continuing with the same example, the server 110 may acquire physiological data (e.g., temperature data) and user status data from a set of user devices 106. The user status data may include a variety of types of data. For example, user status data may include symptom data, such as symptom descriptions and timing. User status data may also include diagnostic status. In some implementations, user status data may include self-reported data that the user may report to the server 110. In other implementations, the user status data may be reported to the server 110 by another party. In some implementations, self-reported data may be verified by external sources (e.g., a doctor's diagnosis and test results). In some implementations, user status data may include conclusions derived from user physiological data, such as symptoms/illnesses (e.g., a fever) determined based on the temperature data or other user physiological data.

Example self-reported data may include symptoms that are indicative of an illness, such as influenza A/B or COVID-19. In other implementations, symptoms may be more commonly associated with cognitive or mental health issues, such as depression and anxiety, as these concerns can also arise in the context of infection or immune dysregulation. In some implementations, the server 110 and/or user device 106 may provide a list of symptoms/illnesses for the user to select from in a web-based GUI 275 and/or application GUI 275. The user status data may be reported at various times. For example, the user status data may be reported once (e.g., at illness onset) or multiple times (e.g., on a daily basis). In this regard, the illness detection models may be semi-supervised by user feedback in response to receiving algorithmically generated predictions of sickness likelihood. For example, a user may be provided with a menu of options or a checklist of possible recent behavioral or environmental or health-related changes that could alternatively account for a phase transition detected by the ring or other device. A user's response to such prompting may then be used (e.g., in a Bayesian fashion) to adjust future predictions for that user.

Additional example user status data and training data may include, but is not limited to: 1) blood/swab/biological or medical tests to confirm diagnoses or quantify infection/immunity/vaccination responses, 2) medical record data, 3) derivation of symptom recall bias based on timing of self-reports relative to time the user reports having experienced the symptoms (e.g., a feature in the model to calibrate confidence in self-reports relative to recall biases affecting subjective symptom reporting), 4) COVID-19 prevalence rates by region (city, zip code, etc.) over time, 5) prevalence specific to certain centers of employment (e.g., a hospital or meat-packing plant or sports team) and/or occupational roles (e.g., nurse or hospital administrator), 6) census-based data on rural/urban population density, SES, and demographics, 7) weather data on external temperatures, humidity, etc., and 8) traffic data (e.g., used to derive metrics of whether users take public transit and quantify the movement of local populations).

In some implementations, user status data may include other data, such as user geolocation (e.g., latitude/longitude) associated with the acquired temperature data. Such geolocation data may be used to generate prediction models that are geolocation specific. Additionally, the geolocation data may be used to assess whether the user is likely to transition to the unhealthy state. User status data may also indicate a user's employment location and type, user demographic data (e.g., age and sex), other health conditions, or other data that describes the user and/or user's environment. Any of the user status data described herein may be used to make more targeted prediction models and prediction determinations.

The server 110 (e.g., model generation module) may train one or more illness prediction models (e.g., classifiers, algorithms, or other models used to detect/predict illness) using a training set of data that includes the physiological data (e.g., temperature data) and associated user status data. The server 110 may use a variety of different labeled training data to generate the illness prediction models (e.g., classifiers) described herein. In some implementations, the server 110 may use training data that includes relative distribution values divided into daily values. The server 110 may also include labels for each day of relative distribution data indicating whether the user was healthy or unhealthy. For example, the labels may be a 1 for unhealthy (e.g., symptom onset) and a 0 for healthy. In this example, the illness prediction model may generate an illness risk metric for the users. In some cases, the illness risk metric may include an illness prediction value between 0-1 that indicates a likeliness that the user is transitioning to the unhealthy state. The server 110 may generate the illness prediction models using data for a plurality of days (e.g., weeks) for each user.

Subsequently, the server 110 may test/validate the performance of the one or more illness prediction models (e.g., classifiers). In some implementations, the server 110 may test/validate the one or more illness prediction models by comparing outputs from the one or more illness prediction models to the training data. In other words, the server 110 may test/validate the performance of the one or more illness prediction models using supervised learning techniques. The server 110 may then generate illness assessment metrics (e.g., illness risk metrics, illness prediction values) for users using the one or more illness prediction models, as described herein, where the illness assessment metrics are associated with a probability or likelihood that the respective user will transition from a healthy state to an unhealthy state.

In some implementations, the user device 106 and/or server 110 may generate and/or interpret the illness assessment metrics (e.g., illness risk metrics, illness prediction values) based on characteristics of each respective user. For example, the server 110 may generate and/or interpret the illness risk metrics based on a location of the user. In one example, a user in a geolocation where an illness is more prevalent at the time may be alerted for lower indicated probabilities of illness than a user that is in a geolocation where the illness is not prevalent (e.g., using Bayesian statistical or other methodologies). Similarly, the server 110 may generate/interpret the illness risk metrics based on similarity with other users, such as users in the same place/type of employment (e.g., the same office, same frontline work, etc.), involving cluster or mixed modeling techniques. In this case, the server 110 may warn users of possible illness for lower probabilities in cases where others at the place of employment have been ill. In some implementations, the thresholds may be set by a manager/employer. One or more prediction models may be trained and/or used based on user characteristics.

Figure 12:
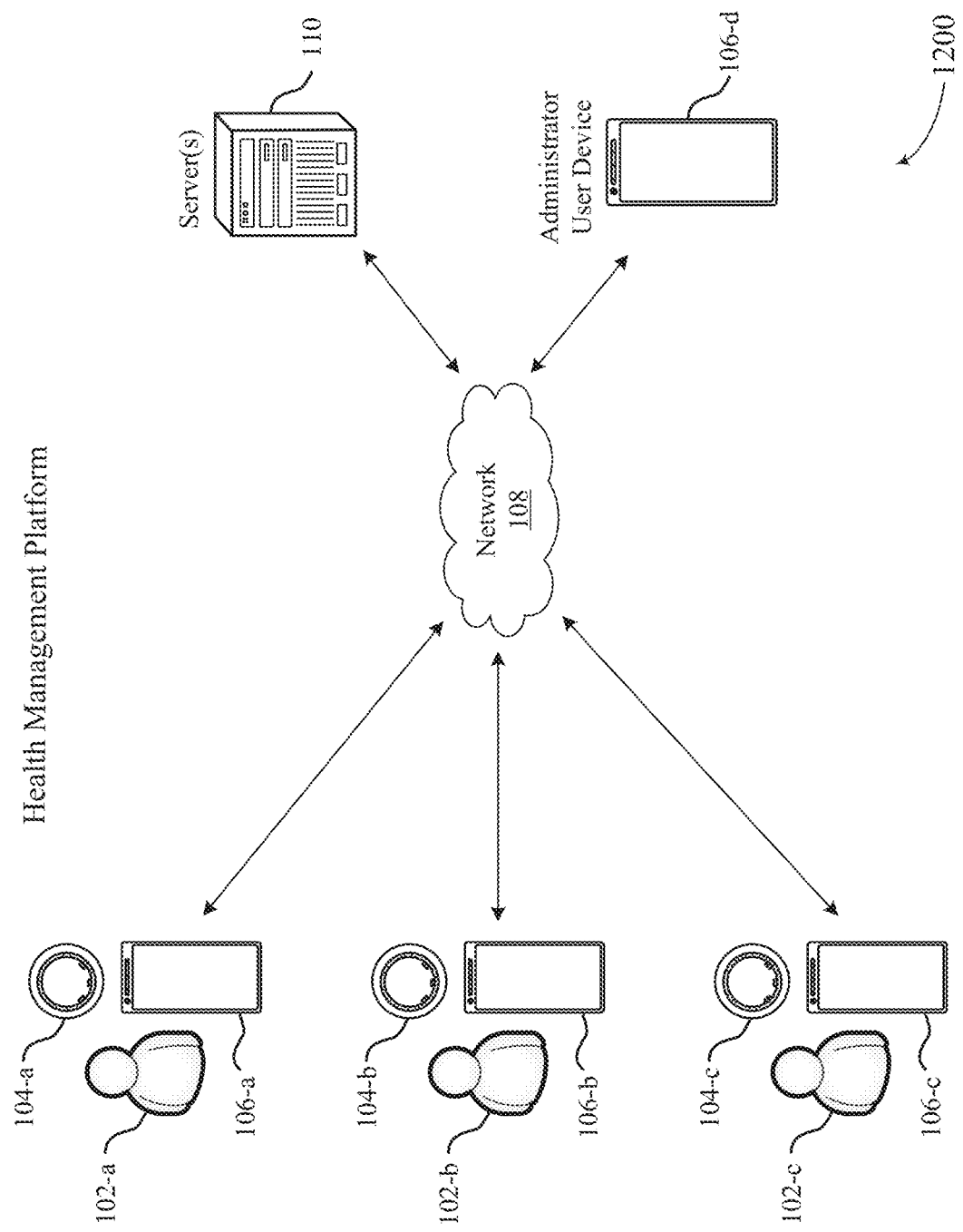
FIG. 12 illustrates an example of a health management platform that supports illness detection techniques in accordance with aspects of the present disclosure.

FIG. 12 illustrates an example of a health management platform 1200 that supports illness detection techniques in accordance with aspects of the present disclosure. The health management platform 1200 may implement, or be implemented by, aspects of the system 100, the system 200, or both.

The health management platform 1200 may be configured to perform health monitoring (e.g., HRM services) for one or more users 102. In particular, the health management platform 1200 may be configured to monitor (e.g., continuously monitor) physiological data for one or more users 102 in order to provide physiological data, illness risk metrics, and the like, to some administrator (e.g., administrator user device 106-*d*) associated with the one or more users 102. In some implementations, the administrator user device 106-*d* may be operated by, or associated with, a health care professional (e.g., doctor, nurse), an administrator of an organization (e.g., business owner, business manager), a personal trainer, a coach (e.g., coach of a sports team), and the like. In this regard, the health management platform 1200 may be configured to provide health-related information (e.g., illness risk scores) associated with one or more users 102 to some administrator (administrator user device 106-*d*).

The administrator user device 106-*d* may include an example of the user device 106 illustrated in FIG. 2. In some implementations, the administrator user device 106-*d* may include one of the user devices 106-*a*, 106-*b*, and/or 106-*c*. In other words, in some cases, one of the users 102-*a*, 102-*b*, and 102-*c* may include an administrator who receives health-related information for each of the respective users 102-*a*, 102-*b*, and 102-*c*. In other cases, the administrator user device 106-*d* may include a separate device, such that the administrator is not one of the users 102-*a*, 102-*b*, and 102-*c*.

For example, the health management platform 1200 may include a first user 102-*a*, a second user 102-*b*, and a third user 102-*c*. Each of the users 102-*a*, 102-*b*, and 102-*c* may be associated with corresponding wearable devices (e.g., rings 104-*a*, 104-*b*, and 104-*c*, respectively) and corresponding user devices 106-*a*, 106-*b*, and 106-*c*, respectively. As described herein with reference to FIG. 2, each of the rings 104-*a*, 104-*b*, and 104-*c* may be configured to continuously acquire physiological data (e.g., temperature information, HRV information, respiratory rate information) associated with the respective users 102-*a*, 102-*b*, and 102-*c*. The rings

104 may be configured to continuously acquire physiological data at regular or irregular intervals, and transmit acquired physiological data to the corresponding user devices 106-a, 106-b, and 106-c.

Subsequently, the user devices 106-a, 106-b, and 106-c may be configured to perform processing operations on the physiological data received from the respective rings 104-a, 104-b, and 104-c. Additionally, or alternatively, the user devices 106-a, 106-b, and 106-c may transmit (e.g., relay, forward) the received physiological data to one or more servers 110 (e.g., via a network 108), where the one or more servers 110 are configured to perform the processing operations described herein.

In some implementations, the health management platform 1200 may cause a GUI of an administrator user device 106-d to display all or portions of the physiological data acquired from the respective users, and/or parameters computed/identified based on the acquired physiological data. For example, in cases where the administrator user device 106-d is associated with an administrator of a doctor's office for the users 102-a, 102-b, and 102-c, the administrator user device 106-d may receive and display physiological data associated with the respective users 102, sleep data (e.g., sleep stages, sleep durations) for the respective users 102, and the like. In this regard, the health management platform 1200 may enable health-related data for each of the respective users to be continuously reported to applicable healthcare professionals or other users, which may enable more accurate and comprehensive healthcare decisions for the respective users 102.

In some implementations, the health management platform 1200 may report illness-related metrics (e.g., illness risk metrics, illness prediction metrics) to the administrator user device 106-d. For example, the user devices 106-a, 106-b, 106-c and/or the server 110 may be configured to determine illness risk metrics (e.g., illness prediction metrics, illness assessment metrics) for each of the respective users 102-a, 102-b, and 102-c. The respective components may be configured to determine illness risk metrics in accordance with the techniques described herein, including through the use of one or more classifiers (e.g., machine learning classifiers). Subsequently, the user devices 106-a, 106-b, 106-c and/or the server 110 may report the illness risk metrics to the administrator user device 106-d. In this regard, the user devices 106-a, 106-b, 106-c and/or the server 110 may cause a GUI of the administrator user device 106-d to display at least one illness risk metric for at least one of the users 102.

In some implementations, the health management platform 1200 may display physiological data and/or illness risk metrics on the administrator user device 106-d based on a comparison of the respective illness risk metrics. For example, the administrator user device 106-d may display illness risk metrics for the respective users in order of users 102 who are most at risk of illness (e.g., highest illness risk scores) to users 102 who are least at risk of illness (e.g., lowest illness risk scores). In other cases, illness risk scores may be displayed on the administrator user device 106-d in some other order.

In some aspects, the health management platform 1200 may report physiological data and/or illness risk metrics (via the administrator user device 106-d) based on one or more user inputs received via the administrator user device 106-d and/or other user devices 106. User inputs may be associated with identification of illness risk metrics, reporting illness risk metrics, or both. In other words, user inputs may be used to tailor how illness risk metrics are reported, which illness risk metrics are reported, and the like. User inputs may be associated with a threshold for identifying illness risk metrics, a threshold for reporting illness risk metrics, or both.

For example, an administrator may input (e.g., via the administrator user device 106-d) a threshold for reporting illness risk metrics. In this example, the health management platform 1200 may be configured to report illness risk metrics to the administrator user device 106-d only if the respective illness risk metrics satisfy (e.g., are greater than or equal to) the threshold. In this regard, the health management platform 1200 may be tailored such that illness alerts are only generated if the health management platform 1200 predicts that a user 102 will become ill with some threshold confidence. Such techniques may reduce a quantity of alerts which are transmitted to the administrator user device 106-d.

In some aspects, the health management platform 1200 (e.g., server 110, user devices 106-a, 106-b, 106-c) may cause the administrator user device 106-d to display one or more recommendations. The recommendations may be associated with determined illness risk metrics for the respective users 102-a, 102-b, and 102-c. For example, the administrator user device 106-d may display a recommendation that a user 102 schedule a doctor appointment, a recommendation that a user 102 stay home from work or some other activity, a recommendation that a user quarantine, a recommendation for a user 102 to prepare for a potential illness (e.g., hydrate, rest), and the like. As such, the health management platform 1200 may help prevent the spread of illness, and may prevent the likelihood of illness outbreaks.

In some cases, the health management platform 1200 may generate recommendations (via the administrator user device 106-d) for users 102 other than a user 102 who is predicted to become ill. For example, if the server 110 predicts that the first user 102-a is likely to become ill (e.g., high illness risk metric), and the first user 102-a shares a cubicle with the second user 102-b, the server 110 may cause the administrator user device 106-c to display a recommendation that the second user 102-b schedule a doctor appointment or stay home from work based on the illness risk metric for the first user 102-a and potential contact between the first and second users 102.

Moreover, the health management platform 1200 may be configured to modify illness risk metrics of one user 102 based on illness risk metrics of another user 102. For example, continuing with the example above, the first user 102-a and the second user 102-b may share a cubicle. This information may be input into the health management platform 1200 via the administrator user device 106-d, and may be used to determine potential contact between the users 102-a and 102-b and/or potential close proximity between the users 102-a and 102-b. In this example, the server 110 may determine a first illness risk metric for the first user 102-a and a second illness risk metric for the second user 102-b. The first illness risk metric may indicate that it is highly likely that the first user 102-a is or will become ill. As such, the server 110 may be configured to selectively modify (e.g., selectively increase) the second illness risk metric for the second user 102-b based on the first illness risk metric for the first user 102-a and/or the potential contact/potential close proximity between the respective users 102-a and 102-b.

Figure 13:
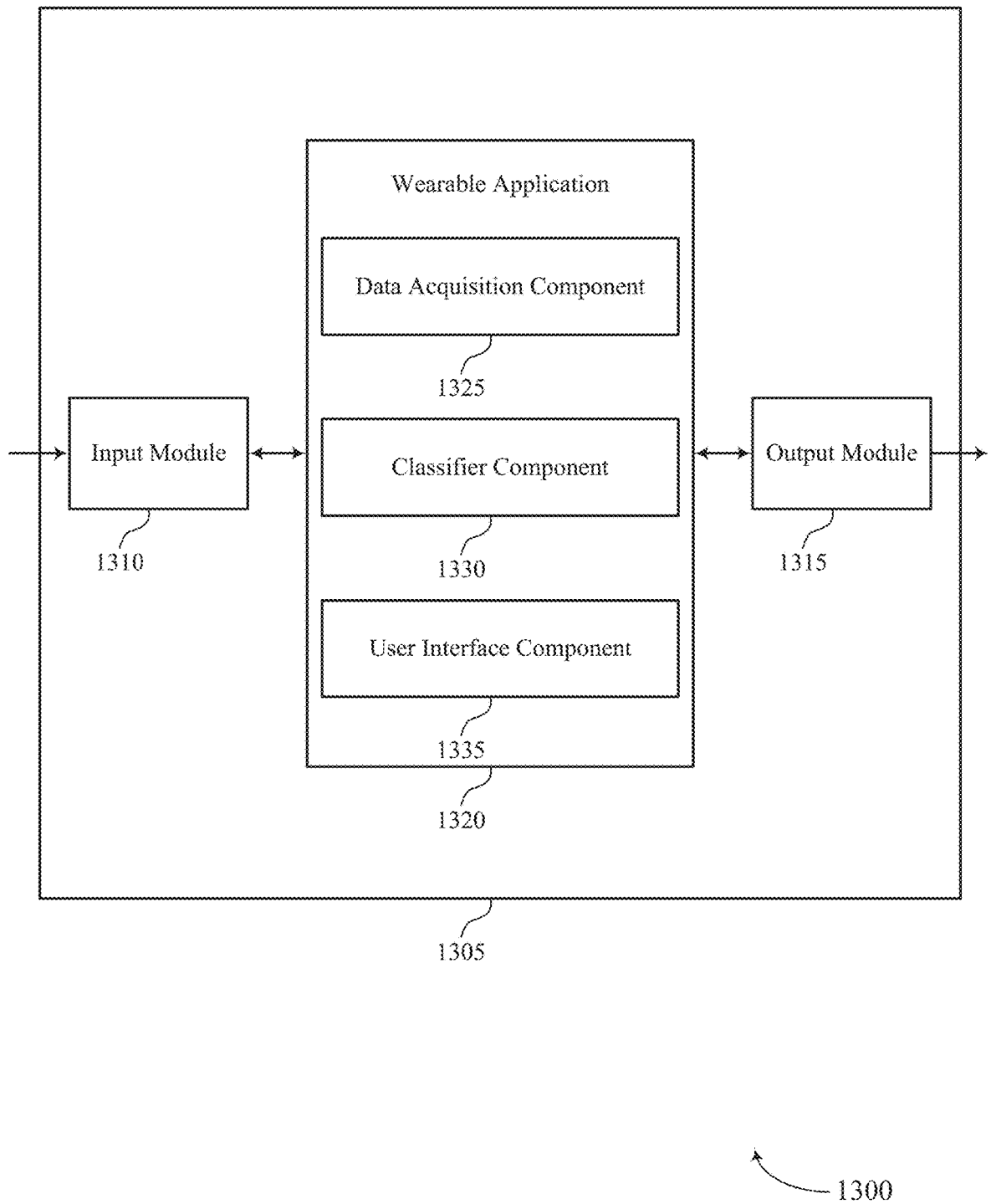
FIG. 13 shows a block diagram of an apparatus that supports illness detection techniques in accordance with aspects of the present disclosure.

FIG. 13 shows a block diagram 1300 of a device 1305 that supports illness detection techniques in accordance with aspects of the present disclosure. The device 1305 may include a input module 1310, a output module 1315, and a wearable application 1320. The device 1305 may also include a processor. Each of these components may be in communication with one another (e.g., via one or more buses).

The input module 1310 may provide a means for receiving information such as packets, user data, control information, or any combination thereof associated with various information channels (e.g., control channels, data channels, information channels related to illness detection techniques). Information may be passed on to other components of the device 1305. The input module 1310 may utilize a single antenna or a set of multiple antennas.

The output module 1315 may provide a means for transmitting signals generated by other components of the device 1305. For example, the output module 1315 may transmit information such as packets, user data, control information, or any combination thereof associated with various information channels (e.g., control channels, data channels, information channels related to illness detection techniques). In some examples, the output module 1315 may be co-located with a input module 1310 in a transceiver module. The output module 1315 may utilize a single antenna or a set of multiple antennas.

For example, the wearable application 1320 may include a data acquisition component 1325, a classifier component 1330, a user interface component 1335, or any combination thereof. In some examples, the wearable application 1320, or various components thereof, may be configured to perform various operations (e.g., receiving, monitoring, transmitting) using or otherwise in cooperation with the input module 1310, the output module 1315, or both. For example, the wearable application 1320 may receive information from the input module 1310, send information to the output module 1315, or be integrated in combination with the input module 1310, the output module 1315, or both to receive information, transmit information, or perform various other operations as described herein.

The wearable application 1320 may support automatically detecting illness in accordance with examples as disclosed herein. The data acquisition component 1325 may be configured as or otherwise support a means for receiving HRV data associated with a user from a wearable device, the HRV data collected via the wearable device throughout a first time interval and a second time interval subsequent to the first time interval. The classifier component 1330 may be configured as or otherwise support a means for inputting the HRV data into a classifier. The classifier component 1330 may be configured as or otherwise support a means for identifying a satisfaction of one or more deviation criteria between a first subset of the HRV data collected throughout the first time interval and a second subset of the HRV data collected throughout the second time interval. The user interface component 1335 may be configured as or otherwise support a means for causing a GUI of a user device to display an illness risk metric associated with the user based at least in part on the satisfaction of the one or more deviation criteria, the illness risk metric associated with a relative probability that the user will transition from a healthy state to an unhealthy state.

Figure 14:
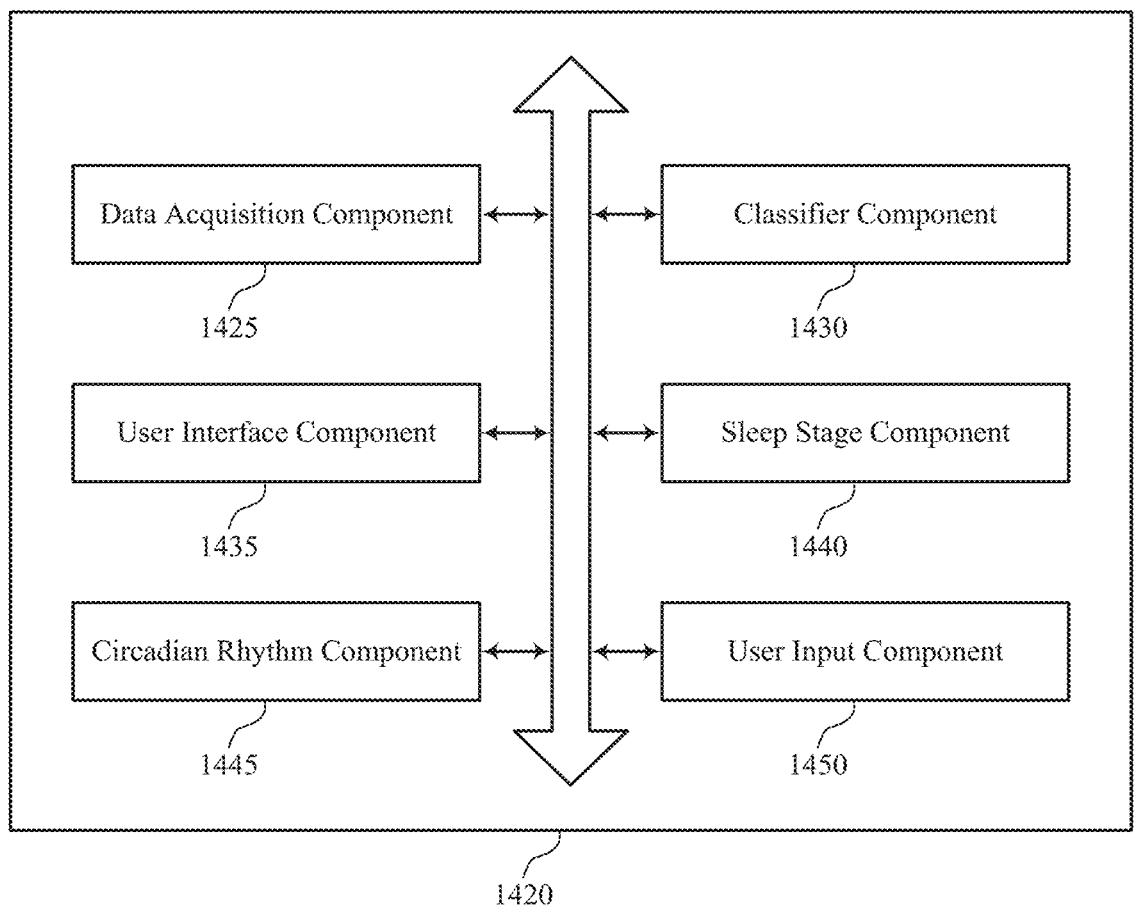
FIG. 14 shows a block diagram of a wearable application that supports illness detection techniques in accordance with aspects of the present disclosure.

FIG. 14 shows a block diagram 1400 of a wearable application 1420 that supports illness detection techniques in accordance with aspects of the present disclosure. The wearable application 1420 may be an example of aspects of a wearable application or a wearable application 1320, or both, as described herein. The wearable application 1420, or various components thereof, may be an example of means for performing various aspects of illness detection techniques as described herein. For example, the wearable application 1420 may include a data acquisition component 1425, a classifier component 1430, a user interface component 1435, a sleep stage component 1440, a circadian rhythm component 1445, a user input component 1450, or any combination thereof. Each of these components may communicate, directly or indirectly, with one another (e.g., via one or more buses).

The wearable application 1420 may support automatically detecting illness in accordance with examples as disclosed herein. The data acquisition component 1425 may be configured as or otherwise support a means for receiving HRV data associated with a user from a wearable device, the HRV data collected via the wearable device throughout a first time interval and a second time interval subsequent to the first time interval. The classifier component 1430 may be configured as or otherwise support a means for inputting the HRV data into a classifier. In some examples, the classifier component 1430 may be configured as or otherwise support a means for identifying a satisfaction of one or more deviation criteria between a first subset of the HRV data collected throughout the first time interval and a second subset of the HRV data collected throughout the second time interval. The user interface component 1435 may be configured as or otherwise support a means for causing a GUI of a user device to display an illness risk metric associated with the user based at least in part on the satisfaction of the one or more deviation criteria, the illness risk metric associated with a relative probability that the user will transition from a healthy state to an unhealthy state.

In some examples, the classifier component 1430 may be configured as or otherwise support a means for determining frequency content of the HRV data throughout at least a portion of the first time interval and at least a portion of the second time interval, wherein identifying the satisfaction of the one or more deviation criteria is based at least in part on the frequency content.

In some examples, to support determining the frequency content of the HRV data, the classifier component 1430 may be configured as or otherwise support a means for determining a low frequency content of the HRV data. In some examples, to support determining the frequency content of the HRV data, the classifier component 1430 may be configured as or otherwise support a means for determining a high frequency content of the HRV data, wherein identifying the satisfaction of the one or more deviation criteria is based at least in part on the low frequency content, the high frequency content, or both.

In some examples, the classifier component 1430 may be configured as or otherwise support a means for identifying a divergence between the low frequency content of the HRV data and the high frequency content of the HRV data between the first time interval and the second time interval, wherein identifying the satisfaction of the one or more deviation criteria is based at least in part on identifying the divergence.

In some examples, the data acquisition component 1425 may be configured as or otherwise support a means for receiving physiological data associated with the user from the wearable device, the physiological data collected via the wearable device throughout the first time interval and the second time interval. In some examples, the sleep stage component 1440 may be configured as or otherwise support a means for identifying a plurality of sleep stages associated with the user based at least in part on the physiological data. In some examples, the sleep stage component 1440 may be configured as or otherwise support a means for identifying a first portion of the HRV data which corresponds to a first sleep stage of the plurality of sleep stages within the first time interval, and a second portion of the HRV data which corresponds to a second sleep stage of the plurality of sleep stages within the second time interval, the first sleep stage and the second sleep stage comprising the same type of sleep stage, wherein inputting the HRV data into the classifier comprises inputting the first portion of the HRV data and the second portion of the HRV data.

In some examples, the circadian rhythm component 1445 may be configured as or otherwise support a means for identifying at least a first portion of the first time interval and a second portion of the second time interval based at least in part on a circadian rhythm associated with the user. In some examples, the circadian rhythm component 1445 may be configured as or otherwise support a means for identifying a first portion of the HRV data which corresponds to the first portion of the first time interval and a second portion of the HRV data which corresponds to the second portion of the second time interval, wherein inputting the HRV data into the classifier comprises inputting the first portion of the HRV data and the second portion of the HRV data.

In some examples, the classifier component 1430 may be configured as or otherwise support a means for identifying an RMSSD metric associated with the HRV data, wherein identifying the satisfaction of the one or more deviation criteria is based at least in part on the RMSSD metric.

In some examples, the data acquisition component 1425 may be configured as or otherwise support a means for receiving physiological data associated with the user from the wearable device, the physiological data collected via the wearable device throughout the first time interval and the second time interval. In some examples, the classifier component 1430 may be configured as or otherwise support a means for identifying, based at least in part on the physiological data, resting heart rate data, HRV averaging score data, recovery metric data, or any combination thereof. In some examples, the classifier component 1430 may be configured as or otherwise support a means for inputting the resting heart rate data, the HRV averaging score data, the recovery metric data, or any combination thereof, into the classifier, wherein identifying the satisfaction of the one or more deviation criteria is based at least in part on the resting heart rate data, the HRV averaging score data, the recovery metric data, or any combination thereof.

In some examples, the classifier component 1430 may be configured as or otherwise support a means for identifying a decrease in the resting heart rate data between the first time interval and the second time interval, a decrease in the HRV averaging score data between the first time interval and the second time interval, an increase in the recovery metric data between the first time interval and the second time interval, or any combination thereof, wherein identifying the satisfaction of the one or more deviation criteria is based at least in part on the decrease in the resting heart rate data, the decrease in the HRV averaging score data, the increase in the recovery metric data, or any combination thereof.

In some examples, the data acquisition component 1425 may be configured as or otherwise support a means for receiving physiological data associated with the user from the wearable device, the physiological data collected via the wearable device throughout the first time interval and the second time interval. In some examples, the classifier component 1430 may be configured as or otherwise support a means for inputting the physiological data into the classifier. In some examples, the classifier component 1430 may be configured as or otherwise support a means for classifying the physiological data collected throughout the first and second time intervals into a plurality of sleep intervals within the first time interval and the second time interval, each sleep interval of the plurality of sleep intervals associated with one of an awake sleep stage, a light sleep stage, a REM sleep stage, or a deep sleep stage, wherein identifying the satisfaction of the one or more deviation criteria is based at least in part on classifying the physiological data.

In some examples, the classifier component 1430 may be configured as or otherwise support a means for identifying a first change in a first duration of sleep stages associated with the REM sleep stage between the first time interval and the second time interval, a second change in a second duration of sleep stages associated with the deep sleep stage between the first time interval and the second time interval, or both, wherein identifying the satisfaction of the one or more deviation criteria is based at least in part on the first change, the second change, or both.

In some examples, the user input component 1450 may be configured as or otherwise support a means for receiving a user input via the user device and in response to causing the GUI to display the illness risk metric. In some examples, the classifier component 1430 may be configured as or otherwise support a means for training the classifier using the user input. In some examples, the user input indicates a positive illness test, an onset of illness symptoms, or both.

In some examples, the wearable device comprises a wearable ring device. In some examples, the wearable device collects the HRV data from the user using based on arterial blood flow. In some examples, the user device comprises a user device associated with the user, a user device associated with an administrator associated with a group of users including the user, or both.

In some examples, the HRV data is associated with a plurality of users including the user, and the classifier component 1430 may be configured as or otherwise support a means for identifying an illness risk metric associated with each user of the plurality of users based at least in part on the HRV data for each respective user. In some examples, the HRV data is associated with a plurality of users including the user, and the user interface component 1435 may be configured as or otherwise support a means for causing the GUI of an administrator user device to display at least one illness risk metric associated with at least one user of the plurality of users.

Figure 15:
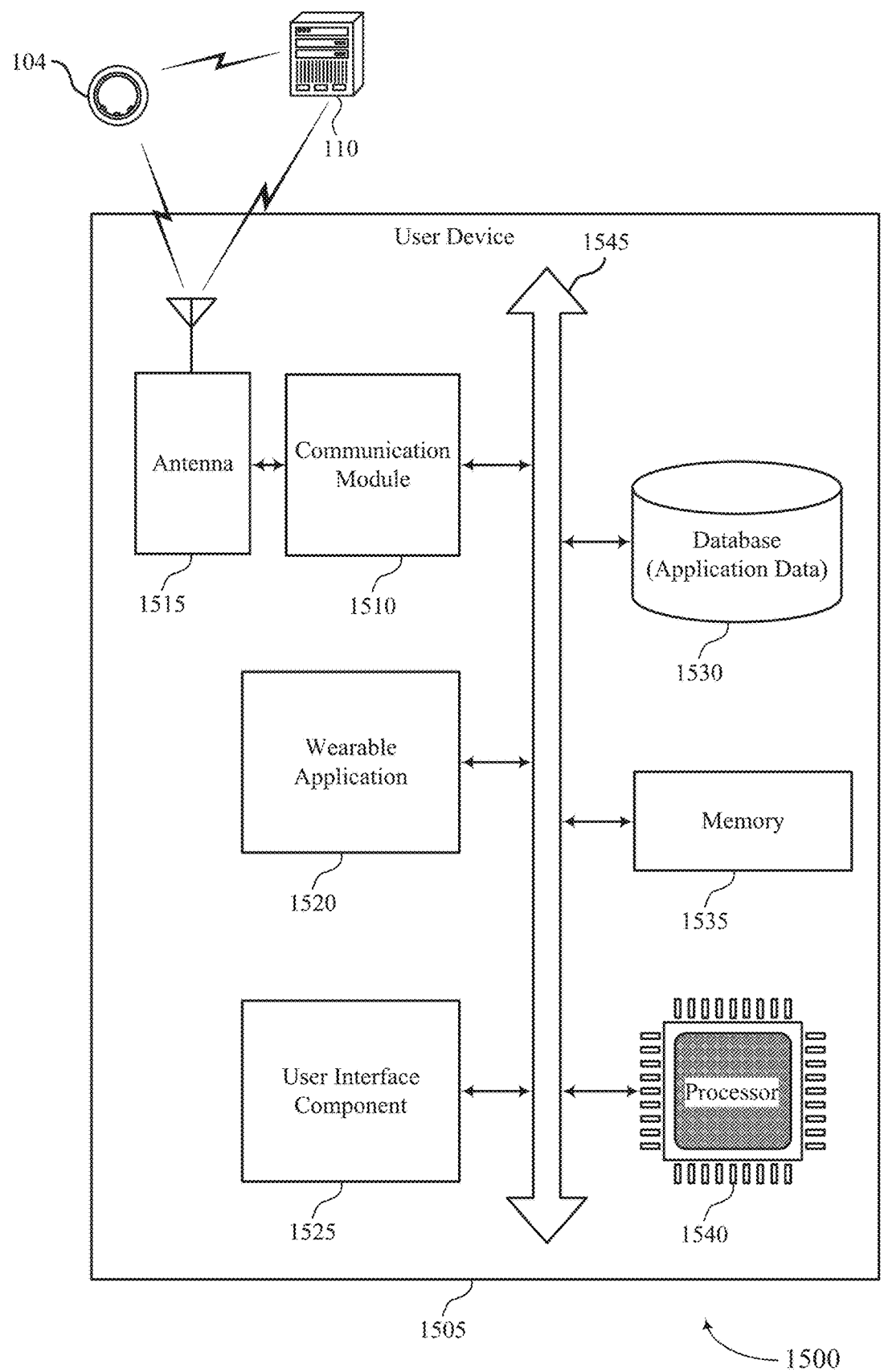
FIG. 15 shows a diagram of a system including a device that supports illness detection techniques in accordance with aspects of the present disclosure.

FIG. 15 shows a diagram of a system 1500 including a device 1505 that supports illness detection techniques in accordance with aspects of the present disclosure. The device 1505 may be an example of or include the components of a device 1505 as described herein. In some implementations, the device 1505 may include an example of a user device 106 described herein. The device 1505 may include components for bi-directional communications with a wearable device (e.g., ring 104) and a server 110, such as a communication module 1510, an antenna 1515, a wearable application 1520, a user interface component 1525, a database 1530, a memory 1535, and a processor 1540. These components may be in electronic communication or otherwise coupled (e.g., operatively, communicatively, functionally, electronically, electrically) via one or more buses (e.g., a bus 1545).

The communication module 1510 may manage input and output signals for the device 1505 via the antenna 1515. The communication module 1510 may include an example of the communication module 220-b of the user device 106 shown and described in FIG. 2. In this regard, the communication module 1510 may manage communications with the ring 104 and the server 110, as illustrated in FIG. 2. The communication module 1510 may also manage peripherals not integrated into the device 1505. In some cases, the communication module 1510 may represent a physical connection or port to an external peripheral. In some cases, the communication module 1510 may utilize an operating system such as iOS®, ANDROID®, MS-DOS®, MS-WINDOWS®, OS/2®, UNIX®, LINUX®, or another known operating system. In other cases, the communication module 1510 may represent or interact with a wearable device (e.g., ring 104), modem, a keyboard, a mouse, a touchscreen, or a similar device. In some cases, the communication module 1510 may be implemented as part of the processor 1540. In some examples, a user may interact with the device 1505 via the communication module 1510, user interface component 1525, or via hardware components controlled by the communication module 1510.

In some cases, the device 1505 may include a single antenna 1515. However, in some other cases, the device 1505 may have more than one antenna 1515, which may be capable of concurrently transmitting or receiving multiple wireless transmissions. The communication module 1510 may communicate bi-directionally, via the one or more antennas 1515, wired, or wireless links as described herein. For example, the communication module 1510 may represent a wireless transceiver and may communicate bi-directionally with another wireless transceiver. The communication module 1510 may also include a modem to modulate the packets, to provide the modulated packets to one or more antennas 1515 for transmission, and to demodulate packets received from the one or more antennas 1515.

The user interface component 1525 may manage data storage and processing in a database 1530. In some cases, a user may interact with the user interface component 1525. In other cases, the user interface component 1525 may operate automatically without user interaction. The database 1530 may be an example of a single database, a distributed database, multiple distributed databases, a data store, a data lake, or an emergency backup database.

The memory 1535 may include RAM and ROM. The memory 1535 may store computer-readable, computer-executable software including instructions that, when executed, cause the processor 1540 to perform various functions described herein. In some cases, the memory 1535 may contain, among other things, a basic I/O system (BIOS) which may control basic hardware or software operation such as the interaction with peripheral components or devices.

The processor 1540 may include an intelligent hardware device, (e.g., a general-purpose processor, a digital signal processor (DSP), a central processing unit (CPU), a microcontroller, an application-specific integrated circuit (ASIC), a field-programmable gate array (FPGA), a programmable logic device, a discrete gate or transistor logic component, a discrete hardware component, or any combination thereof). In some cases, the processor 1540 may be configured to operate a memory array using a memory controller. In other cases, a memory controller may be integrated into the processor 1540. The processor 1540 may be configured to execute computer-readable instructions stored in a memory 1535 to perform various functions (e.g., functions or tasks supporting a method and system for sleep staging algorithms).

The wearable application 1520 may support automatically detecting illness in accordance with examples as disclosed herein. For example, the wearable application 1520 may be configured as or otherwise support a means for receiving HRV data associated with a user from a wearable device, the HRV data collected via the wearable device throughout a first time interval and a second time interval subsequent to the first time interval. The wearable application 1520 may be configured as or otherwise support a means for inputting the HRV data into a classifier. The wearable application 1520 may be configured as or otherwise support a means for identifying, using the classifier, a satisfaction of one or more deviation criteria between a first subset of the HRV data collected throughout the first time interval and a second subset of the HRV data collected throughout the second time interval. The wearable application 1520 may be configured as or otherwise support a means for causing a GUI of a user device to display an illness risk metric associated with the user based at least in part on the satisfaction of the one or more deviation criteria, the illness risk metric associated with a relative probability that the user will transition from a healthy state to an unhealthy state.

By including or configuring the wearable application 1520 in accordance with examples as described herein, the device 1505 may support techniques for improved illness detection/prediction. In particular, techniques described herein may enable illness detection in the pre-symptomatic stage based on nervous system related characteristics/parameters which may be acquired via a wearable device 104. As such, by enabling for illness detection in the pre-symptomatic stage, techniques described herein may reduce a spread of illness, and reduce a severity of illness.

Figure 16:
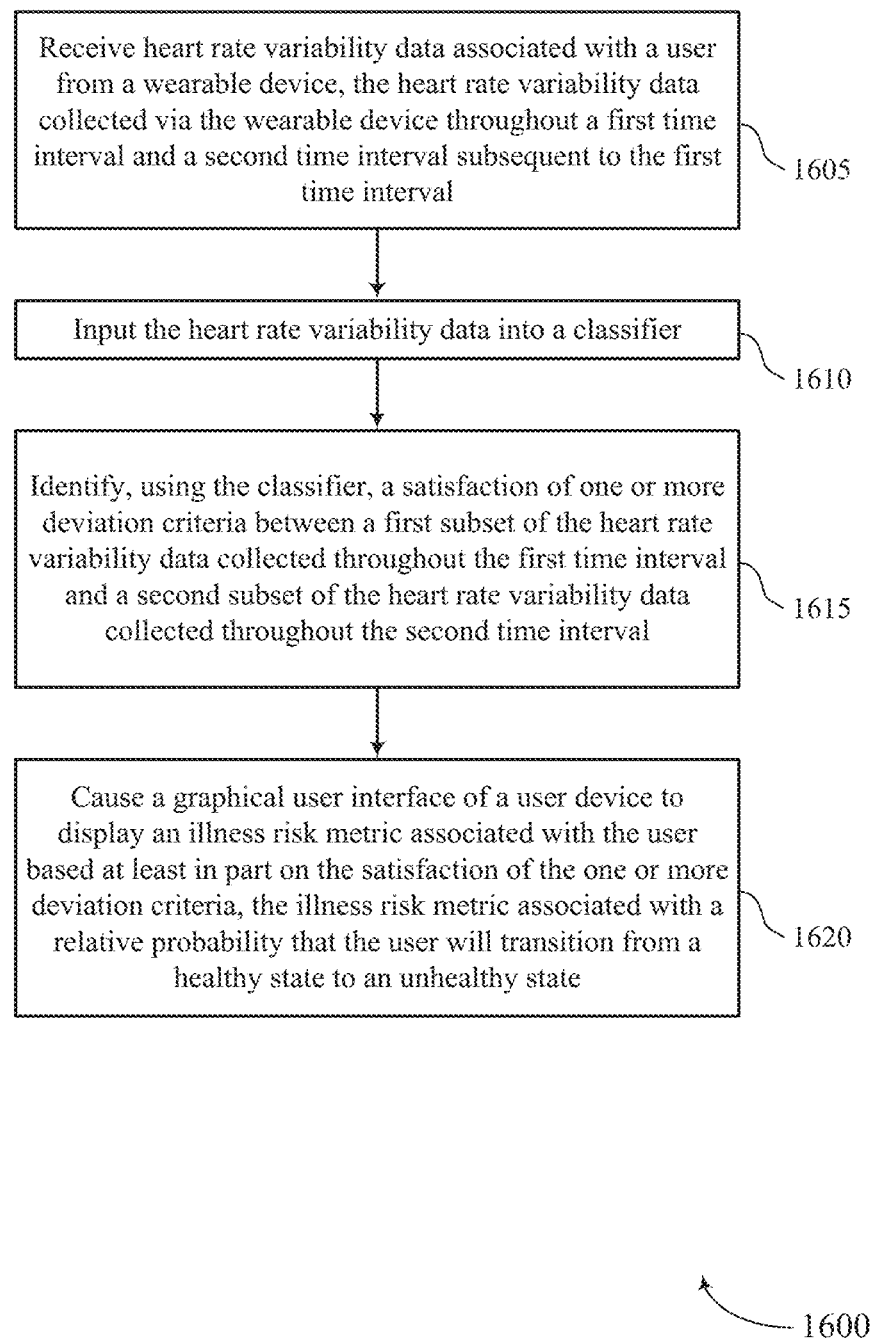
FIGS. 16 through 18 show flowcharts illustrating methods that support illness detection techniques in accordance with aspects of the present disclosure.

FIG. 16 shows a flowchart illustrating a method 1600 that supports illness detection techniques in accordance with aspects of the present disclosure. The operations of the method 1600 may be implemented by a user device 106 or its components as described herein. For example, the operations of the method 1600 may be performed by a user device 106 as described with reference to FIGS. 1 through 15. In some examples, a user device 106 may execute a set of instructions to control the functional elements of the user device 106 to perform the described functions. Additionally or alternatively, the user device 106 may perform aspects of the described functions using special-purpose hardware.

At 1605, the method may include receiving HRV data associated with a user from a wearable device, the HRV data collected via the wearable device throughout a first time interval and a second time interval subsequent to the first time interval. The operations of 1605 may be performed in accordance with examples as disclosed herein. In some examples, aspects of the operations of 1605 may be performed by a data acquisition component 1425 as described with reference to FIG. 14.

At 1610, the method may include inputting the HRV data into a classifier. The operations of 1610 may be performed in accordance with examples as disclosed herein. In some examples, aspects of the operations of 1610 may be performed by a classifier component 1430 as described with reference to FIG. 14.

At 1615, the method may include identifying, using the classifier, a satisfaction of one or more deviation criteria between a first subset of the HRV data collected throughout the first time interval and a second subset of the HRV data collected throughout the second time interval. The operations of 1615 may be performed in accordance with examples as disclosed herein. In some examples, aspects of the operations of 1615 may be performed by a classifier component 1430 as described with reference to FIG. 14.

At 1620, the method may include causing a GUI of a user device to display an illness risk metric associated with the user based at least in part on the satisfaction of the one or more deviation criteria, the illness risk metric associated with a relative probability that the user will transition from a healthy state to an unhealthy state. The operations of 1620 may be performed in accordance with examples as disclosed herein. In some examples, aspects of the operations of 1620 may be performed by a user interface component 1435 as described with reference to FIG. 14.

Figure 17:
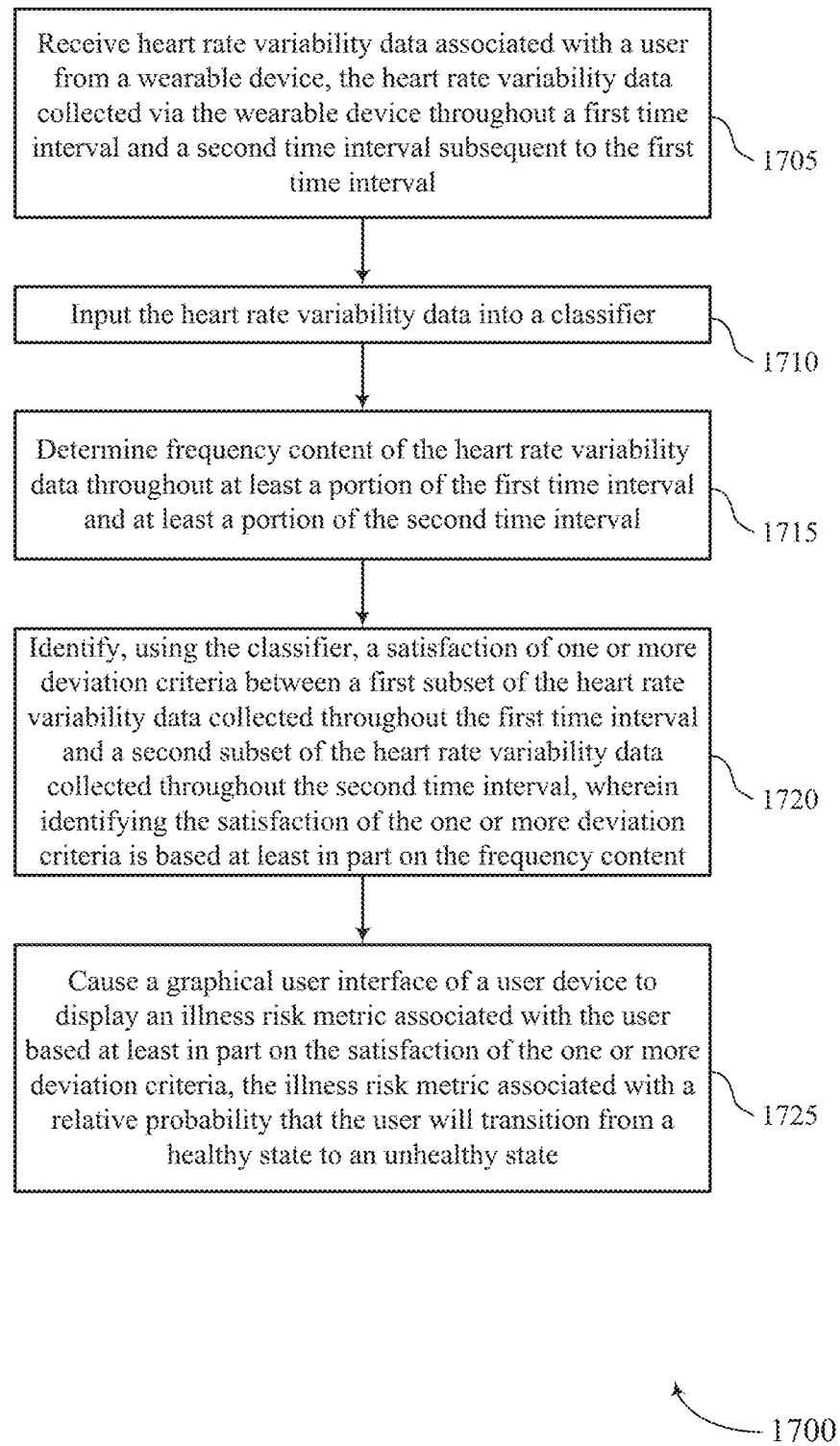

FIG. 17 shows a flowchart illustrating a method 1700 that supports illness detection techniques in accordance with aspects of the present disclosure. The operations of the method 1700 may be implemented by a user device 106 or its components as described herein. For example, the operations of the method 1700 may be performed by a user device 106 as described with reference to FIGS. 1 through 15. In some examples, a user device 106 may execute a set of instructions to control the functional elements of the user device 106 to perform the described functions. Additionally or alternatively, the user device 106 may perform aspects of the described functions using special-purpose hardware.

At 1705, the method may include receiving HRV data associated with a user from a wearable device, the HRV data collected via the wearable device throughout a first time interval and a second time interval subsequent to the first time interval. The operations of 1705 may be performed in accordance with examples as disclosed herein. In some examples, aspects of the operations of 1705 may be performed by a data acquisition component 1425 as described with reference to FIG. 14.

At 1710, the method may include inputting the HRV data into a classifier. The operations of 1710 may be performed in accordance with examples as disclosed herein. In some examples, aspects of the operations of 1710 may be performed by a classifier component 1430 as described with reference to FIG. 14.

At 1715, the method may include determining frequency content of the HRV data throughout at least a portion of the first time interval and at least a portion of the second time interval. The operations of 1715 may be performed in accordance with examples as disclosed herein. In some examples, aspects of the operations of 1715 may be performed by a classifier component 1430 as described with reference to FIG. 14.

At 1720, the method may include identifying, using the classifier, a satisfaction of one or more deviation criteria between a first subset of the HRV data collected throughout the first time interval and a second subset of the HRV data collected throughout the second time interval, wherein identifying the satisfaction of the one or more deviation criteria is based at least in part on the frequency content. The operations of 1720 may be performed in accordance with examples as disclosed herein. In some examples, aspects of the operations of 1720 may be performed by a classifier component 1430 as described with reference to FIG. 14.

At 1725, the method may include causing a GUI of a user device to display an illness risk metric associated with the user based at least in part on the satisfaction of the one or more deviation criteria, the illness risk metric associated with a relative probability that the user will transition from a healthy state to an unhealthy state. The operations of 1725 may be performed in accordance with examples as disclosed herein. In some examples, aspects of the operations of 1725 may be performed by a user interface component 1435 as described with reference to FIG. 14.

Figure 18:
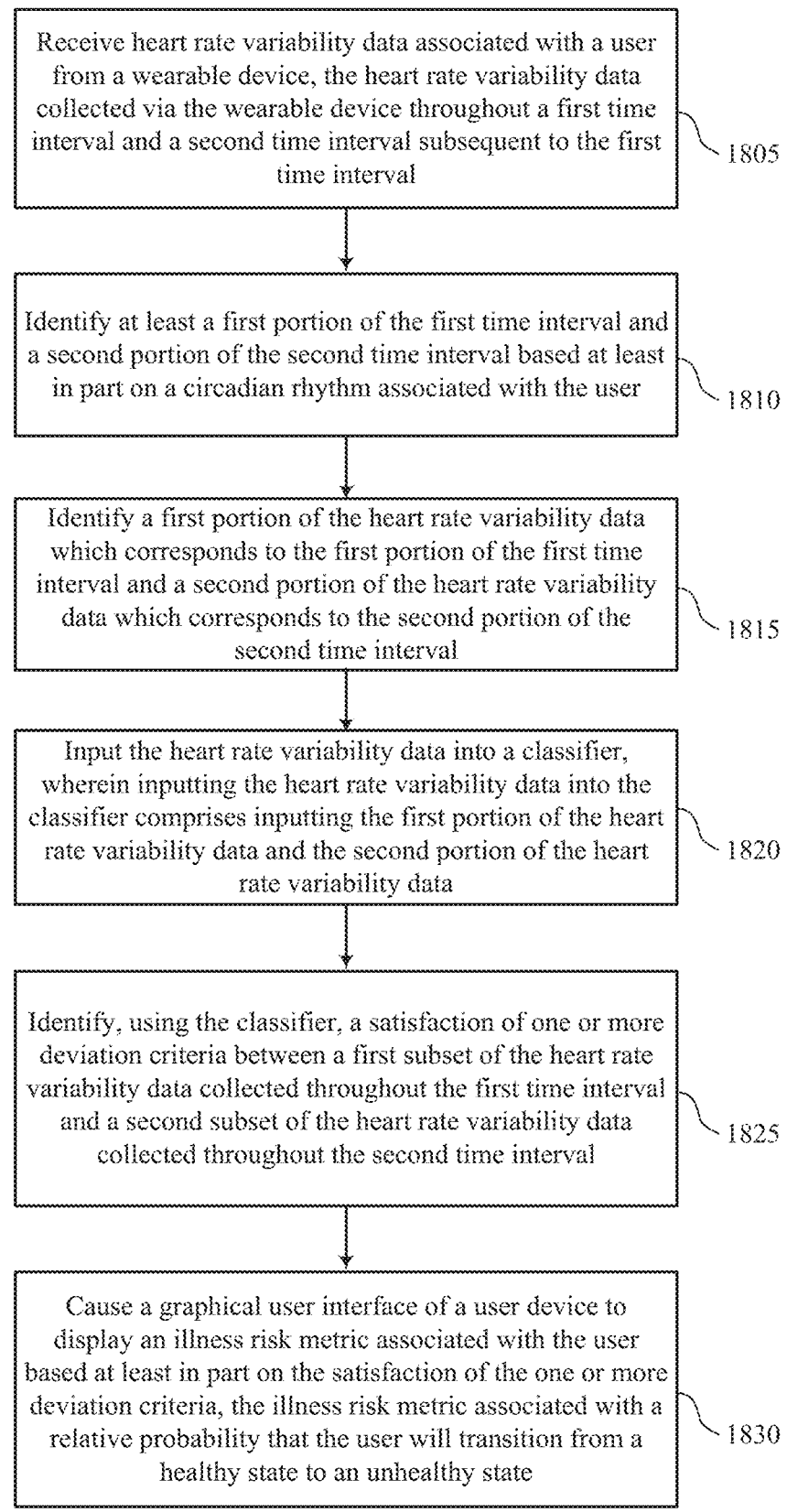

FIG. 18 shows a flowchart illustrating a method 1800 that supports illness detection techniques in accordance with aspects of the present disclosure. The operations of the method 1800 may be implemented by a user device 106 or its components as described herein. For example, the operations of the method 1800 may be performed by a user device 106 as described with reference to FIGS. 1 through 15. In some examples, a user device 106 may execute a set of instructions to control the functional elements of the user device 106 to perform the described functions. Additionally or alternatively, the user device 106 may perform aspects of the described functions using special-purpose hardware.

At 1805, the method may include receiving HRV data associated with a user from a wearable device, the HRV data collected via the wearable device throughout a first time interval and a second time interval subsequent to the first time interval. The operations of 1805 may be performed in accordance with examples as disclosed herein. In some examples, aspects of the operations of 1805 may be performed by a data acquisition component 1425 as described with reference to FIG. 14.

At 1810, the method may include identifying at least a first portion of the first time interval and a second portion of the second time interval based at least in part on a circadian rhythm associated with the user. The operations of 1810 may be performed in accordance with examples as disclosed herein. In some examples, aspects of the operations of 1810 may be performed by a circadian rhythm component 1445 as described with reference to FIG. 14.

At 1815, the method may include identifying a first portion of the HRV data which corresponds to the first portion of the first time interval and a second portion of the HRV data which corresponds to the second portion of the second time interval. The operations of 1815 may be performed in accordance with examples as disclosed herein. In some examples, aspects of the operations of 1815 may be performed by a circadian rhythm component 1445 as described with reference to FIG. 14.

At 1820, the method may include inputting the HRV data into a classifier, wherein inputting the HRV data into the classifier comprises inputting the first portion of the HRV data and the second portion of the HRV data. The operations of 1820 may be performed in accordance with examples as disclosed herein. In some examples, aspects of the operations of 1820 may be performed by a classifier component 1430 as described with reference to FIG. 14.

At 1825, the method may include identifying, using the classifier, a satisfaction of one or more deviation criteria between a first subset of the HRV data collected throughout the first time interval and a second subset of the HRV data collected throughout the second time interval. The operations of 1825 may be performed in accordance with examples as disclosed herein. In some examples, aspects of the operations of 1825 may be performed by a classifier component 1430 as described with reference to FIG. 14.

At 1830, the method may include causing a GUI of a user device to display an illness risk metric associated with the user based at least in part on the satisfaction of the one or more deviation criteria, the illness risk metric associated with a relative probability that the user will transition from a healthy state to an unhealthy state. The operations of 1830 may be performed in accordance with examples as disclosed herein. In some examples, aspects of the operations of 1830 may be performed by a user interface component 1435 as described with reference to FIG. 14.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:
1. A system, comprising:
a wearable device configured to measure physiological data from a user, the physiological data comprising heart rate variability data measured from the user throughout a first time interval and a second time interval subsequent to the first time interval;
a user device communicatively coupled with the wearable device; and
one or more processors communicatively coupled with the wearable device and the user device, the one or more processors configured to:
receive heart rate variability data measured from the user via the wearable device, the heart rate variability data collected via the wearable device throughout the first time interval and the second time interval subsequent to the first time interval;
input the heart rate variability data into a first machine learning classifier, wherein the first machine learning classifier is configured to extract a set of features from the heart rate variability data;
identify, using the first machine learning classifier, root mean square of successive differences (RMSSD) data and resting heart rate data associated with the user based at least in part on the heart rate variability data, input the set of features extracted by the first machine learning classifier into a second machine learning classifier, wherein the set of features extracted by the first machine learning classifier comprise the RMSSD data and the resting heart rate data;

identify, using the second machine learning classifier, a satisfaction of one or more deviation criteria between a first subset of the set of features associated with the first time interval and a second subset of the set of features associated with the second time interval, wherein the second machine learning classifier is configured to identify the satisfaction of the one or more deviation criteria based at least in part on identifying a decrease in the RMSSD data and a decrease in the resting heart rate data occurring at approximately a same time within the second time interval; and transmit instructions to a graphical user interface of the user device to cause the graphical user interface to display an illness risk metric associated with the user based at least in part on the satisfaction of the one or more deviation criteria, the illness risk metric associated with a relative probability that the user will transition from a healthy state to an unhealthy state due to a bacterial infection, a viral infection, or both.

2. The system of claim 1, wherein the one or more processors are further configured to:

determine, using the first machine learning classifier, frequency content of the heart rate variability data throughout at least a portion of the first time interval and at least a portion of the second time interval, wherein the set of features comprise the frequency content, and wherein identifying the satisfaction of the one or more deviation criteria is based at least in part on the frequency content.

3. The system of claim 2, wherein to determine the frequency content of the heart rate variability data, the one or more processors are further configured to:

determine, using the first machine learning classifier, a low frequency content of the heart rate variability data; and determine, using the first machine learning classifier, a high frequency content of the heart rate variability data, wherein the set of features comprise the low frequency content and the high frequency content, wherein identifying the satisfaction of the one or more deviation criteria is based at least in part on the low frequency content, the high frequency content, or both.

4. The system of claim 3, wherein the one or more processors are further configured to:

identify, using the second machine learning classifier, a divergence between the low frequency content of the heart rate variability data and the high frequency content of the heart rate variability data, wherein identifying the satisfaction of the one or more deviation criteria is based at least in part on identifying that the divergence occurs at approximately the same time as the decrease in the RMSSD data and the decrease in the resting heart rate data.

5. The system of claim 1, wherein the one or more processors are further configured to:

receive physiological data associated with the user from the wearable device, the physiological data collected via the wearable device throughout the first time interval and the second time interval;

identify a plurality of sleep stages associated with the user based at least in part on the physiological data; and identify, using the first machine learning classifier, a first portion of the heart rate variability data which corresponds to a first sleep stage of the plurality of sleep stages within the first time interval, and a second portion of the heart rate variability data which corresponds to a second sleep stage of the plurality of sleep stages within the second time interval, the first sleep stage and the second sleep stage comprising the same type of sleep stage, wherein the second machine learning classifier is configured to identify the satisfaction of the one or more deviation criteria based at least in part on a comparison between the first portion of the heart rate variability data and the second portion of the heart rate variability data.

6. The system of claim 1, wherein the one or more processors are further configured to:

identify at least a first portion of the first time interval and a second portion of the second time interval based at least in part on a circadian rhythm associated with the user; and identify a first portion of the heart rate variability data which corresponds to the first portion of the first time interval and a second portion of the heart rate variability data which corresponds to the second portion of the second time interval, wherein inputting the heart rate variability data into the machine learning classifier comprises inputting the first portion of the heart rate variability data and the second portion of the heart rate variability data.

7. The system of claim 1, wherein the illness risk metric is associated with a relative probability that the user is experiencing a viral infection, and wherein the one or more features extracted by the first machine learning classifier are associated with an immunological response of the user during a pre-symptomatic period of the viral infection, and wherein the instructions are transmitted to the graphical user interface during the pre-symptomatic period prior to the user experiencing symptoms of the viral infection.

8. The system of claim 1, wherein the one or more features extracted by the first machine learning classifier comprise a rhythmic pattern of the heart rate variability data that is based at least in part on a circadian rhythm of the user throughout the first time interval, wherein the second machine learning classifier is configured to identify the satisfaction of the one or more deviation criteria based at least in part on the rhythmic pattern and the circadian rhythm.

9. The system of claim 8, wherein the one or more processors are further configured to:

identify an average bedtime of the user, an average wake time of the user, or both, based at least in part on the circadian rhythm of the user; and identify, using the second machine learning classifier, one or more deviations between the heart rate variability data collected during the second time interval from the rhythmic pattern of the heart rate variability data within a first time period immediately subsequent to the average bedtime, within a second time period immediately preceding the average wake time, or both, wherein the satisfaction of the one or more deviation criteria is based at least in part on the one or more deviations.

10. The system of claim 1, wherein the one or more processors are further configured to:

receive physiological data associated with the user from the wearable device, the physiological data collected via the wearable device throughout the first time interval and the second time interval;

input the physiological data into the first machine learning classifier; and classify the physiological data collected throughout the first and second time intervals into a plurality of sleep intervals within the first time interval and the second time interval, each sleep interval of the plurality of sleep intervals associated with one of an awake sleep stage, a light sleep stage, a rapid eye movement sleep stage, or a deep sleep stage, wherein identifying the satisfaction of the one or more deviation criteria is based at least in part on classifying the physiological data.

11. The system of claim 10, wherein the one or more processors are further configured to:

identify, using the second machine learning classifier, a first change in a first duration of sleep stages associated with the rapid eye movement sleep stage between the first time interval and the second time interval, a second change in a second duration of sleep stages associated with the deep sleep stage between the first time interval and the second time interval, or both, wherein identifying the satisfaction of the one or more deviation criteria is based at least in part on the first change, the second change, or both.

12. The system of claim 1, wherein the one or more processors are further configured to:

receive a user input via the user device and in response to causing the graphical user interface to display the illness risk metric, wherein the user input indicates a positive illness test, an onset of illness symptoms, or both; and train the second machine learning classifier to predict illness for the user based at least in part on the user input.

13. The system of claim 1, wherein identifying the decrease in the RMSSD data and the decrease in the resting heart rate data occurring at the same time comprises:

identifying the decrease in the RMSSD data and the decrease in the resting heart rate data occurring within a same sleep day.

14. The system of claim 1, wherein the one or more processors are further configured to:

identify respiratory rate data associated with the user based at least in part on the heart rate variability data; and input the respiratory rate data into the second machine learning classifier, wherein identifying the satisfaction of the one or more deviation criteria is based at least in part on the respiratory rate data.

15. The system of claim 1, wherein the wearable device comprises a wearable ring device.

16. The system of claim 1, wherein the wearable device collects the heart rate variability data from the user based on arterial blood flow.

17. The system of claim 1, wherein the one or more processors are further configured to:

determine demographic illness data associated with a set of users within a geographical location associated with the user, wherein the demographic illness data is associated with a relative probability of illness within the set of users; and input the demographic illness data into the second machine learning classifier, wherein the second machine learning classifier is configured to identify the satisfaction of the one or more deviation criteria based at least in part on the demographic illness data.

18. The system of claim 1, wherein the heart rate variability data is associated with a plurality of users including the user, the heart rate variability data collected via a plurality of wearable devices associated with the plurality of users, wherein the one or more processors are further configured to:

identify, using the second machine learning classifier, an illness risk metric associated with each user of the plurality of users based at least in part on the heart rate variability data for each respective user; and cause the graphical user interface of an administrator user device to display at least one illness risk metric associated with at least one user of the plurality of users.

19. An apparatus, comprising:

one or more processors;

memory coupled with the one or more processors; and instructions stored in the memory and executable by the one or more processors to cause the apparatus to:

receive heart rate variability data measured from a user via a wearable device, the heart rate variability data collected via the wearable device throughout a first time interval and a second time interval subsequent to the first time interval;

input the heart rate variability data into a first machine learning classifier, wherein the first machine learning classifier is configured to extract a set of features from the heart rate variability data;

identify, using the first machine learning classifier, root mean square of successive differences (RMSSD) data and resting heart rate data associated with the user based at least in part on the heart rate variability data, input the set of features extracted by the first machine learning classifier into a second machine learning classifier, wherein the set of features extracted by the first machine learning classifier comprise the RMSSD data and the resting heart rate data;

identify, using the second machine learning classifier, a satisfaction of one or more deviation criteria between a first subset of the set of features associated with the first time interval and a second subset of the set of features associated with the second time interval, wherein the second machine learning classifier is configured to identify the satisfaction of the one or more deviation criteria based at least in part on identifying a decrease in the RMSSD data and a decrease in the resting heart rate data occurring at approximately a same time within the second time interval; and transmit instructions to a graphical user interface of a user device to cause the graphical user interface to display an illness risk metric associated with the user based at least in part on the satisfaction of the one or more deviation criteria, the illness risk metric associated with a relative probability that the user will transition from a healthy state to an unhealthy state due to a bacterial infection, a viral infection, or both.

20. The apparatus of claim 19, wherein the instructions are further executable by the one or more processors to cause the apparatus to:

determine, using the first machine learning classifier, frequency content of the heart rate variability data throughout at least a portion of the first time interval and at least a portion of the second time interval, wherein the set of features comprise the frequency content, and wherein identifying the satisfaction of the one or more deviation criteria is based at least in part on the frequency content.

\* \* \* \* \*